US010939860B2

(12) United States Patent
Levinson et al.

(10) Patent No.: US 10,939,860 B2
(45) Date of Patent: Mar. 9, 2021

(54) TECHNIQUES AND DEVICES ASSOCIATED WITH BLOOD SAMPLING

(71) Applicant: Seventh Sense Biosystems, Inc., Medford, MA (US)

(72) Inventors: Douglas A. Levinson, Sherborn, MA (US); Howard Bernstein, Cambridge, MA (US); Donald E. Chickering, III, Framingham, MA (US); Shawn Davis, Santa Monica, CA (US); Ramin Haghgooie, Arlington, MA (US); Mark Michelman, Reading, MA (US)

(73) Assignee: Seventh Sense Biosystems, Inc., Medford, MA (US)

( * ) Notice: Subject to any disclaimer, the term of this patent is extended or adjusted under 35 U.S.C. 154(b) by 516 days.

(21) Appl. No.: 15/387,459

(22) Filed: Dec. 21, 2016

(65) Prior Publication Data

US 2017/0127990 A1 May 11, 2017

Related U.S. Application Data

(63) Continuation of application No. 14/527,923, filed on Oct. 30, 2014, now abandoned, which is a
(Continued)

(51) Int. Cl.
*A61B 5/00* (2006.01)
*A61B 5/15* (2006.01)
(Continued)

(52) U.S. Cl.
CPC ...... *A61B 5/150099* (2013.01); *A61B 5/0013* (2013.01); *A61B 5/0077* (2013.01);
(Continued)

(58) Field of Classification Search
CPC ... A61B 5/1411; A61B 5/14514; A61B 5/151; A61B 5/157; A61B 5/4839;
(Continued)

(56) References Cited

U.S. PATENT DOCUMENTS 2,735,671 A   2/1956  Kuhn
2,961,233 A  11/1960  Ullrich
(Continued)

FOREIGN PATENT DOCUMENTS

CN  2065878 U  11/1990
CN  1222334 A   7/1999
(Continued)

OTHER PUBLICATIONS

European Examination Report dated Feb. 1, 2017 for Application No. EP 10708432.9.
(Continued)

*Primary Examiner* — Max F Hindenburg
(74) *Attorney, Agent, or Firm* — Wolf, Greenfield & Sacks, P.C.

(57) ABSTRACT

The present invention generally relates to devices and techniques associated with diagnostics, therapies, and other applications, including skin-associated applications, for example, devices for delivering and/or withdrawing fluid from subjects, e.g., through the skin. In some embodiments, the device includes a system for accessing an extractable medium from and/or through the skin of the subject at an access site, and a pressure regulator supported by a support structure, able to create a pressure differential across the skin at at least a portion of the access site. The device may also include, in some cases, a sensor supported by the support structure for determining at least one condition of the extractable medium from the subject, and optionally a signal generator supported by the support structure for generating
(Continued)

a signal relating to the condition of the medium determined by the sensor.

21 Claims, 8 Drawing Sheets

Related U.S. Application Data continuation of application No. 12/716,226, filed on Mar. 2, 2010, now abandoned.

(60) Provisional application No. 61/294,543, filed on Jan. 13, 2010, provisional application No. 61/257,731, filed on Nov. 3, 2009, provisional application No. 61/269,436, filed on Jun. 24, 2009, provisional application No. 61/163,710, filed on Mar. 26, 2009, provisional application No. 61/156,632, filed on Mar. 2, 2009.

(51) Int. Cl.
| | |
|---|---|
| *A61B 5/151* | (2006.01) |
| *A61B 5/145* | (2006.01) |
| *A61B 5/157* | (2006.01) |
| *A61B 5/1459* | (2006.01) |
| *A61B 5/1486* | (2006.01) |

(52) U.S. Cl.
CPC ........ *A61B 5/1438* (2013.01); *A61B 5/14532* (2013.01); *A61B 5/14539* (2013.01); *A61B 5/14546* (2013.01); *A61B 5/151* (2013.01); *A61B 5/157* (2013.01); *A61B 5/150022* (2013.01); *A61B 5/15125* (2013.01); *A61B 5/150221* (2013.01); *A61B 5/150389* (2013.01); *A61B 5/150412* (2013.01); *A61B 5/150442* (2013.01); *A61B 5/150503* (2013.01); *A61B 5/150969* (2013.01); *A61B 5/150984* (2013.01); *A61B 5/486* (2013.01); *A61B 5/685* (2013.01); *A61B 5/743* (2013.01); *A61B 5/0022* (2013.01); *A61B 5/1459* (2013.01); *A61B 5/14865* (2013.01); *A61B 5/150358* (2013.01); *A61B 5/411* (2013.01); *A61B 5/4839* (2013.01); *A61B 5/4845* (2013.01); *A61B 5/6898* (2013.01)

(58) Field of Classification Search
CPC ........ A61B 5/150343; A61B 5/150213; A61B 10/0045; A61B 5/150099; A61B 5/15125; A61B 5/14532; A61B 5/14539; A61B 5/14546
See application file for complete search history.

(56) References Cited

U.S. PATENT DOCUMENTS

| | | |
|---|---|---|
| 2,976,735 A | 3/1961 | Witte |
| 3,060,429 A | 10/1962 | Winston |
| 3,072,122 A | 1/1963 | Rosenthall |
| 3,339,546 A | 9/1967 | Chen |
| 3,519,171 A | 7/1970 | Kinnavy |
| 3,551,554 A | 12/1970 | Herschler |
| 3,645,253 A | 2/1972 | Goverde et al. |
| 3,711,602 A | 1/1973 | Herschler |
| 3,711,606 A | 1/1973 | Herschler |
| 3,740,421 A | 6/1973 | Schmolka |
| 3,753,432 A | 8/1973 | Guerra |
| 3,761,013 A | 9/1973 | Schuster |
| 3,908,657 A | 9/1975 | Kowarski |
| 3,964,482 A | 6/1976 | Gerstel et al. |
| 4,103,684 A | 8/1978 | Ismach |
| 4,150,744 A | 4/1979 | Fennimore |
| 4,203,520 A | 5/1980 | Schuster |
| 4,253,460 A | 3/1981 | Chen et al. |
| 4,280,509 A | 7/1981 | Bethkenhagen et al. |
| 4,329,999 A | 5/1982 | Phillips |
| 4,340,067 A | 7/1982 | Rattenborg |
| 4,437,567 A | 3/1984 | Jeng |
| 4,537,776 A | 8/1985 | Cooper |
| 4,553,552 A | 11/1985 | Valdespino et al. |
| 4,557,943 A | 12/1985 | Rosler et al. |
| 4,572,210 A | 2/1986 | McKinnon |
| 4,615,697 A | 10/1986 | Robinson |
| 4,621,268 A | 11/1986 | Keeling et al. |
| 4,627,445 A | 12/1986 | Garcia et al. |
| 4,637,403 A | 1/1987 | Garcia et al. |
| 4,696,309 A | 9/1987 | Stephan |
| 4,706,676 A | 11/1987 | Peck |
| 4,740,365 A | 4/1988 | Yukimatsu et al. |
| 4,756,314 A | 7/1988 | Eckenhoff et al. |
| 4,764,378 A | 8/1988 | Keith et al. |
| 4,772,470 A | 9/1988 | Inoue et al. |
| 4,796,644 A | 1/1989 | Polaschegg |
| 4,820,720 A | 4/1989 | Sanders et al. |
| 4,821,733 A | 4/1989 | Peck |
| 4,855,298 A | 8/1989 | Yamada et al. |
| 4,856,533 A | 8/1989 | Anraku et al. |
| 4,863,970 A | 9/1989 | Patel et al. |
| 4,908,404 A | 3/1990 | Benedict et al. |
| 4,957,108 A | 9/1990 | Schoendorfer et al. |
| 4,971,068 A | 11/1990 | Sahi |
| 4,973,468 A | 11/1990 | Chiang et al. |
| 5,006,342 A | 4/1991 | Cleary et al. |
| 5,014,718 A | 5/1991 | Mitchen |
| 5,015,677 A | 5/1991 | Benedict et al. |
| 5,036,861 A | 8/1991 | Sembrowich et al. |
| 5,054,499 A | 10/1991 | Swierczek |
| 5,076,273 A | 12/1991 | Schoendorfer et al. |
| 5,108,927 A | 4/1992 | Dorn |
| 5,145,565 A | 9/1992 | Kater et al. |
| 5,161,532 A | 11/1992 | Joseph |
| 5,174,291 A | 12/1992 | Schoonen et al. |
| 5,201,324 A | 4/1993 | Swierczek |
| 5,213,568 A | 5/1993 | Lattin et al. |
| 5,231,993 A | 8/1993 | Haber et al. |
| 5,238,655 A | 8/1993 | Laible et al. |
| 5,279,294 A | 1/1994 | Anderson et al. |
| 5,320,607 A | 6/1994 | Ishibashi |
| 5,379,895 A | 1/1995 | Foslien |
| 5,402,798 A | 4/1995 | Swierczek et al. |
| 5,415,177 A | 5/1995 | Zadini et al. |
| 5,438,984 A | 8/1995 | Schoendorfer |
| 5,441,048 A | 8/1995 | Schoendorfer |
| 5,441,490 A | 8/1995 | Svedman |
| 5,443,080 A | 8/1995 | D'Angelo et al. |
| 5,445,611 A | 8/1995 | Eppstein et al. |
| 5,458,140 A | 10/1995 | Eppstein et al. |
| 5,504,011 A | 4/1996 | Gavin et al. |
| 5,505,212 A | 4/1996 | Keljmann et al. |
| 5,507,288 A | 4/1996 | Bocker et al. |
| 5,516,487 A | 5/1996 | Rosenthal et al. |
| 5,520,727 A | 5/1996 | Vreeland et al. |
| 5,529,581 A | 6/1996 | Cusack |
| 5,540,709 A | 7/1996 | Ramel |
| 5,552,118 A | 9/1996 | Mayer |
| 5,560,543 A | 10/1996 | Smith et al. |
| 5,574,134 A | 11/1996 | Waite |
| 5,580,794 A | 12/1996 | Allen |
| 5,582,184 A | 12/1996 | Erickson et al. |
| 5,636,640 A | 6/1997 | Staehlin |
| 5,638,815 A | 6/1997 | Schoendorfer |
| 5,662,127 A | 9/1997 | De Vaughn |
| 5,676,144 A | 10/1997 | Schoendorfer |
| 5,680,872 A | 10/1997 | Sesekura et al. |
| 5,682,233 A | 10/1997 | Brinda |
| 5,685,875 A | 11/1997 | Hlavinka et al. |
| 5,701,910 A | 12/1997 | Powles et al. |
| 5,714,390 A | 2/1998 | Hallowitz et al. |
| 5,741,138 A | 4/1998 | Rice et al. |
| 5,746,217 A | 5/1998 | Erickson et al. |

(56) References Cited

U.S. PATENT DOCUMENTS

| | | |
|---|---|---|
| 5,800,420 A | 9/1998 | Gross et al. |
| 5,807,375 A | 9/1998 | Gross et al. |
| 5,811,108 A | 9/1998 | Goeringer |
| 5,813,614 A | 9/1998 | Coffee |
| 5,817,011 A | 10/1998 | Schoendorfer |
| 5,817,012 A | 10/1998 | Schoendorfer |
| 5,820,570 A | 10/1998 | Erickson et al. |
| 5,820,622 A | 10/1998 | Gross et al. |
| 5,823,973 A | 10/1998 | Racchini et al. |
| 5,857,983 A | 1/1999 | Douglas et al. |
| 5,858,188 A | 1/1999 | Soane et al. |
| 5,873,900 A | 2/1999 | Maurer et al. |
| 5,876,675 A | 3/1999 | Kennedy |
| 5,879,310 A | 3/1999 | Sopp et al. |
| 5,879,311 A | 3/1999 | Duchon et al. |
| 5,879,367 A | 3/1999 | Latterell et al. |
| 5,885,211 A | 3/1999 | Eppstein et al. |
| 5,891,053 A | 4/1999 | Sesekura |
| 5,897,508 A | 4/1999 | Konrad |
| 5,944,662 A | 8/1999 | Schoendorfer |
| 5,951,492 A | 9/1999 | Douglas et al. |
| 5,951,493 A | 9/1999 | Douglas et al. |
| 5,955,096 A | 9/1999 | Santos et al. |
| 5,963,136 A | 10/1999 | O'Brien |
| 5,964,718 A | 10/1999 | Duchon et al. |
| 5,972,386 A | 10/1999 | Burgoyne |
| 5,985,312 A | 11/1999 | Jacob et al. |
| 5,998,588 A | 12/1999 | Hoffman et al. |
| 6,007,845 A | 12/1999 | Domb et al. |
| 6,015,392 A | 1/2000 | Douglas et al. |
| 6,024,710 A | 2/2000 | Miller et al. |
| 6,027,459 A | 2/2000 | Shain et al. |
| 6,040,135 A | 3/2000 | Tyrrell |
| 6,044,303 A | 3/2000 | Agarwala et al. |
| 6,048,337 A | 4/2000 | Svedman |
| 6,050,988 A | 4/2000 | Zuck |
| 6,063,029 A | 5/2000 | Saita et al. |
| 6,063,039 A | 5/2000 | Cunningham et al. |
| 6,063,365 A | 5/2000 | Shefer et al. |
| 6,066,103 A | 5/2000 | Duchon et al. |
| 6,071,249 A | 6/2000 | Cunningham et al. |
| 6,071,250 A | 6/2000 | Douglas et al. |
| 6,071,251 A | 6/2000 | Cunningham et al. |
| 6,080,116 A | 6/2000 | Erickson et al. |
| 6,083,196 A | 7/2000 | Trautman et al. |
| 6,091,975 A | 7/2000 | Daddona et al. |
| 6,093,156 A | 7/2000 | Cunningham et al. |
| 6,099,484 A | 8/2000 | Douglas et al. |
| 6,107,102 A | 8/2000 | Ferrari |
| 6,126,899 A | 10/2000 | Woudenberg et al. |
| 6,132,449 A | 10/2000 | Lum et al. |
| 6,132,702 A | 10/2000 | Witt et al. |
| 6,133,318 A | 10/2000 | Hart |
| 6,152,889 A | 11/2000 | Sopp et al. |
| 6,152,942 A | 11/2000 | Brenneman et al. |
| 6,155,992 A | 12/2000 | Henning et al. |
| 6,162,639 A | 12/2000 | Douglas |
| 6,190,315 B1 | 2/2001 | Kost et al. |
| 6,192,890 B1 | 2/2001 | Levy et al. |
| 6,203,504 B1 | 3/2001 | Latterell et al. |
| 6,206,841 B1 | 3/2001 | Cunningham et al. |
| 6,219,574 B1 | 4/2001 | Cormier et al. |
| 6,228,100 B1 | 5/2001 | Schraga |
| 6,230,051 B1 | 5/2001 | Cormier et al. |
| 6,234,990 B1 | 5/2001 | Rowe et al. |
| 6,235,313 B1 | 5/2001 | Mathiowitz et al. |
| 6,252,129 B1 | 6/2001 | Coffee |
| 6,261,245 B1 | 7/2001 | Kawai et al. |
| 6,267,724 B1 | 7/2001 | Taylor |
| 6,283,926 B1 | 9/2001 | Cunningham et al. |
| 6,306,104 B1 | 10/2001 | Cunningham et al. |
| 6,306,993 B1 | 10/2001 | Rothbard et al. |
| 6,309,887 B1 | 10/2001 | Ray |
| 6,319,210 B1 | 11/2001 | Douglas et al. |
| 6,322,574 B1 | 11/2001 | Llyod |
| 6,332,871 B1 | 12/2001 | Douglas et al. |
| 6,334,856 B1 | 1/2002 | Allen et al. |
| 6,340,354 B1 | 1/2002 | Rambin |
| 6,349,229 B1 | 2/2002 | Watanabe et al. |
| 6,349,850 B1 | 2/2002 | Cheikh |
| 6,361,944 B1 | 3/2002 | Mirkin et al. |
| 6,364,890 B1 | 4/2002 | Lum et al. |
| 6,379,317 B1 | 4/2002 | Kintzig et al. |
| 6,379,324 B1 | 4/2002 | Gartstein et al. |
| 6,391,471 B1 | 5/2002 | Hiraoka et al. |
| 6,406,919 B1 | 6/2002 | Tyrrell |
| 6,409,679 B2 | 6/2002 | Pyo |
| 6,436,078 B1 | 8/2002 | Svedman |
| 6,440,096 B1 | 8/2002 | Lastovich et al. |
| 6,455,324 B1 | 9/2002 | Douglas |
| 6,461,644 B1 | 10/2002 | Jackson et al. |
| 6,464,649 B1 | 10/2002 | Duchon et al. |
| 6,465,002 B1 | 10/2002 | Mathiowitz et al. |
| 6,485,439 B1 | 11/2002 | Roe et al. |
| 6,485,703 B1 | 11/2002 | Cote et al. |
| 6,491,657 B2 | 12/2002 | Rowe et al. |
| 6,491,902 B2 | 12/2002 | Shefer et al. |
| 6,501,976 B1 | 12/2002 | Sohrab |
| 6,502,697 B1 | 1/2003 | Crampton et al. |
| 6,503,209 B2 | 1/2003 | Hakky et al. |
| 6,503,231 B1 | 1/2003 | Prausnitz et al. |
| 6,506,168 B1 | 1/2003 | Fathallah et al. |
| 6,527,716 B1 | 3/2003 | Eppstein |
| 6,532,386 B2 | 3/2003 | Sun et al. |
| 6,537,243 B1 | 3/2003 | Henning et al. |
| 6,537,264 B1 | 3/2003 | Cormier et al. |
| 6,538,089 B1 | 3/2003 | Samra et al. |
| 6,540,675 B2 | 4/2003 | Aceti et al. |
| 6,548,264 B1 | 4/2003 | Tan et al. |
| 6,558,361 B1 | 5/2003 | Yeshurun |
| 6,562,014 B2 | 5/2003 | Lin et al. |
| 6,589,562 B1 | 7/2003 | Shefer et al. |
| 6,591,124 B2 | 7/2003 | Sherman et al. |
| 6,602,205 B1 | 8/2003 | Erickson et al. |
| 6,603,987 B2 | 8/2003 | Whitson |
| 6,607,495 B1 | 8/2003 | Skalak et al. |
| 6,607,513 B1 | 8/2003 | Down et al. |
| 6,611,707 B1 | 8/2003 | Prausnitz et al. |
| 6,614,522 B1 | 9/2003 | Sopp et al. |
| 6,620,123 B1 | 9/2003 | Mitragotri et al. |
| 6,624,882 B2 | 9/2003 | Sopp et al. |
| 6,626,884 B1 | 9/2003 | Dillon et al. |
| 6,629,057 B2 | 9/2003 | Zweig et al. |
| 6,652,478 B1 | 11/2003 | Gartstein et al. |
| 6,656,147 B1 | 12/2003 | Gertsek et al. |
| 6,660,527 B2 | 12/2003 | Stroup |
| 6,669,961 B2 | 12/2003 | Kim et al. |
| 6,678,554 B1 | 1/2004 | Sun et al. |
| 6,685,921 B2 | 2/2004 | Lawlor |
| 6,689,100 B2 | 2/2004 | Connelly et al. |
| 6,696,075 B2 | 2/2004 | Mathiowitz et al. |
| 6,706,000 B2 | 3/2004 | Perez et al. |
| 6,706,159 B2 | 3/2004 | Moerman et al. |
| 6,712,776 B2 | 3/2004 | Latterell et al. |
| 6,712,792 B2 | 3/2004 | Leong |
| 6,741,877 B1 | 5/2004 | Shults et al. |
| 6,743,211 B1 | 6/2004 | Prausnitz et al. |
| 6,749,575 B2 | 6/2004 | Matriano et al. |
| 6,765,081 B2 | 7/2004 | Lin et al. |
| 6,766,817 B2 | 7/2004 | da Silva |
| 6,768,920 B2 | 7/2004 | Lange et al. |
| 6,783,502 B2 | 8/2004 | Orloff et al. |
| 6,786,874 B2 | 9/2004 | Grace et al. |
| 6,793,633 B2 | 9/2004 | Douglas et al. |
| 6,798,920 B1 | 9/2004 | Wells et al. |
| 6,800,122 B2 | 10/2004 | Anderson et al. |
| 6,811,090 B2 | 11/2004 | Yogi et al. |
| 6,814,760 B2 | 11/2004 | Anderson et al. |
| 6,825,161 B2 | 11/2004 | Shefer et al. |
| 6,826,426 B2 | 11/2004 | Lange et al. |
| 6,837,858 B2 | 1/2005 | Cunningham et al. |
| 6,855,133 B2 | 2/2005 | Svedman |
| 6,860,873 B2 | 3/2005 | Allen et al. |
| 6,878,120 B2 | 4/2005 | Roe et al. |

(56) References Cited

U.S. PATENT DOCUMENTS

| | | | |
|---|---|---|---|
| 6,896,666 | B2 | 5/2005 | Kochamba |
| 6,899,851 | B2 | 5/2005 | Allen et al. |
| 6,908,448 | B2 | 6/2005 | Redding, Jr. |
| 6,918,404 | B2 | 7/2005 | Dias da Silva |
| 6,918,901 | B1 | 7/2005 | Theeuwes et al. |
| 6,923,764 | B2 | 8/2005 | Aceti et al. |
| 6,925,317 | B1 | 8/2005 | Samuels et al. |
| 6,931,277 | B1 | 8/2005 | Yuzhakov et al. |
| 6,940,591 | B2 | 9/2005 | Sopp et al. |
| 6,952,604 | B2 | 10/2005 | DeNuzzio et al. |
| 6,969,351 | B2 | 11/2005 | Knoll |
| 6,969,359 | B2 | 11/2005 | Duchon et al. |
| 6,990,367 | B2 | 1/2006 | Kiser et al. |
| 6,997,886 | B2 | 2/2006 | Latterell et al. |
| 7,001,343 | B2 | 2/2006 | Erickson et al. |
| 7,001,344 | B2 | 2/2006 | Freeman et al. |
| 7,004,928 | B2 | 2/2006 | Aceti et al. |
| 7,008,384 | B2 | 3/2006 | Tapper |
| 7,014,615 | B2 | 3/2006 | Erickson et al. |
| 7,025,774 | B2 | 4/2006 | Freeman et al. |
| 7,037,277 | B1 | 5/2006 | Smith et al. |
| 7,041,067 | B2 | 5/2006 | Sopp et al. |
| 7,041,068 | B2 | 5/2006 | Freeman et al. |
| 7,047,070 | B2 | 5/2006 | Wilkinson et al. |
| 7,066,586 | B2 | 6/2006 | da Silva |
| 7,066,885 | B2 | 6/2006 | Erickson et al. |
| 7,097,631 | B2 | 8/2006 | Trautman et al. |
| 7,131,987 | B2 | 11/2006 | Sherman et al. |
| 7,133,717 | B2 | 11/2006 | Coston et al. |
| 7,137,957 | B2 | 11/2006 | Erickson et al. |
| 7,150,755 | B2 | 12/2006 | Levaughn et al. |
| 7,172,071 | B2 | 2/2007 | Hawkins |
| 7,174,199 | B2 | 2/2007 | Berner et al. |
| 7,182,910 | B2 | 2/2007 | Allen et al. |
| 7,185,764 | B2 | 3/2007 | Lee et al. |
| 7,235,056 | B2 | 6/2007 | Duchon et al. |
| 7,247,144 | B2 | 7/2007 | Douglas et al. |
| 7,264,627 | B2 | 9/2007 | Perez |
| 7,316,671 | B2 | 1/2008 | Lastovich et al. |
| 7,335,166 | B2 | 2/2008 | Faupel et al. |
| 7,344,499 | B1 | 3/2008 | Prausnitz et al. |
| 7,344,587 | B2 | 3/2008 | Khan et al. |
| 7,374,545 | B2 | 5/2008 | Alroy |
| 7,374,949 | B2 | 5/2008 | Kuriger |
| 7,402,441 | B2 | 7/2008 | Lowe et al. |
| 7,413,868 | B2 | 8/2008 | Kauvar et al. |
| 7,422,567 | B2 | 9/2008 | Lastovich et al. |
| 7,429,258 | B2 | 9/2008 | Angel et al. |
| 7,537,590 | B2 | 5/2009 | Santini et al. |
| 7,544,185 | B2 | 6/2009 | Bengtsson |
| 7,556,615 | B2 | 7/2009 | Pettis et al. |
| 7,572,237 | B2 | 8/2009 | Saikley et al. |
| 7,575,717 | B2 | 8/2009 | Cooke et al. |
| 7,585,278 | B2 | 9/2009 | Aceti et al. |
| 7,585,412 | B2 | 9/2009 | Gorsuch et al. |
| 7,631,760 | B2 | 12/2009 | Guelzow et al. |
| 7,758,518 | B2 | 7/2010 | Perez et al. |
| 7,767,017 | B2 | 8/2010 | Lahann et al. |
| 7,811,236 | B2 | 10/2010 | List et al. |
| 7,811,302 | B2 | 10/2010 | Steg |
| 7,833,172 | B2 | 11/2010 | Hein et al. |
| 7,883,473 | B2 | 2/2011 | LeVaughn et al. |
| 7,896,830 | B2 | 3/2011 | Gura et al. |
| 7,942,827 | B2 | 5/2011 | Mir et al. |
| 7,947,772 | B2 | 5/2011 | Lahann |
| 8,043,480 | B2 | 10/2011 | Lahann et al. |
| 8,052,849 | B2 | 11/2011 | Lahann et al. |
| 8,058,077 | B2 | 11/2011 | Groll et al. |
| 8,071,384 | B2 | 12/2011 | Burke et al. |
| 8,075,826 | B2 | 12/2011 | Lastovich et al. |
| 8,133,191 | B2 | 3/2012 | Rosenberg et al. |
| 8,187,708 | B2 | 5/2012 | Lahann |
| 8,202,240 | B2 | 6/2012 | Felt et al. |
| 8,241,651 | B2 | 8/2012 | Lahann |
| 8,246,582 | B2 | 8/2012 | Angel et al. |
| 8,344,028 | B2 | 1/2013 | Xu et al. |
| 8,383,044 | B2 | 2/2013 | Davis et al. |
| 8,465,425 | B2 | 6/2013 | Heller et al. |
| 8,523,894 | B2 | 9/2013 | Schmelzeisen-Redeker et al. |
| 8,561,795 | B2 | 10/2013 | Schott |
| 8,628,724 | B2 | 1/2014 | Kuenstner |
| 8,808,202 | B2 | 8/2014 | Brancazio |
| 8,821,412 | B2 | 9/2014 | Gonzalez-Zugasti et al. |
| 8,821,446 | B2 | 9/2014 | Trautman et al. |
| 8,827,971 | B2 | 9/2014 | Chickering, III et al. |
| 8,870,903 | B2 | 10/2014 | LeVaughn et al. |
| 8,882,794 | B2 | 11/2014 | Lum |
| 8,900,180 | B2 | 12/2014 | Wolter et al. |
| 8,934,955 | B2 * | 1/2015 | Schraga .............. A61B 5/1411 600/347 |
| 8,971,980 | B2 * | 3/2015 | Mace .................. A61B 5/1411 600/345 |
| 9,028,426 | B2 | 5/2015 | List et al. |
| 9,033,898 | B2 | 5/2015 | Chickering, III et al. |
| 9,033,989 | B2 | 5/2015 | Wolfson et al. |
| 9,039,638 | B2 * | 5/2015 | Arnitz ................. A61B 5/1411 600/583 |
| 9,041,541 | B2 | 5/2015 | Levinson et al. |
| 9,101,302 | B2 * | 8/2015 | Mace .................. A61B 5/1411 |
| 9,113,836 | B2 | 8/2015 | Bernstein et al. |
| 9,119,578 | B2 | 9/2015 | Haghgooie et al. |
| 9,295,417 | B2 | 3/2016 | Haghgooie et al. |
| 9,730,624 | B2 | 8/2017 | Gonzalez-Zugasti et al. |
| 9,775,551 | B2 | 10/2017 | Bernstein et al. |
| 10,188,335 | B2 | 1/2019 | Haghgooie et al. |
| 10,543,310 | B2 | 1/2020 | Bernstein et al. |
| 10,799,166 | B2 | 10/2020 | Gonzalez-Zugasti et al. |
| 2001/0005772 | A1 | 6/2001 | Kisakibaru |
| 2002/0010414 | A1 | 1/2002 | Coston et al. |
| 2002/0013538 | A1 | 1/2002 | Teller |
| 2002/0065453 | A1 | 5/2002 | Lesho et al. |
| 2002/0076443 | A1 | 6/2002 | Stein et al. |
| 2002/0077584 | A1 | 6/2002 | Lin et al. |
| 2002/0082543 | A1 | 6/2002 | Park et al. |
| 2002/0087056 | A1 | 7/2002 | Aceti et al. |
| 2002/0099308 | A1 | 7/2002 | Bojan et al. |
| 2002/0099356 | A1 | 7/2002 | Unger et al. |
| 2002/0112981 | A1 | 8/2002 | Cooper et al. |
| 2002/0115967 | A1 | 8/2002 | Svedman |
| 2002/0119136 | A1 | 8/2002 | Johansen |
| 2002/0130042 | A1 | 9/2002 | Moerman et al. |
| 2002/0130093 | A1 | 9/2002 | Ferrara et al. |
| 2002/0138049 | A1 | 9/2002 | Allen |
| 2002/0143320 | A1 | 10/2002 | Levin |
| 2002/0168290 | A1 | 11/2002 | Yuzhakov et al. |
| 2002/0169393 | A1 | 11/2002 | Cunningham et al. |
| 2002/0169394 | A1 | 11/2002 | Eppstein et al. |
| 2002/0169411 | A1 | 11/2002 | Sherman et al. |
| 2002/0177761 | A1 * | 11/2002 | Orloff ................. A61B 5/1486 600/309 |
| 2002/0187556 | A1 | 12/2002 | Shartle et al. |
| 2002/0188221 | A1 | 12/2002 | Sohrab |
| 2003/0004437 | A1 | 1/2003 | Collins et al. |
| 2003/0040682 | A1 | 2/2003 | Tapper |
| 2003/0055326 | A1 | 3/2003 | Sohrab |
| 2003/0083618 | A1 | 5/2003 | Angel et al. |
| 2003/0083645 | A1 | 5/2003 | Angel et al. |
| 2003/0083685 | A1 | 5/2003 | Freeman et al. |
| 2003/0100846 | A1 | 5/2003 | Custer et al. |
| 2003/0109807 | A1 | 6/2003 | Knoll |
| 2003/0113540 | A1 | 6/2003 | Anderson et al. |
| 2003/0135158 | A1 | 7/2003 | Gonnelli |
| 2003/0135167 | A1 | 7/2003 | Gonnelli |
| 2003/0135201 | A1 | 7/2003 | Gonnelli |
| 2003/0135333 | A1 | 7/2003 | Aceti et al. |
| 2003/0143746 | A1 | 7/2003 | Sage |
| 2003/0159615 | A1 | 8/2003 | Anderson et al. |
| 2003/0162304 | A1 | 8/2003 | Dority et al. |
| 2003/0181863 | A1 | 9/2003 | Ackley et al. |
| 2003/0187394 | A1 | 10/2003 | Wilkinson et al. |
| 2003/0187395 | A1 | 10/2003 | Gabel et al. |
| 2003/0195398 | A1 | 10/2003 | Suzuki et al. |
| 2003/0204148 | A1 | 10/2003 | Lange et al. |
| 2003/0208138 | A1 | 11/2003 | Olson |

(56) References Cited

U.S. PATENT DOCUMENTS

| | | |
|---|---|---|
| 2003/0212344 A1 | 11/2003 | Yuzhakov et al. |
| 2003/0212345 A1 | 11/2003 | McAllister et al. |
| 2003/0212347 A1 | 11/2003 | Sohrab |
| 2003/0212423 A1 | 11/2003 | Pugh et al. |
| 2003/0228367 A1 | 12/2003 | Mathiowitz et al. |
| 2004/0010207 A1 | 1/2004 | Flaherty et al. |
| 2004/0053894 A1 | 3/2004 | Mazess et al. |
| 2004/0058458 A1 | 3/2004 | Anker et al. |
| 2004/0087990 A1 | 5/2004 | Boecker et al. |
| 2004/0096959 A1 | 5/2004 | Stiene et al. |
| 2004/0098009 A1 | 5/2004 | Boecker et al. |
| 2004/0102717 A1 | 5/2004 | Qi |
| 2004/0106904 A1 | 6/2004 | Gonnelli et al. |
| 2004/0133126 A1 | 7/2004 | McNenny |
| 2004/0137640 A1 | 7/2004 | Hirao et al. |
| 2004/0138688 A1 | 7/2004 | Giraud |
| 2004/0162521 A1 | 8/2004 | Bengtsson |
| 2004/0163987 A1 | 8/2004 | Allen |
| 2004/0171980 A1 | 9/2004 | Mitragotri et al. |
| 2004/0199103 A1 | 10/2004 | Kwon |
| 2004/0204744 A1 | 10/2004 | Penner et al. |
| 2004/0236250 A1 | 11/2004 | Hodges et al. |
| 2004/0247016 A1 | 12/2004 | Faries et al. |
| 2004/0249310 A1 | 12/2004 | Shartle et al. |
| 2004/0253185 A1 | 12/2004 | Herweck et al. |
| 2005/0015055 A1 | 1/2005 | Yang |
| 2005/0019902 A1 | 1/2005 | Mathies et al. |
| 2005/0027176 A1 | 2/2005 | Xie |
| 2005/0027308 A1 | 2/2005 | Davis et al. |
| 2005/0033197 A1 | 2/2005 | Cottler |
| 2005/0038669 A1 | 2/2005 | Sachdeva et al. |
| 2005/0054907 A1 | 3/2005 | Page et al. |
| 2005/0064529 A1 | 3/2005 | Kwon |
| 2005/0069925 A1 | 3/2005 | Ford et al. |
| 2005/0070819 A1 | 3/2005 | Poux et al. |
| 2005/0085838 A1 | 4/2005 | Thompson et al. |
| 2005/0090766 A1 | 4/2005 | Montanari |
| 2005/0106066 A1 | 5/2005 | Saltsman et al. |
| 2005/0106713 A1 | 5/2005 | Phan et al. |
| 2005/0137481 A1 | 6/2005 | Sheard et al. |
| 2005/0137531 A1 | 6/2005 | Prausnitz et al. |
| 2005/0137536 A1 | 6/2005 | Gonnelli |
| 2005/0172852 A1 | 8/2005 | Anderson et al. |
| 2005/0182307 A1 | 8/2005 | Currie et al. |
| 2005/0196747 A1 | 9/2005 | Stiene |
| 2005/0201974 A1 | 9/2005 | Schestopol et al. |
| 2005/0203360 A1 | 9/2005 | Brauker et al. |
| 2005/0215923 A1 | 9/2005 | Wiegel |
| 2005/0221276 A1 | 10/2005 | Rozakis et al. |
| 2005/0227269 A1 | 10/2005 | Lloyd, Jr. et al. |
| 2005/0228313 A1 | 10/2005 | Kaler et al. |
| 2005/0245844 A1 | 11/2005 | Mace et al. |
| 2005/0249672 A1 | 11/2005 | Bolbot |
| 2005/0251152 A1 | 11/2005 | Herweck et al. |
| 2005/0261632 A1 | 11/2005 | Xu |
| 2005/0261639 A1 | 11/2005 | Herweck |
| 2005/0267422 A1 | 12/2005 | Kriesel |
| 2006/0001551 A1 | 1/2006 | Kraft et al. |
| 2006/0004271 A1 | 1/2006 | Peyser et al. |
| 2006/0004303 A1 | 1/2006 | Weidenhaupt et al. |
| 2006/0030790 A1 | 2/2006 | Braig et al. |
| 2006/0036187 A1 | 2/2006 | Vos et al. |
| 2006/0058602 A1 | 3/2006 | Kwiatkowski et al. |
| 2006/0089566 A1 | 4/2006 | DeHart |
| 2006/0100654 A1 | 5/2006 | Fukuda et al. |
| 2006/0129065 A1 | 6/2006 | Matsumoto et al. |
| 2006/0142651 A1 | 6/2006 | Brister et al. |
| 2006/0157362 A1 | 7/2006 | Schraga |
| 2006/0182738 A1 | 8/2006 | Holmes et al. |
| 2006/0189895 A1 | 8/2006 | Neel et al. |
| 2006/0200046 A1 | 9/2006 | Windus-Smith et al. |
| 2006/0202385 A1 | 9/2006 | Xu et al. |
| 2006/0228259 A1 | 10/2006 | Samsoondar |
| 2006/0257883 A1 | 11/2006 | Bjorkaker et al. |
| 2006/0258959 A1 | 11/2006 | Sode |
| 2006/0264779 A1 | 11/2006 | Kemp et al. |
| 2006/0264782 A1 | 11/2006 | Holmes et al. |
| 2007/0004989 A1 | 1/2007 | Dhillon |
| 2007/0016446 A1 | 1/2007 | Brown |
| 2007/0027427 A1 | 2/2007 | Trautman et al. |
| 2007/0031283 A1 | 2/2007 | Davis et al. |
| 2007/0031293 A1 | 2/2007 | Beatty |
| 2007/0036686 A1 | 2/2007 | Hatamian et al. |
| 2007/0046476 A1 | 3/2007 | Hinkamp |
| 2007/0054119 A1 | 3/2007 | Garstecki et al. |
| 2007/0066934 A1 | 3/2007 | Etheredge et al. |
| 2007/0078414 A1 | 4/2007 | McAllister et al. |
| 2007/0083131 A1 | 4/2007 | Escutia et al. |
| 2007/0088248 A1 | 4/2007 | Glenn et al. |
| 2007/0092637 A1 | 4/2007 | Brown et al. |
| 2007/0100219 A1 | 5/2007 | Sweitzer et al. |
| 2007/0105176 A1 | 5/2007 | Ibey et al. |
| 2007/0112180 A1 | 5/2007 | Gray et al. |
| 2007/0123801 A1 | 5/2007 | Goldberger et al. |
| 2007/0129618 A1 | 6/2007 | Goldberger et al. |
| 2007/0161926 A1 | 7/2007 | Imamura et al. |
| 2007/0161964 A1 | 7/2007 | Yukhazov |
| 2007/0167340 A1 | 7/2007 | Barthel et al. |
| 2007/0169411 A1 | 7/2007 | Thiessen et al. |
| 2007/0173740 A1 | 7/2007 | Chan et al. |
| 2007/0179404 A1 | 8/2007 | Escutia et al. |
| 2007/0185432 A1 | 8/2007 | Etheredge et al. |
| 2007/0185515 A1 | 8/2007 | Stout |
| 2007/0208275 A1 | 9/2007 | Vinogradov et al. |
| 2007/0213638 A1 | 9/2007 | Herbrechtsmeier et al. |
| 2007/0225676 A1 | 9/2007 | Prausnitz et al. |
| 2007/0231355 A1 | 10/2007 | Quadir et al. |
| 2007/0232956 A1 | 10/2007 | Harman et al. |
| 2007/0233199 A1 | 10/2007 | Moore et al. |
| 2007/0237800 A1 | 10/2007 | Lahann |
| 2007/0238943 A1 | 10/2007 | Poulsen et al. |
| 2007/0249962 A1 | 10/2007 | Alden et al. |
| 2007/0275193 A1 | 11/2007 | deSimone et al. |
| 2008/0009763 A1 | 1/2008 | Chiou et al. |
| 2008/0014627 A1 | 1/2008 | Merchant et al. |
| 2008/0021491 A1 | 1/2008 | Freeman et al. |
| 2008/0033319 A1 | 2/2008 | Kloepfer et al. |
| 2008/0051689 A1 | 2/2008 | Gura et al. |
| 2008/0077096 A1 | 3/2008 | Nakamura et al. |
| 2008/0077430 A1 | 3/2008 | Singer et al. |
| 2008/0081695 A1 | 4/2008 | Patchen |
| 2008/0086051 A1 | 4/2008 | Voegele |
| 2008/0099478 A1 | 5/2008 | Gleich |
| 2008/0103434 A1 | 5/2008 | Lastovich et al. |
| 2008/0108959 A1 | 5/2008 | Jung et al. |
| 2008/0112886 A1 | 5/2008 | Mitragotri et al. |
| 2008/0125673 A1 | 5/2008 | Carano et al. |
| 2008/0125743 A1 | 5/2008 | Yuzhakov |
| 2008/0129486 A1 | 6/2008 | Jeckelmann et al. |
| 2008/0140049 A1 | 6/2008 | Kirby |
| 2008/0154107 A1 | 6/2008 | Jina |
| 2008/0167535 A1 | 7/2008 | Stivoric et al. |
| 2008/0167613 A1 | 7/2008 | Khouri et al. |
| 2008/0183140 A1 | 7/2008 | Paproski et al. |
| 2008/0183144 A1 | 7/2008 | Trautman et al. |
| 2008/0200791 A1 | 8/2008 | Simpson et al. |
| 2008/0200838 A1 | 8/2008 | Goldberger et al. |
| 2008/0220411 A1 | 9/2008 | McNaughton et al. |
| 2008/0221407 A1 | 9/2008 | Baker |
| 2008/0269666 A1 | 10/2008 | Wang et al. |
| 2008/0275327 A1 | 11/2008 | Faarbaek et al. |
| 2008/0275378 A1 | 11/2008 | Herndon |
| 2008/0281290 A1 | 11/2008 | Yodfat et al. |
| 2008/0300508 A1 | 12/2008 | Tomer |
| 2008/0319347 A1 | 12/2008 | Keren |
| 2009/0036795 A1 | 2/2009 | Duineveld et al. |
| 2009/0043250 A1 | 2/2009 | Gonnelli |
| 2009/0048536 A1 | 2/2009 | Freeman et al. |
| 2009/0054813 A1 | 2/2009 | Freeman et al. |
| 2009/0054971 A1 | 2/2009 | Mitsunaga et al. |
| 2009/0076453 A1 | 3/2009 | Mejlhede et al. |
| 2009/0099427 A1 | 4/2009 | Jina et al. |
| 2009/0099478 A1 | 4/2009 | Cassells et al. |
| 2009/0099529 A1 | 4/2009 | Anderson et al. |

(56) References Cited

U.S. PATENT DOCUMENTS

| | | |
|---|---|---|
| 2009/0105614 A1 | 4/2009 | Momose et al. |
| 2009/0118662 A1 | 5/2009 | Schnall |
| 2009/0124994 A1 | 5/2009 | Roe |
| 2009/0131829 A1 | 5/2009 | Freeman et al. |
| 2009/0182306 A1 | 7/2009 | Lee et al. |
| 2009/0187160 A1 | 7/2009 | McAllister et al. |
| 2009/0187167 A1 | 7/2009 | Sexton et al. |
| 2009/0198189 A1 | 8/2009 | Simons et al. |
| 2009/0198215 A1 | 8/2009 | Chong et al. |
| 2009/0209883 A1 | 8/2009 | Higgins et al. |
| 2009/0215159 A1 | 8/2009 | Kirby |
| 2009/0216103 A1 | 8/2009 | Brister et al. |
| 2009/0216629 A1 | 8/2009 | James et al. |
| 2009/0264720 A1 | 10/2009 | Torjman et al. |
| 2009/0270792 A1 | 10/2009 | Lastovich et al. |
| 2009/0318779 A1 | 12/2009 | Tran |
| 2009/0318846 A1 | 12/2009 | Prausnitz et al. |
| 2010/0010374 A1 | 1/2010 | Escutia et al. |
| 2010/0021947 A1 | 1/2010 | Emery et al. |
| 2010/0030111 A1 | 2/2010 | Perriere |
| 2010/0042137 A1 | 2/2010 | Oronsky et al. |
| 2010/0049126 A1 | 2/2010 | Bronfeld et al. |
| 2010/0069726 A1 | 3/2010 | Levinson |
| 2010/0069730 A1 | 3/2010 | Bergstrom et al. |
| 2010/0094170 A1 | 4/2010 | Wilson et al. |
| 2010/0111970 A1 | 5/2010 | Pons et al. |
| 2010/0114014 A1 | 5/2010 | Roser |
| 2010/0121368 A1 | 5/2010 | Kim et al. |
| 2010/0147763 A1 | 6/2010 | Tsou et al. |
| 2010/0160894 A1 | 6/2010 | Julian et al. |
| 2010/0210970 A1 | 8/2010 | Horikawa et al. |
| 2010/0222703 A1 | 9/2010 | Takashima et al. |
| 2010/0234768 A1 | 9/2010 | Uchiyama et al. |
| 2010/0240079 A1 | 9/2010 | Jackson |
| 2010/0249560 A1 | 9/2010 | Levinson et al. |
| 2010/0256465 A1 | 10/2010 | Bernstein et al. |
| 2010/0256524 A1 | 10/2010 | Levinson et al. |
| 2010/0261988 A1 | 10/2010 | Tamir |
| 2010/0269837 A1 | 10/2010 | Levinson et al. |
| 2010/0272652 A1 | 10/2010 | Levinson et al. |
| 2010/0292191 A1 | 11/2010 | Mainx et al. |
| 2010/0318111 A1 | 12/2010 | Sarna et al. |
| 2010/0324449 A1 | 12/2010 | Rostaing et al. |
| 2010/0324451 A1 | 12/2010 | Ishibashi et al. |
| 2011/0003770 A1 | 1/2011 | Eek |
| 2011/0009847 A1 | 1/2011 | Levinson et al. |
| 2011/0034830 A1 | 2/2011 | Nakamura et al. |
| 2011/0040208 A1 | 2/2011 | Mcminn et al. |
| 2011/0040317 A1 | 2/2011 | Lee et al. |
| 2011/0105828 A1 | 5/2011 | Perless et al. |
| 2011/0105872 A1 | 5/2011 | Chickering et al. |
| 2011/0105951 A1 | 5/2011 | Bernstein et al. |
| 2011/0105952 A1 | 5/2011 | Bernstein et al. |
| 2011/0112384 A1 | 5/2011 | Eisenhardt et al. |
| 2011/0112438 A1 | 5/2011 | Radzuinas et al. |
| 2011/0125058 A1 | 5/2011 | Levinson et al. |
| 2011/0137203 A1 | 6/2011 | Nishiuchi et al. |
| 2011/0172508 A1 | 7/2011 | Chickering, III et al. |
| 2011/0172510 A1 | 7/2011 | Chickering, III et al. |
| 2011/0181410 A1 | 7/2011 | Levinson et al. |
| 2011/0245708 A1 | 10/2011 | Finkel et al. |
| 2011/0251562 A1 | 10/2011 | Chickering, III et al. |
| 2011/0276027 A1 | 11/2011 | Trautman et al. |
| 2011/0282173 A1 | 11/2011 | Fonduca et al. |
| 2011/0288389 A9 | 11/2011 | Levinson et al. |
| 2011/0306853 A1 | 12/2011 | Black et al. |
| 2012/0010529 A1 | 1/2012 | Chickering, III et al. |
| 2012/0016308 A1 | 1/2012 | Schott |
| 2012/0039809 A1 | 2/2012 | Levinson et al. |
| 2012/0041338 A1 | 2/2012 | Chickering et al. |
| 2012/0089050 A1 | 4/2012 | Fukuda |
| 2012/0123297 A1 | 5/2012 | Brancazio |
| 2012/0271125 A1 | 10/2012 | Bernstein et al. |
| 2012/0275955 A1 | 11/2012 | Haghgooie et al. |
| 2012/0277629 A1 | 11/2012 | Bernstein et al. |
| 2012/0277696 A1 | 11/2012 | Gonzalez-Zugasti et al. |
| 2012/0277697 A1 | 11/2012 | Haghgooie et al. |
| 2012/0315271 A1 | 12/2012 | Shelton et al. |
| 2013/0018279 A1 | 1/2013 | Plante et al. |
| 2013/0079666 A1 | 3/2013 | Gonzalez-Zugasti et al. |
| 2013/0081960 A1 | 4/2013 | Schott |
| 2013/0131741 A1 | 5/2013 | Kourtis et al. |
| 2013/0138058 A9 | 5/2013 | Chickering, III et al. |
| 2013/0158468 A1 | 6/2013 | Bernstein et al. |
| 2013/0158482 A1 | 6/2013 | Davis et al. |
| 2014/0336536 A1 | 11/2014 | Brancazio |
| 2015/0038876 A1 | 2/2015 | Gonzalez-Zugasti et al. |
| 2015/0057510 A1 | 2/2015 | Levinson et al. |
| 2015/0087944 A1 | 3/2015 | Levinson et al. |
| 2015/0278476 A1 | 10/2015 | Levinson et al. |
| 2015/0313522 A1 | 11/2015 | Bernstein et al. |
| 2015/0320349 A1 | 11/2015 | Haghgooie et al. |
| 2015/0342509 A1 | 12/2015 | Peeters et al. |
| 2016/0038068 A1 | 2/2016 | Chickering et al. |
| 2016/0262676 A1 | 9/2016 | Haghgooie et al. |
| 2017/0067803 A1 | 3/2017 | Jackson et al. |
| 2017/0120022 A1 | 5/2017 | Chickering et al. |
| 2017/0120023 A1 | 5/2017 | Davis et al. |
| 2017/0127990 A1 | 5/2017 | Levinson et al. |
| 2017/0127991 A1 | 5/2017 | Bernstein et al. |
| 2017/0172481 A1 | 6/2017 | Berthier et al. |
| 2017/0215790 A1 | 8/2017 | Levinson et al. |
| 2017/0224264 A1 | 8/2017 | Brancazio |
| 2017/0281852 A1 | 10/2017 | Bernstein et al. |
| 2018/0008183 A1 | 1/2018 | Chickering et al. |
| 2018/0132774 A1 | 5/2018 | Gonzalez-Zugasti et al. |
| 2018/0242890 A1 | 8/2018 | Chickering et al. |
| 2018/0310884 A1 | 11/2018 | Chickering et al. |
| 2018/0317829 A9 | 11/2018 | Gonzalez-Zugasti et al. |
| 2019/0023473 A1 | 1/2019 | Schott |
| 2019/0053740 A1 | 2/2019 | Davis et al. |
| 2019/0159709 A1 | 5/2019 | Barone et al. |
| 2019/0209820 A1 | 7/2019 | Chickering et al. |
| 2019/0216380 A1 | 7/2019 | Ivosevic et al. |
| 2019/0336058 A1 | 11/2019 | Haghgooie et al. |
| 2020/0015751 A9 | 1/2020 | Chickering et al. |

FOREIGN PATENT DOCUMENTS

| | | | |
|---|---|---|---|
| CN | | 2331315 Y | 8/1999 |
| CN | | 2462854 Y | 12/2001 |
| CN | | 2600055 Y | 1/2004 |
| CN | | 1499949 A | 5/2004 |
| CN | | 1501788 A | 6/2004 |
| CN | | 1524493 A | 9/2004 |
| CN | | 1551743 A | 12/2004 |
| CN | | 1753646 A | 3/2006 |
| CN | | 101248998 A | 8/2008 |
| CN | | 101347384 A | 1/2009 |
| CN | | 101678196 A | 3/2010 |
| DE | | 198 33 868 A1 | 5/2000 |
| DE | 20 2008 010918 U1 | | 12/2008 |
| EP | | 0 043 738 A2 | 1/1982 |
| EP | | 0 115 388 A1 | 8/1984 |
| EP | | 0 250 693 A1 | 1/1988 |
| EP | | 0 365 196 A2 | 4/1990 |
| EP | | 0 535 266 A1 | 4/1993 |
| EP | | 0 555 554 A1 | 8/1993 |
| EP | | 0 803 288 A2 | 10/1997 |
| EP | | 0 838 232 A2 | 4/1998 |
| EP | | 0 977 032 A1 | 2/2000 |
| EP | | 1 027 864 A1 | 8/2000 |
| EP | | 1 360 934 A1 | 11/2003 |
| EP | | 1 437 093 A1 | 7/2004 |
| EP | | 1 470 781 A2 | 10/2004 |
| EP | | 1 491 143 A1 | 12/2004 |
| EP | | 1 522 260 A1 | 4/2005 |
| EP | | 1 611 837 A2 | 1/2006 |
| EP | | 1 639 938 A1 | 3/2006 |
| EP | | 1 652 551 A2 | 5/2006 |
| EP | | 1 834 589 A2 | 9/2007 |
| EP | | 1 844 710 B1 | 10/2007 |
| EP | | 1 997 431 A1 | 12/2008 |
| EP | | 2 064 993 A1 | 6/2009 |

(56) References Cited

FOREIGN PATENT DOCUMENTS

| | | |
|---|---|---|
| EP | 2 077 128 A1 | 7/2009 |
| EP | 1187653 B1 | 3/2010 |
| EP | 2 701 601 A1 | 3/2014 |
| FR | 2929135 A1 | 10/2009 |
| GB | 2153223 A | 8/1985 |
| JP | 61-198061 A2 | 9/1986 |
| JP | 63-108264 A | 5/1988 |
| JP | 03-060645 A2 | 3/1991 |
| JP | 4-053536 A2 | 2/1992 |
| JP | 5-63506 A | 8/1993 |
| JP | 06-508286 T2 | 9/1994 |
| JP | 7-255706 A | 10/1995 |
| JP | H08-080291 A | 3/1996 |
| JP | 2000-116629 A | 4/2000 |
| JP | 2002-085384 | 3/2002 |
| JP | 2002-272710 A | 9/2002 |
| JP | 2002-532165 A1 | 10/2002 |
| JP | 2003-159238 A | 6/2003 |
| JP | 2004-8413 A | 1/2004 |
| JP | 2004-500948 | 1/2004 |
| JP | 2004-191336 A | 7/2004 |
| JP | 2004-532079 A | 10/2004 |
| JP | 2005-011364 A | 1/2005 |
| JP | 2005-522243 | 7/2005 |
| JP | 2005-211189 A | 8/2005 |
| JP | 2005-525141 A | 8/2005 |
| JP | 2005-245705 A | 9/2005 |
| JP | 2006-014789 | 1/2006 |
| JP | 2006-15148 A | 1/2006 |
| JP | 2006-109894 A | 4/2006 |
| JP | 2006-521555 A | 9/2006 |
| JP | 2006-280912 A | 10/2006 |
| JP | 2007-209549 A | 8/2007 |
| JP | 2007-209747 A | 8/2007 |
| JP | 2007-236686 | 9/2007 |
| JP | 2008-022988 A | 2/2008 |
| JP | 2008-54884 A | 3/2008 |
| JP | 2008-079853 A | 4/2008 |
| JP | 2008-99988 A | 5/2008 |
| JP | 2008-099992 A | 5/2008 |
| JP | 2008-534192 A | 8/2008 |
| JP | 2009-504273 A | 2/2009 |
| JP | 2009-509679 A | 3/2009 |
| JP | 2009-066385 A | 4/2009 |
| JP | 2009-078173 A | 4/2009 |
| JP | 2009-254899 A2 | 8/2009 |
| JP | 2014-516645 A | 7/2014 |
| KR | 2003-0061753 A | 7/2003 |
| WO | WO 92/02175 A1 | 2/1992 |
| WO | WO 92/04867 A1 | 4/1992 |
| WO | WO 93/00043 | 1/1993 |
| WO | WO 95/10223 A2 | 4/1995 |
| WO | WO 95/15783 A1 | 6/1995 |
| WO | WO 97/08987 A1 | 3/1997 |
| WO | WO 97/10745 A1 | 3/1997 |
| WO | WO 97/034587 A2 | 9/1997 |
| WO | WO 97/48442 A1 | 12/1997 |
| WO | WO 98/24366 A2 | 6/1998 |
| WO | WO 99/27852 A1 | 6/1999 |
| WO | WO 99/59657 A1 | 11/1999 |
| WO | WO 00/35357 A1 | 6/2000 |
| WO | WO 00/35530 A1 | 6/2000 |
| WO | WO 00/74763 A2 | 12/2000 |
| WO | WO 01/43643 A1 | 6/2001 |
| WO | WO 01/93946 A1 | 12/2001 |
| WO | WO 02/000101 A2 | 1/2002 |
| WO | WO 02/05890 A2 | 1/2002 |
| WO | WO 02/30301 A1 | 4/2002 |
| WO | WO 02/30506 A2 | 4/2002 |
| WO | WO 02/078533 A2 | 10/2002 |
| WO | WO 02/091922 A1 | 11/2002 |
| WO | WO 02/100253 A2 | 12/2002 |
| WO | WO 02/100460 A2 | 12/2002 |
| WO | WO 02/101359 A2 | 12/2002 |
| WO | WO 03/020134 A2 | 3/2003 |
| WO | WO 03/026611 A2 | 4/2003 |
| WO | WO 03/030984 A2 | 4/2003 |
| WO | WO 03/037407 A1 | 5/2003 |
| WO | WO 03/039632 A2 | 5/2003 |
| WO | WO 2003/037403 A1 | 5/2003 |
| WO | WO 03/070099 A1 | 8/2003 |
| WO | WO 03/082091 A2 | 10/2003 |
| WO | WO 03/088851 A1 | 10/2003 |
| WO | WO 2003/083469 A2 | 10/2003 |
| WO | WO 03/099123 A1 | 12/2003 |
| WO | WO 04/006982 A3 | 1/2004 |
| WO | WO 04/022133 A2 | 3/2004 |
| WO | WO 04/085995 A2 | 10/2004 |
| WO | WO 2005/000118 A1 | 1/2005 |
| WO | WO 2005/023111 A1 | 3/2005 |
| WO | WO 2005/025413 A2 | 3/2005 |
| WO | WO 2005/084534 A1 | 9/2005 |
| WO | WO 2005/095965 A1 | 10/2005 |
| WO | WO 2005/107594 A2 | 11/2005 |
| WO | WO 2005/123173 A1 | 12/2005 |
| WO | WO 2006/003403 A1 | 1/2006 |
| WO | WO 2006/019823 A2 | 2/2006 |
| WO | WO 2006/027586 A1 | 3/2006 |
| WO | WO 2006/050032 A2 | 5/2006 |
| WO | WO 2006/105968 A1 | 10/2006 |
| WO | WO 2006/111741 A1 | 10/2006 |
| WO | WO 2006/121510 A2 | 11/2006 |
| WO | WO 2006/128034 A1 | 11/2006 |
| WO | WO 2006/132504 A1 | 12/2006 |
| WO | WO 2007/002521 A2 | 1/2007 |
| WO | WO 2007/002522 A1 | 1/2007 |
| WO | WO 2007/021979 A2 | 2/2007 |
| WO | WO 2007/073870 A2 | 7/2007 |
| WO | WO 2007/079530 A1 | 7/2007 |
| WO | WO 2007/091671 A1 | 8/2007 |
| WO | WO 2007/092585 A2 | 8/2007 |
| WO | WO 2007/097754 A1 | 8/2007 |
| WO | WO 2007/108519 A1 | 9/2007 |
| WO | WO 2007/108987 A2 | 9/2007 |
| WO | WO 2007/115291 A2 | 10/2007 |
| WO | WO 2007/124411 A1 | 11/2007 |
| WO | WO 2008/016646 A2 | 2/2008 |
| WO | WO 2008/031035 A2 | 3/2008 |
| WO | WO 2008/043156 A1 | 4/2008 |
| WO | WO 2008/052034 A1 | 5/2008 |
| WO | WO 2008/062032 A1 | 5/2008 |
| WO | WO 2008/081444 A2 | 7/2008 |
| WO | WO 2008/109845 A2 | 9/2008 |
| WO | WO 2008/153930 A1 | 12/2008 |
| WO | WO 2009/004627 A3 | 1/2009 |
| WO | WO 2009/008267 A1 | 1/2009 |
| WO | WO 2009/011138 A1 | 1/2009 |
| WO | WO 2009/027950 A2 | 3/2009 |
| WO | WO 2009/055693 A2 | 4/2009 |
| WO | WO 2009/071775 A1 | 6/2009 |
| WO | WO 2009/101112 A1 | 8/2009 |
| WO | WO 2009/104765 A1 | 8/2009 |
| WO | WO 2009/107135 A2 | 9/2009 |
| WO | WO 2009/126653 A1 | 10/2009 |
| WO | WO 2009/145920 A1 | 12/2009 |
| WO | WO 2009/148624 A1 | 12/2009 |
| WO | WO 2009/149308 A2 | 12/2009 |
| WO | WO 2009/151421 A1 | 12/2009 |
| WO | WO 2010/011641 A2 | 1/2010 |
| WO | WO 2010/101620 A2 | 9/2010 |
| WO | WO 2010/101621 A1 | 9/2010 |
| WO | WO 2010/101625 A2 | 9/2010 |
| WO | WO 2010/101626 A1 | 9/2010 |
| WO | WO 2010/110916 A2 | 9/2010 |
| WO | WO 2010/120294 A1 | 10/2010 |
| WO | WO 2011/016019 A1 | 2/2011 |
| WO | WO 2011/053796 A2 | 5/2011 |
| WO | WO 2011/065972 A2 | 6/2011 |
| WO | WO 2011/088214 A2 | 7/2011 |
| WO | WO 2012/058337 A2 | 5/2012 |
| WO | WO 2012/064802 A1 | 5/2012 |
| WO | WO 2012/149134 A1 | 11/2012 |

(56) References Cited

FOREIGN PATENT DOCUMENTS

WO    WO 2014/160893 A2    10/2014
WO    WO 2017/191221 A1    11/2017

OTHER PUBLICATIONS

European Examination Report dated Apr. 3, 2017 in connection with Application No. EP 10708434.5.
Chinese Office Action dated Feb. 8, 2017 in connection with Application No. CN 201410543309.5.
Chinese Office Action dated Oct. 16, 2017 in connection with Application No. CN 201410543309.5.
Summons to Attend Oral Proceedings dated Jan. 4, 2018 for Application No. EP 10708432.9.
Japanese Notice of Reasons for Rejection dated Sep. 15, 2017 for Japanese Application No. 2016-240383.
Japanese Office Action dated Apr. 18, 2018 in connection with Japanese Application No. 2017-81597.
[No Author Listed], Whatman Neonatal Screening Cards-Capabilities. GE Healthcare. Dec. 2009; 12 pages. www.gelifesciences.com/whatman.
Fuhrer et al., Building a Smart Hospital using RFID technologies: Use Cases and Implementation. 2006; 14 pages.
U.S. Appl. No. 15/693,666, filed Sep. 1, 2017, Chickering et al.
U.S. Appl. No. 15/634,354, filed Jun. 27, 2017, Gonzalez-Zugasti et al.
U.S. Appl. No. 15/349,090, filed Nov. 11, 2016, Bernstein et al.
EP 10708432.9, Feb. 1, 2017, European Examination Report.
EP 10708434.5, Apr. 3, 2017, European Examination Report.
EP 10708432.9, Jan. 4, 2018, Summons to Attend Oral Proceedings.
JP 2016-240383, Sep. 15, 2017, Notice of Reasons for Rejection.
Japanese Office Action dated Apr. 18, 2018 in connection with Application No. JP 2017-81597.
European Office Action dated Feb. 26, 2015 for Application No. EP 10708432.9.
European Office Action dated Feb. 26, 2016 for Application No. EP 10708432.9.
European Office Action dated May 8, 2013 for Application No. 10708434.5.
European Office Action dated Nov. 26, 2013 for Application No. 10708432.9.
International Preliminary Report on Patentability dated Aug. 5, 2011 for International Application No. PCT/US2010/000624.
International Preliminary Report on Patentability dated Aug. 5, 2011 for International Application No. PCT/US2010/000631.
International Search Report and Written Opinion dated Aug. 18, 2010 for International Application No. PCT/US2010/000624.
International Search Report and Written Opinion dated Aug. 4, 2010 for International Application No. PCT/US2010/000631.
Invitation to Pay Additional Fees dated Jun. 2, 2010 for International Application No. PCT/U52010/000624.
Invitation to Pay Additional Fees dated Jun. 9, 2010 for International Application No. PCT/U52010/000631.
Invitation to Restrict or Pay Additional Fees dated Jun. 20, 2011 for International Application No. PCT/US2010/000624.
Invitation to Restrict or Pay Additional Fees dated Jun. 20, 2011 for International Application No. PCT/US2010/000631.
Chinese Office Action and English translation thereof dated Jun. 4, 2013 for Application No. 201080017375.9.
Chinese Office Action dated Nov. 28, 2013 for Application No. 201080017376.3 and English translation thereof.
Chinese Office Action and English translation thereof dated Jan. 16, 2014 for Application No. 201080017375.9.
Chinese Office Action dated Oct. 20, 2014 for Application No. CN 201080017376.3.
Chinese Office Action dated Jun. 30, 2015 for Application No. 201080017376.3.
Japanese Office Action dated May 27, 2014 for Application No. 2011-552935.
Japanese Office Action dated May 27, 2014 for Application No. 2011-552936.
Japanese Office Action dated Apr. 27, 2015 for Application No. 2011-552935.
Japanese Office Action dated Apr. 27, 2015 for Application No. 2011-552936.
Japanese Office Action dated Dec. 15, 2015 for Application No. JP 2011-552935.
Japanese Office Action dated Dec. 15, 2015 for Application No. JP 2011-552936.
[No Author Listed] Greiner Bio-One Preanalytics Catalogue. www.gbo.com/preanalytics. Feb. 2012. 76 pages.
[No Author Listed] Safe-T-Fill®: 100% Plastic Capillary Blood Collection Systems. RAM Scientific. [Month of publication not listed on copy] 2003. Last accessed Jun. 28, 2012 at http//www.ramsci.com.
[No Author Listed] Sof-Tact Manual. Date Unknown. 57 pages. (After reasonable inquiry, the undersigned believed this manual was available beginning 2001, but cannot determine the exact date of this publication.The year of publication is sufficiently earlier than the effective U.S. filing date and priority date so that the particular month and year of publication is not an issue. See MPEP 609.04(a).).
Angell et al., Silicon Micromechanical Devices. Scientific American. Apr. 1983;248:44-55.
Aungst et al., Contributions of drug solubilization, partitioning, barrier disruption, and solvent permeation to the enhancement of skin permeation of various compounds with fatty acids and amines. Pharm Res. Jul. 1990;7(7):712-8.
Baroli, Penetration of metallic nanoparticles in human full-thickness skin. J. Ind. Derm. 2007;127:1701-12. Epub Mar. 22, 2007.
Bina et al., Clinical impact of prandial state, exercise, and site preparation on the equivalence of alternative-site blood glucose testing. Diabetes Care. Apr. 2003;26(4):981-5.
Brown, Encapsulation of glucose oxidase and an oxygen-quenched fluorophore in polyelectrolyte-coated calcium alginate microspheres as optical glucose sensor systems. Biosens Bioelec. 2005;21:212-16. Epub Sep. 17, 2004.
Cormier et al., Transdermal delivery of desmopressin using a coated microneedle array patch system. J Control Release. Jul. 7, 2004;97(3):503-11.
Duffy et al., Rapid Prototyping of Microfluidic Systems and Polydimethylsiloxane. Anal Chem. Dec. 1, 1998;70:4974-84.
Elias, The Microscopic Structure of the Epidermis and Its Derivatives. In: Percutaneous Absorption—Mechanisms—Methodology. Bronaugh et al., eds. Marcell Dekker. 1989;3-12. (The year of publication is sufficiently earlier than the effective U.S. filing date and any foreign priority date so that the particular month of publication is not in issue. See MPEP 609.04(a)).
Fineberg et al., Use of an automated device for alternative site blood glucose monitoring. Diabetes Care. Jul. 2001;24(7):1217-20.
Gomes et al., Evaluation of nanoparticles loaded with benzopsoralen in rat peritoneal exudate cells. Int J Pharm. Mar. 6, 2007;332(1-2):153-60. Epub Sep. 27, 2006.
Kost et al., Chapter 4. Ultrasound-Mediated Transdermal Drug Delivery. In: Topical Drug Bioavailability Bioequivalance, and Penetration. Shah et al., eds. Plennum, NY. 1993:91-104. (The year of publication is sufficiently earlier than the effective U.S. filing date and any foreign priority date so that the particular month of publication is not in issue. See MPEP 609.04(a)).
Matriano et al., Macroflux microprojection array patch technology: a new and efficient approach for intracutaneous immunization Pharm Res. Jan. 2002;19(1):63-70.
McShane, Microcapsules as 'smart tattoo' glucose sensors: engineering systems with enzymes and glucose binding sensing elements, *Top Fluor. Spec.*, 2006, vol. 11, *Glc. Sens.*, p. 131-163. (The year of publication is sufficiently earlier than the effective U.S. filing date and any foreign priority date so that the particular month of publication is not in issue. See MPEP 609.04(a)).
Mitragotri et al., Sonophoresis: Enhanced Transdermal Drug Delivery by Application of Ultrasound. In: Encl. of Pharm. Tech, vol. 14, Swarbrick, J., Boylan, J., (Eds.), vol. 14, 103-122, 1996. (After

(56) References Cited

OTHER PUBLICATIONS reasonable inquiry, the undersigned believes this was available in 1996, but cannot determine the exact date of this publication. The year of publication is sufficiently earlier than the effective U.S. filing date and priority date so that the particular month and year of publication is not in issue. See MPEP 609.04(a).).
Rousche et al., A method for pneumatically inserting an array of penetrating electrodes into cortical tissue. Annals of Biomedical Engineering. Jul. 1992;20(4):413-22.
Rousche et al., A System for Impact Insertion of a 100 Electrode Array into Cortical Tissue. Annual Intl Conf IEEE Engineer Med Biol Soc. 1990;12(2):O494-95. (The year of publication is sufficiently earlier than the effective U.S. filing date and ay foreign priority date so that the particular month of publication is not in issue. See MPEP 609.04(a)).
Rouse, Effects of mechanical flexion on the penetration of fullerene amino acid-derivatized peptide nanoparticles through skin. Nano Lett. Jan. 2007;7(1):155-60. Epub Dec. 6, 2006.
Suk et al., Gene delivery to differentiated neurotypic cells with RGD and HIV Tat peptide functionalized polymeric nanoparticles. Biomaterials. Oct. 2006;27(29):5143-50.
Uhrich, Polymeric systems for controlled drug release. Chem. Rev. 1999;99:3181-98. Epub Oct. 26, 1999.
Verbaan et al., Improved piercing of microneedle arrays in dermatomed human skin by an impact insertion method. J Control Release. May 22, 2008;128(1):80-8. Epub Feb. 26, 2008.
Whitesides et al., Soft lithography in biology and biochemistry. Annu Rev Biomed Eng. Aug. 2001;3:335-73.
Xia et al., Soft Lithography. Ann Rev Mater Sci. Aug. 1998;28:153-84.
European Examination Report dated Jun. 21, 2016 for Application No. 10708434.5.
Chinese Office Action dated Mar. 24, 2016 and English translation thereof for Application No. 201410543309.5.
Japanese Office Action dated Apr. 25, 2016 and English translation thereof for Application No. 2011-552936.
Japanese Office Action dated Jun. 10, 2016 and English translation thereof for Application No. 2011-552935.
U.S. Appl. No. 14/797,421, filed Jul. 13, 2015, Bernstein et al.
U.S. Appl. No. 15/281,626, filed Sep. 30, 2016, Chickering et al.
U.S. Appl. No. 12/915,789, filed Oct. 29, 2010, Bernstein et al.
U.S. Appl. No. 12/915,820, filed Oct. 29, 2010, Bernstein et al.
U.S. Appl. No. 14/682,478, filed Apr. 9, 2015, Levinson et al.
U.S. Appl. No. 14/513,327, filed Oct. 14, 2014, Levinson et al.
U.S. Appl. No. 13/006,177, filed Jan. 13, 2011, Chickering et al.
U.S. Appl. No. 14/527,923, filed Oct. 30, 2014, Levinson et al.
U.S. Appl. No. 13/183,789, filed Jul. 15, 2011, Schott.
U.S. Appl. No. 15/231,881, filed Aug. 9, 2016, Chickering et al.
U.S. Appl. No. 13/006,165, filed Jan. 13, 2011, Chickering et al.
U.S. Appl. No. 14/328,892, filed Jul. 11, 2014, Gonzalez-Zugasti et al.
U.S. Appl. No. 14/805,675, filed Jul. 22, 2015, Haghgooie et al.
U.S. Appl. No. 15/299,591, filed Oct. 21, 2016, Bernstein et al.
EP 10708434.5, Jun. 21, 2016, European Examination Report.
Chinese Office Action dated Mar. 24, 2016 for Application No. 201410543309.5.
Japanese Office Action dated Apr. 25, 2016 for Application No. 2011-552936.
Japanese Office Action dated Jun. 10, 2016 for Application No. 2011-552935.
Extended European Search Report dated Oct. 9, 2019 in connection with Application No. EP 19150218.6.
European Notice of Opposition dated Oct. 15, 2019 in connection with European Application No. 10708434.5.
[No Author Listed] Air-Tite Products Co., Inc.—Luer Slip. Oct. 14, 2008. Retrieved from the Internet: https://web.archive.org/web/20081014224752/https://www.air-tite-shop.com/c-6-luer-slip.aspx on Aug. 28, 2019. 2 pages.
[No Author Listed] Air-Tite Products Co., Inc.—Luer Lock. Oct. 14, 2008. Retrieved from the Internet: https://web.archive.org/web/20081023203858/https://www.air-tite-shop.com/c-7-luer-lock.aspx on Aug. 28, 2019. 2 pages.
Matsuura et al., Development of a blood extraction device for a miniature SMBG system. Dec. 27, 2007. Proceedings vol. 6799, BioMEMS and Nanotechnology III; 67990N (2007) https://doi.org/10.1117/12.758869. Event: SPIE Microelectronics, MEMS, and Nanotechnology, 2007, Canberra, ACT, Australia.
U.S. Appl. No. 15/916,330, filed Mar. 9, 2018, Davis et al.
U.S. Appl. No. 15/828,908, filed Dec. 1, 2017, Chickering et al.
U.S. Appl. No. 15/285,034, filed Oct. 4, 2016, Levinson et al.
U.S. Appl. No. 15/899,613, filed Feb. 20, 2018, Schott.
U.S. Appl. No. 16/048,722, filed Jul. 30, 2018, Chickering et al.
U.S. Appl. No. 15/290,217, filed Oct. 11, 2016, Levinson et al.
U.S. Appl. No. 15/297,253, filed Oct. 19, 2016, Brancazio.
U.S. Appl. No. 16/806,426, filed Mar. 2, 2020, Chickering et al.
U.S. Appl. No. 17/014,022, filed Sep. 8, 2020, Gonzalez-Zugasti et al.
U.S. Appl. No. 14/987,973, filed Jan. 5, 2016, Haghgooie et al.
U.S. Appl. No. 17/064,618, filed Oct. 7, 2020, Haghgooie et al.
U.S. Appl. No. 16/218,441, filed Dec. 12, 2018, Haghgooie et al.
U.S. Appl. No. 16/705,286, filed Dec. 6, 2019, Bernstein et al.
U.S. Appl. No. 15/156,386, filed May 17, 2016, Bernstein et al.
U.S. Appl. No. 16/321,123, filed Jan. 28, 2019. Barone et al.

\* cited by examiner

TECHNIQUES AND DEVICES ASSOCIATED WITH BLOOD SAMPLING

RELATED APPLICATIONS

This application is a continuation of U.S. patent application Ser. No. 14/527,923, filed Oct. 30, 2014, entitled "Techniques and Devices Associated with Blood Sampling," by Levinson, et al., which is a continuation of U.S. patent application Ser. No. 12/716,226, filed Mar. 2, 2010, entitled "Techniques and Devices Associated with Blood Sampling," by Levinson, et al., which claims the benefit of U.S. Provisional Patent Application Ser. No. 61/163,710, filed Mar. 26, 2009, entitled "Systems and Methods for Creating and Using Suction Blisters or Other Pooled Regions of Fluid within the Skin," by Levinson, et al.; U.S. Provisional Patent Application Ser. No. 61/156,632, filed Mar. 2, 2009, entitled "Oxygen Sensor," by Levinson, et al.; U.S. Provisional Patent Application Ser. No. 61/269,436, filed Jun. 24, 2009, entitled "Devices and Techniques associated with Diagnostics, Therapies, and Other Applications, Including Skin-Associated Applications," by Levinson, et al.; U.S. Provisional Patent Application Ser. No. 61/257,731, filed Nov. 3, 2009, entitled "Devices and Techniques associated with Diagnostics, Therapies, and Other Applications, Including Skin-Associated Applications," by Bernstein, et al.; and U.S. Provisional Patent Application Ser. No. 61/294,543, filed Jan. 13, 2010, entitled "Blood Sampling Device and Method," by Levinson, et al. Each of the above is incorporated herein by reference.

FIELD OF INVENTION

The present invention generally relates to interstitial and other bodily fluids for use in analyzing a condition of a subject or treating a subject. The present invention also relates to systems and methods for delivering and/or withdrawing fluid from subjects, e.g., through the skin.

BACKGROUND

A variety of techniques and methods exist for sensing and responding to conditions to which a subject is exposed, including sensing of physiological conditions of a mammal and/or a surrounding environment. Other techniques exist for delivering and/or withdrawing a fluid from a mammal, such as blood. While many such techniques are suitable for various purposes, techniques that have one or more features such as added simplicity and flexibility of use would be advantageous.

SUMMARY OF THE INVENTION

The present invention, in some aspects, generally relates to interstitial and other bodily fluids (e.g., blood) for use in analyzing a condition of a subject or treating a subject. In some cases, the present invention also relates to systems and methods for delivering and/or withdrawing fluid from subjects, e.g., through the skin. The subject matter of the present invention involves, in some cases, interrelated products, alternative solutions to a particular problem, and/or a plurality of different uses of one or more systems and/or articles.

The present invention is directed to a device for analysis of an extractable medium from a subject in one aspect. In one set of embodiments, the device includes a support structure, means associated with the support structure for accessing the extractable medium from and/or through the skin of the subject at an access site, and a pressure regulator supported by the support structure, able to create a pressure differential across the skin at at least a portion of the access site. In some cases, the device may also include a sensor supported by the support structure, for determining at least one condition of the extractable medium from the subject, and optionally a signal generator supported by the support structure, for generating a signal relating to the condition of the medium determined by the sensor. In some embodiments, the support structure is constructed and arranged to be positioned proximate the skin of the subject.

In another set of embodiments, the device includes a support structure constructed and arranged to be positioned proximate the skin of the subject, a fluid transporter for accessing the extractable medium from and/or through the skin of the subject at an access site, a pressure regulator supported by the support structure, able to create a pressure differential across the skin at at least a portion of the access site, a sensor supported by the support structure for determining at least one condition of the extractable medium from the subject, and a signal generator supported by the support structure for generating a signal relating to the condition of the medium determined by the sensor.

The device, according to yet another set of embodiments, includes means for accessing the extractable medium from and/or through the skin of the subject at an access site, a pressure regulator able to create a pressure differential across the skin at at least a portion of the access site, a sensor for determining at least one condition of the extractable medium from the subject, and a signal generator for generating a signal relating to the condition of the medium determined by the sensor.

In another set of embodiments, the device includes means for accessing the extractable medium from skin and/or from beneath the skin of the subject at an access site, a pressure differential chamber able to create a pressure differential across the skin in at least a portion of the access site in the absence of a piston pump associated with the chamber, a sensor for determining at least one condition of the extractable medium from the subject, and a signal generator for generating a signal relating to the condition of the medium determined by the sensor.

The invention, in another aspect, is generally directed to a device. According to one set of embodiments, the device can be applied or is applicable to the skin for determining an analyte in a subject. The device, in one embodiment, includes a first portion able to create a pooled region of fluid within the skin of a subject, and a second portion able to determine fluid of the pooled region of fluid. In another set of embodiments, the device includes a first portion able to create a pooled region of fluid within the skin of a subject, and a microfluidic channel in fluidic communication with the first portion.

The device, in yet another set of embodiments, is applicable to a site proximate the skin of a subject. In some cases, the device is able to determine a physical condition of a subject and produces a signal related to the condition. In one embodiment, the signal is not readily understandable by the subject.

The device, in yet another set of embodiments, is a device applicable to a site proximate the skin of a subject. In some embodiments, the device is able to determine a physical condition of the subject. In one embodiment, the device comprises an agent that reacts or interacts with an analyte to be detected and generates a signal that can be detected visually, by feel, by smell, or by taste. In some cases, the agent that reacts with or interacts with an analyte and the signaling agent can be the same or different. In certain cases, the signal can vary as a function of an attribute of the analyte, producing a signal that can be analyzed qualitatively. In some instances, the device acquires fluid from the subject and transports the fluid from a site of acquisition to a site of analysis for reaction.

In some cases, the device includes a first component and a second component connected to the first component for application to the site and separable from the first component after application to the site. In some instances, the first component can be activated to acquire a bodily fluid of the subject, and the second component comprises an agent that reacts or interacts with an analyte to be detected and generates a signal that can be detected visually, by feel, by smell, or by taste.

The device, in accordance with another set of embodiments, includes an agent that reacts or interacts with an analyte in saliva of the subject to generate a signal. In still another set of embodiments, the device comprises an agent that reacts or interacts with an analyte to be detected to generate a signal that can be detected visually, by feel, by smell, or by taste. In some cases, the device comprises a membrane comprising the agent that participates in generation of the signal. The membrane, in some embodiments, may be selective to one or more of passage of an analyte and/or an analyte indicator, and reaction with an analyte and/or an analyte indicator.

According to still another set of embodiments, the device is a device for withdrawing blood from the skin and/or from beneath the skin of a subject. In some embodiments, the device comprises a fluid transporter, a vacuum chamber having an internal pressure less than atmospheric pressure before blood is withdrawn into the device, and a storage chamber, separate from the vacuum chamber, for receiving blood withdrawn from the subject through the fluid transporter when a negative pressure is applied to the skin of the subject. The device, in certain embodiments, includes at least 6 microneedles, and a storage chamber for receiving blood withdrawn from the subject, the storage chamber having an internal pressure less than atmospheric pressure prior to receiving blood.

The device, in some embodiments, includes a fluid transporter, a first storage chamber for receiving blood withdrawn from the subject through the fluid transporter, the storage chamber having an internal pressure less than atmospheric pressure prior to receiving blood, and a reaction entity contained within the first storage chamber able to react with an analyte contained within the blood. In some instances, a product of the reaction entity with the analyte is determinable. According to still other embodiments, the device includes a fluid transporter, a storage chamber for receiving blood withdrawn from the subject through the fluid transporter, and a potassium sensor able to determine potassium ions within blood contained within the device. In some cases, the storage chamber has an internal pressure less than atmospheric pressure prior to receiving blood.

In yet another set of embodiments, the device includes a fluid transporter, a storage chamber for receiving blood withdrawn from the subject through the fluid transporter, and a flow controller able to control blood flow into the storage chamber. In some cases, the storage chamber has an internal pressure less than atmospheric pressure prior to receiving blood.

In another aspect, the present invention is directed to a method. The method, in one set of embodiments, includes acts of causing formation of a pooled region of fluid between the dermis and epidermis of the skin of a subject, and delivering an agent into the pooled region of fluid for indication of a past, present and/or future condition of the subject. The method, according to another set of embodiments, includes acts of causing formation of a pooled region of fluid between the dermis and epidermis of the skin of a subject, removing at least a portion of the fluid from the pooled region, and analyzing at least a portion of the removed fluid thereby determining a past, present and/or future condition of the subject by exposing the fluid to an agent.

The method, according to another set of embodiments, includes acts of providing a device at a site proximate the skin of a subject, acquiring a representation of the signal, and transporting the representation of the signal to an entity that analyzes the representation. In some cases, the device can determine a physical condition of a subject and produces a signal related to the condition. In yet another set of embodiments, the method includes an act of applying, proximate the skin of a subject in need of emergency care, a device comprising a reactive agent that reacts or interacts with an analyte to generate a signal indicative of a condition of the subject. The method, in still another set of embodiments, includes an act of applying, to a solution containing a plurality of first particles of a first color and a plurality of second particles of a second color, an electric field and/or a magnetic field sufficient to cause a change in color of the solution. According to yet another set of embodiments, the method includes an act of determining a characteristic of a sample by visualizing a color change effected by a change in population of particles of different color upon preferential binding of particles of one color to a component of the sample via a binding partner.

The method, in one set of embodiments, includes acts of exposing, to a sample, a population of particles including at least a first sub-population having a first determinable characteristic and a second sub-population having a second determinable characteristic, allowing at least some particles of the first sub-population of particles to bind a component of the sample via a binding partner, separating the particles bound to the component from those not bound, and determining a characteristic of the sample by determining the separation. In some embodiments, the second sub-population of particles remains essentially unbound to the component, such that the ratio of the number of particles from the first sub-population bound to the component, to the number of particles from the second sub-population bound to the component, is at least 5:1.

In another set of embodiments, the method includes an act of providing a plurality of analysis sites proximate the skin of a subject, including at least a first analysis site that generates a first signal related to a first physical condition of the subject and a second analysis site that generates a second signal related to a second physical condition of the subject. The method, in accordance with still another set of embodiments, includes an act of providing a reaction site proximate the skin of a subject comprising a reactive agent that reacts or interacts with an analyte to generate an signal in the form of an icon.

In yet another set of embodiments, the method is a method for analyzing an extractable medium from a subject. In some embodiments, the method includes acts of positioning an analysis device comprising a pathway adjacent the skin of the subject and, while the device is adjacent the skin, activating an access component of the device to connect the extractable medium with the pathway of the device, activating a pressure controller of the device to urge the extractable medium into the device via the pathway, exposing the medium to a sensor of the device and determining at least one condition of the extractable medium from the subject, and generating a signal relating to the condition of the medium determined by the sensor.

In another aspect, the present invention is directed to a method of making one or more of the embodiments described herein. In another aspect, the present invention is directed to a method of using one or more of the embodiments described herein.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

The present invention generally relates to devices and techniques associated with diagnostics, therapies, and other applications, including skin-associated applications, for example, devices for delivering and/or withdrawing fluid from subjects, e.g., through the skin. In some embodiments, the device includes a system for accessing an extractable medium from and/or through the skin of the subject at an access site, and a pressure regulator supported by a support structure, able to create a pressure differential across the skin at at least a portion of the access site. The device may also include, in some cases, a sensor supported by the support structure for determining at least one condition of the extractable medium from the subject, and optionally a signal generator supported by the support structure for generating a signal relating to the condition of the medium determined by the sensor.

Figure 9A:
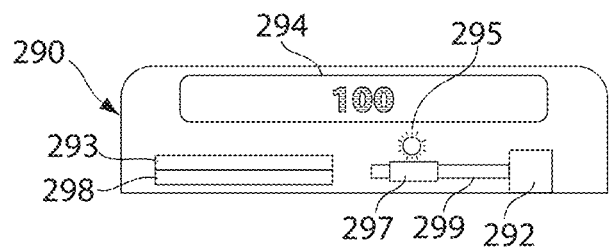
FIG. 9A-9B illustrate devices according to certain embodiments of the invention.

Non-limiting examples of various devices of the invention are shown in FIG. 9. In FIG. 9A, device 290 is used for withdrawing a fluid from a subject when the device is placed on the skin of a subject. Device 290 includes sensor 295 and fluid transporter 292, e.g., a needle, a microneedle, etc., as discussed herein. In fluidic communication with fluid transporter 292 via fluidic channel 299 is sensing chamber 297. In one embodiment, sensing chamber 297 may contain agents such as particles, enzymes, dyes, etc., for analyzing bodily fluids, such as interstitial fluid or blood. In some cases, fluid may be withdrawn using fluid transporter 292 by a vacuum, for example, a self-contained vacuum contained within device 290. Optionally, device 290 also contains a display 294 and associated electronics 293, batteries or other power supplies, etc., which may be used to display sensor readings obtained via sensor 295. In addition, device 290 may also optionally contain memory 298, transmitters for transmitting a signal indicative of sensor 295 to a receiver, etc.

As used herein, "fluid transporter" is any component or combination of components that facilitates movement of a fluid from one portion of the device to another. For example, at or near the skin, a fluid transporter can be a hollow needle when a hollow needle is used or, if a solid needle is used, then if fluid migrates along the needle due to surface forces (e.g., capillary action), then the solid needle can be a fluid transporter. If fluid (e.g. blood or interstitial fluid) partially or fully fills an enclosure surrounding a needle after puncture of skin (whether the needle is or is not withdrawn from the skin after puncture), then the enclosure can define a fluid transporter. Other components including partially or fully enclosed channels, microfluidic channels, tubes, wicking members, vacuum containers, etc. can be fluid transporters In the example shown in FIG. 9A, device 290 may contain a vacuum source (not shown) that is self-contained within device 290, although in other embodiments, the vacuum source may be external to device 290. (In still other instances, other systems may be used to deliver and/or withdraw fluid from the skin, as is discussed herein.) In one embodiment, after being placed on the skin of a subject, the skin may be drawn upward into a recess containing fluid transporter 292, for example, upon exposure to the vacuum source. Access to the vacuum source may be controlled by any suitable method, e.g., by piercing a seal or a septum; by opening a valve or moving a gate, etc. For instance, upon activation of device 290, e.g., by the subject, remotely, automatically, etc., the vacuum source may be put into fluidic communication with the recess such that skin is drawn into the recess containing fluid transporter 292 due to the vacuum. Skin drawn into the recess may come into contact with fluid transporter 292 (e.g., solid or hollow needles), which may, in some cases, pierce the skin and allow a fluid to be delivered and/or withdrawn from the skin.

In another embodiment, fluid transporter 292 may be actuated and moved downward to come into contact with the skin, and optionally retracted after use.

Figure 9B:
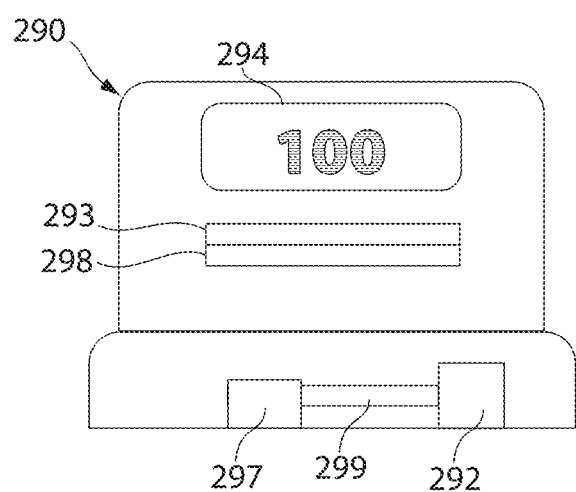

Another non-limiting example of a device is shown in FIG. 9B. This figure illustrates a device useful for delivering a fluid to the subject. Device 290 in this figure includes fluid transporter 292, e.g., a needle, a microneedle, etc., as discussed herein. In fluidic communication with fluid transporter 292 via fluidic channel 299 is chamber 297, which may contain a drug or other agent to be delivered to the subject. In some cases, fluid may be delivered with a pressure controller, and/or withdrawn using fluid transporter 292 by a vacuum, for example, a self-contained vacuum contained within device 290. For instance, upon creating a vacuum, skin may be drawn up towards fluid transporter 292, and fluid transporter 292 may pierce the skin. Fluid from chamber 297 can then be delivered into the skin through fluid channel 299 and fluid transporter 292. Optionally, device 290 also contains a display 294 and associated electronics 293, batteries or other power supplies, etc., which may be used control delivery of fluid to the skin. In addition, device 290 may also optionally contain memory 298, transmitters for transmitting a signal indicative of device 290 or fluid delivery to a receiver, etc.

Figure 10A:
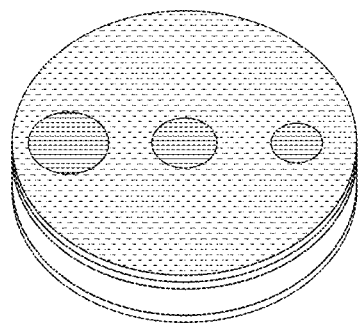
FIGS. 10A-10B illustrate devices according to various embodiments of the invention.
Figure 10B:
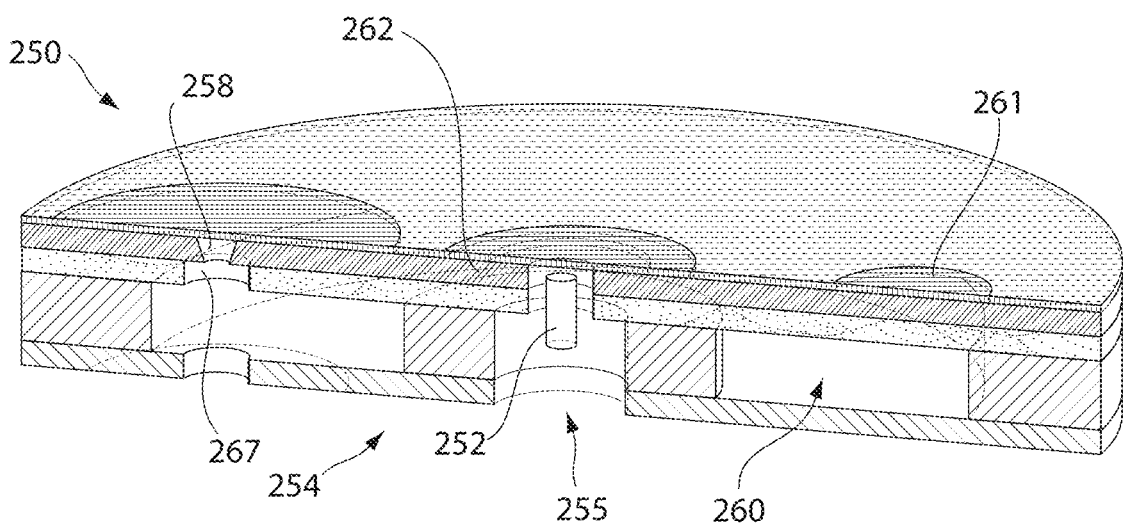

Yet another non-limiting example of a device of the invention is shown in FIG. 10. FIG. 10A illustrates a view of the device (with the cover removed), while FIG. 10B schematically illustrates the device in cross-section. In FIG. 10B, device 250 includes a needle 252 contained within a recess 255. Needle 252 may be solid or hollow, depending on the embodiment. Device 250 also includes a self-contained vacuum chamber 260, which wraps around the central portion of the device where needle 252 and recess 255 are located. A channel 262 connects vacuum chamber 260 with recess 255, separated by foil or a membrane 267. Also shown in device 250 is button 258. When pushed, button 258 breaks foil 267, thereby connecting vacuum chamber 250 with recess 255, creating a vacuum in recess 255. The vacuum may be used, for example, to draw skin into recess 255, preferably such that it contacts needle 252 and pierces the surface, thereby gaining access to an internal fluid. The fluid may be controlled, for example, by controlling the size of needle 252, and thereby the depth of penetration. For example, the penetration may be limited to the epidermis, e.g., to collect interstitial fluid, or to the dermis, e.g., to collect blood. In some cases, the vacuum may also be used to at least partially secure device 250 on the surface of the skin, and/or to assist in the withdrawal of fluid from the skin. For instance, fluid may flow into channel 262 under action of the vacuum, and optionally to sensor 261, e.g., for detection of an analyte contained within the fluid. For instance, sensor 261 may produce a color change if an analyte is present, or otherwise produce a detectable signal.

Other components may be added to the example of the device illustrated in FIG. 10, in some embodiments of the invention. For example, device 250 may contain a cover, displays, ports, transmitters, sensors, microfluidic channels, chambers, fluid channels, and/or various electronics, e.g., to control or monitor fluid transport into or out of device 250, to determine an analyte present within a fluid delivered and/or withdrawn from the skin, to determine the status of the device, to report or transmit information regarding the device and/or analytes, or the like, as is discussed in more detail herein. As another example, device 250 may contain an adhesive, e.g., on surface 254, for adhesion of the device to the skin.

Figure 11A:
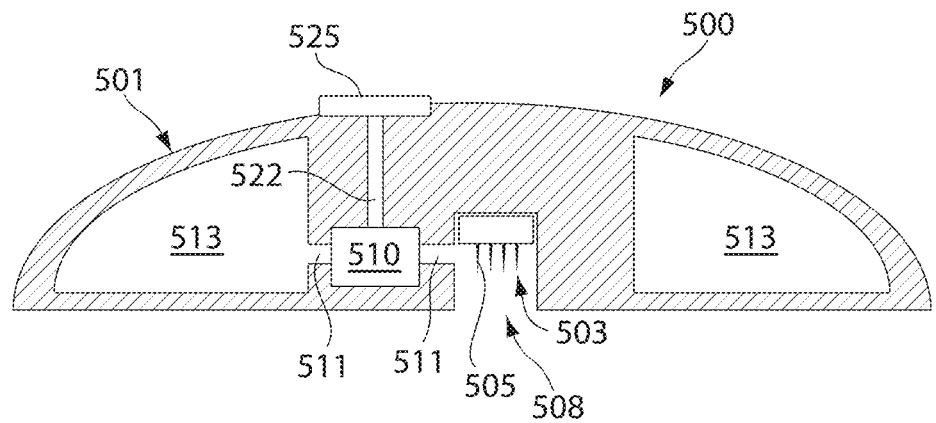
FIG. 11A illustrates a device according to still another embodiment of the invention.

Yet another non-limiting example is illustrated with reference to FIG. 11A. In this example, device 500 includes a support structure 501, and an associated fluid transporter system 503. Fluid transporter system 503 includes a plurality of needles or microneedles 505, although other fluid transporters as discussed herein may also be used. Also shown in FIG. 11A is sensor 510, connected via channels 511 to recess 508 containing needles or microneedles 505. Chamber 513 may be a self-contained vacuum chamber, and chamber 513 may be in fluidic communication with recess 508 via channel 511, for example, as controlled by a controller or an actuator (not shown). In this figure, device 500 also contains display 525, which is connected to sensor 510 via electrical connection 522. As an example of use of device 500, when fluid is drawn from the skin (e.g., blood, interstitial fluid, etc.), the fluid may flow through channel 511 to be determined by sensor 510, e.g., due to action of the vacuum from vacuum chamber 513. In some cases, the vacuum is used, for example, to draw skin into recess 508, e.g., such that it contacts needles or microneedles 505 and pierces the surface of the skin to gain access to a fluid internal of the subject, such as blood or interstitial fluid, etc. The fluid may be controlled, for example, by controlling the size of needle 505, and thereby the depth of penetration. For instance, the penetration may be limited to the epidermis, e.g., to collect interstitial fluid, or to the dermis, e.g., to collect blood. Upon determination of the fluid and/or an analyte present or suspected to be present within the fluid, a microprocessor or other controller may display a suitable signal on display 525. As is discussed below, a display is shown in this figure by way of example only; in other embodiments, no display may be present, or other signals may be used, for example, lights, smell, sound, feel, taste, or the like. In some cases, more than one fluid transporter system may be present within the device. For instance, the device may be able to be used repeatedly, and/or the device may be able to deliver and/or withdraw fluid at more than one location on a subject, e.g., sequentially and/or simultaneously. In some cases, the device may be able to simultaneously deliver and withdraw fluid to and from a subject. A non-limiting example of a device having more than one fluid transporter system is illustrated with reference to FIG. 11C. In this example, device 500 contains a plurality of structures such as those described herein for delivering to and/or withdrawing fluid from a subject. For example, device 500 in this example contains 3 such units, although any number of units are possible in other embodiments. In this example, device 500 contains three such fluid transporter systems 575. Each of these fluid transporter systems may independently have the same or different structures, depending on the particular application, and they may have structures such as those described herein.

As noted, the invention in one set of embodiments involves determination of a condition of a subject. In such a case, bodily fluid and/or material associated with the skin may be analyzed, for instance, as an indication of a past, present and/or future condition of the subject, or to determine conditions that are external to the subject. Determination may occur, for instance, visually, tactilely, by odor, via instrumentation, etc. Other aspects of the invention are directed to devices able to create pooled regions within the skin, and are optionally able to remove fluid from the pooled region and/or add material to the pooled region. Still other aspects of the invention are generally directed to making or using such devices, methods of promoting the making or use of such devices, and the like.

Agents such as particles can be used to analyze bodily fluids, such as interstitial fluid or blood. Other suitable agents include enzymes, dyes, nucleic acids, antibodies, oligonucleotides, reaction entities, or the like, e.g., as discussed herein. The interstitial fluids may be accessed or collected using a suction blister device in certain embodiments, or using other techniques such as those described below. The agent may be any agent able to determine an analyte. For example, the agent may be an antibody which is labeled with a colorimetric, gold, or fluorescent label, which binds analyte, producing a color change which is proportional to the amount of analyte. In some cases, more than one agent may be used. For example, a first agent may react with an analyte and the second agent may be used to create a determinable signal, for instance, visual, tactile, smell, taste, shape change, or the like. Combinations of these can also be utilized in some cases. For example, an antibody to a carcinoembryonic antigen ("CEA") and an antibody to a prostate specific antigen ("PSA") may be used to monitor for cancer of either origin; the antibodies may be used to produce various colors upon detection of their corresponding analytes, for instance, the colors may be yellow for CEA and blue for PSA, resulting in green if both are elevated.

In one set of embodiments, one or more of the agents may be particles, such as anisotropic particles or colloids. Accordingly, in the descriptions that follow, it should be understood that "particles" are described by way of example only, and in other embodiments, other agents, such as antibodies, may also be used, in addition and/or instead of particles.

In other embodiments, fluid may be delivered to the subject, and such fluids may contain materials useful for delivery, e.g., forming at least a portion of the fluid, dissolved within the fluid, carried by the fluid (e.g., suspended or dispersed), or the like. Examples of suitable materials include, but are not limited to, particles such as microparticles or nanoparticles, a chemical, a drug or a therapeutic agent, a diagnostic agent, a carrier, or the like.

As used herein, the term "fluid" generally refers to a substance that tends to flow and to conform to the outline of its container. Typically, fluids are materials that are unable to withstand a static shear stress, and when a shear stress is applied, the fluid experiences a continuing and permanent distortion. The fluid may have any suitable viscosity that permits at least some flow of the fluid. Non-limiting examples of fluids include liquids and gases, but may also include free-flowing solid particles, viscoelastic fluids, and the like. For example, the fluid may include a flowable matrix or a gel, e.g., formed from biodegradable and/or biocompatible material such as polylactic acid, polyglycolic acid, poly(lactic-co-glycolic acid), etc., or other similar materials.

One set of embodiments generally relates to interstitial and other bodily fluids for use in analyzing a condition of a subject or treating a subject. For instance, certain aspects of the invention are directed to causing the formation of a pooled region of fluid between the dermis and epidermis, such as in a suction blister. Fluid may be removed from the pooled region and analyzed in some fashion, or material may be delivered to the pooled region of fluid, in either case for diagnosis and/or treatment of a condition of a subject. In one set of embodiments, various particles may be delivered to the fluid, whether pooled between the dermis or epidermis, or in fluid removed from the subject, and the particles can assist in diagnosis or treatment as described herein. Optionally, fluid within a pooled region may be drained, e.g., externally, or the fluid may be resorbed, which may leave particles or other material embedded within the skin between the epidermis and dermis.

In some cases, as discussed herein, pooled regions of fluid may be created in the skin for facilitating delivery and/or withdraw of fluid from the skin. For instance, fluid may be pooled within the skin that is drawn from the surrounding dermal and/or epidermal layers within the skin. The fluid may include interstitial fluid, or even blood in some cases. In other cases, however, no pooling is necessary for the delivery and/or withdraw of fluid from the skin. For example, fluid may be withdrawn from the skin of a subject into a device, for example, using vacuum or other techniques such as discussed below, and/or fluid may be delivered into the skin of a subject without necessarily needing to create a suction blister or a pooled region of fluid in which to deliver fluid. Accordingly, it should be understood that in the descriptions herein, references to a "suction blister" or "pooled region of fluid" are by way of example only, and in other embodiments, fluid may be delivered to the skin without using a suction blister and/or without creating a pooled region of fluid within the skin.

It should also be understood that, in some cases, fluid may be created beneath the skin, e.g., in the fatty or muscle layers below the skin. Accordingly, descriptions herein of delivering and/or withdrawing fluid "in the skin" should also be understood to include, in other embodiments, the deliver and/or withdraw of fluid into layers directly beneath the skin.

One embodiment of the invention is illustrated in FIG. 1. In FIG. 1A, the skin 10 of a subject is shown, having two layers: an upper epidermis layer 15, and a lower dermis layer 17. Of course, other structures are typically present within the skin, for example, blood vessels, nerve endings, sweat glands, hair follicles, or the like, but these are not illustrated here for clarity. In FIG. 1B, epidermis 15 has been partially separated from dermis 17, creating a region 20 within the skin between the epidermis and the dermis. This region typically fills with fluid, such as interstitial fluid from the body, forming a pooled region of fluid. As shown in the example of FIG. 1B, the separation of the dermis and epidermis is created using interface 25 that is able to apply vacuum to the surface of the skin, thereby creating a suction blister within the skin formed by the pooled region of fluid. For example, vacuum may be created via conduit 27, which may be in fluidic communication with a vacuum source, such as a vacuum pump or an external (line) vacuum source. However, as discussed below, other methods may be used to create a pooled region of fluid within the skin besides, or in addition to, the use of vacuum. In addition, as previously discussed, certain embodiments of the invention do not require the creation of a pooled region of fluid within the skin.

Figure 1A:
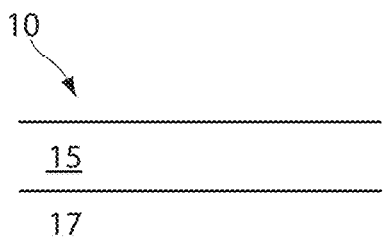
FIGS. 1A-1E schematically illustrate various systems and methods for creating pooled regions of fluid in the skin, according to certain embodiments of the invention.
Figure 1B:
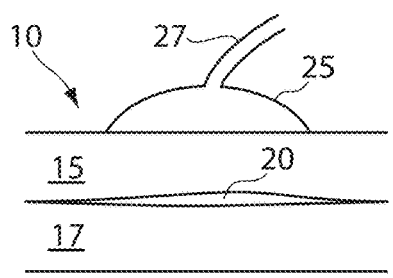
Figure 1C:
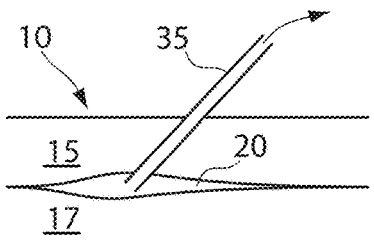

FIG. 1C shows an embodiment in which fluid is removed from pooled region 20. In this figure, needle 35, such as a hypodermic needle, may be used to remove at least a portion of the fluid from pooled region 20. The fluid may be stored, and/or analyzed to determine one or more analytes, e.g., a marker for a disease state, or the like. In some cases, the fluid may be actively removed, for example, upon the application of vacuum to the surface of skin 10, or upon the application of hygroscopic material to facilitate the removal of fluid from pooled region 20. In other cases, the fluid may be extracted, for example, via vacuum applied to the surface of skin 10 or to needle 35. In other cases, the fluid may be allowed to leave pooled region 20 passively. For example, in one embodiment, a cutter may be used to create a conduit by which fluid from pooled region 20 can escape. The cutter may be, for example, a needle or other piercing instrument, a cutting blade, or the like.

Figure 1D:
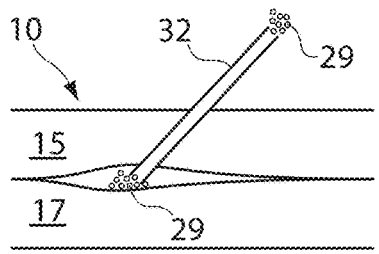

In FIG. 1D, material 29 is shown being delivered into the pooled region of fluid 20. Material 29 may be, for example, particles, such as microparticles or nanoparticles, a chemical, a drug or a therapeutic agent, a diagnostic agent, a reaction entity, or the like. In some cases, material 29 may comprise a carrier, such as a fluid carrier, that comprises the particles, chemicals, drugs, therapeutic agents, diagnostic agents, reaction entities, etc. As shown in this figure, needle 32 is used to deliver material 29 into pooled region 20. However, in other embodiments, other systems, such as a jet injector, may be used to deliver material 29 into the pooled region 20.

Figure 1E:
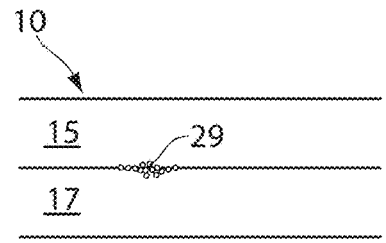

Once needle 32 has been removed from skin 10, material 29 may become embedded within pooled region 20, or may be dispersed within the subject, depending on the nature of material 29. For example, if fluid within the pooled region of fluid 20 is drained in some fashion, e.g., externally or is resorbed, etc., material 29 may remain embedded between epidermis 15 and dermis 17, as is shown in FIG. 1E. The material may become temporarily or permanently embedded between the dermis and the epidermis, or in some cases, the material may disperse within the subject, for example, dissolving or biodegrading within the subject, or the material may be one that can be transported within the subject, such as within the bloodstream. For example, in some cases, material 29 may contain a drug or other therapeutic agent that can be released from material 29, e.g., upon degradation of material 29. In one embodiment, for instance, material 29 may comprise particles able to controllably release a drug, a diagnostic agent, a therapeutic agent, etc.

Thus, certain aspects of the present invention are generally directed to the creation of suction blisters or other pooled regions of fluid within the skin. In one set of embodiments, a pooled region of fluid can be created between the dermis and epidermis of the skin. Suction blisters or other pooled regions may form in a manner such that the suction blister or other pooled region is not significantly pigmented in some cases, since the basal layer of the epidermis contains melanocytes, which are responsible for producing pigments. Such regions can be created by causing the dermis and the epidermis to at least partially separate, and as will be discussed below, a number of techniques can be used to at least partially separate the dermis from the epidermis. As mentioned, however, some embodiments of the invention do not necessarily require the creation of a pooled region of fluid within the skin.

The subject is usually human, although non-human subjects may be used in certain instances, for instance, other mammals such as a dog, a cat, a horse, a rabbit, a cow, a pig, a sheep, a goat, a rat (e.g., *Rattus Norvegicus*), a mouse (e.g., *Mus musculus*), a guinea pig, a hamster, a primate (e.g., a monkey, a chimpanzee, a baboon, an ape, a gorilla, etc.), or the like.

In one technique, a pool of interstitial fluid is formed between layers of skin of a subject and, after forming the pool, fluid is drawn from the pool by accessing the fluid through a layer of skin, for example, puncturing the outer layer of skin with a needle, e.g., with a microneedle. Specifically, for example, a suction blister can be formed and then the suction blister can be punctured and fluid can be drawn from the blister. In another technique, an interstitial region can be accessed and fluid drawn from that region without first forming a pool of fluid via a suction blister or the like. For example, a needle or a microneedle can be applied to the interstitial region and fluid can be drawn there from. In some cases, however, fluid may be withdrawn from the skin even without creating a suction blister or a pooled region of fluid within the skin.

Where needles are used, it can be advantageous to select needles of length such that interstitial fluid is preferentially obtained and, where not desirable, blood is not accessed. Those of ordinary skill in the art can arrange needles relative to the skin for these purposes including, in one embodiment, introducing needles into the skin at an angle, relative to the skin's surface, other than 90°, i.e., to introduce a needle or needles into the skin in a slanting fashion so as to limit the depth of penetration. In another embodiment, however, the needles may enter the skin at approximately 90°.

Pooled regions of fluids, if present, may be formed on any suitable location within the skin of a subject. Factors such as safety or convenience may be used to select a suitable location, as (in humans) the skin is relatively uniform through the body, with the exception of the hands and feet. As non-limiting examples, the pooled region may be formed on an arm or a leg, on the hands (e.g., on the back of the hand), on the feet, on the chest, abdomen, or the back of the subject, or the like. The size of the pooled region of fluid that is formed in the skin and/or the duration that the pooled region lasts within the skin depends on a variety of factors, such as the technique of creating the pooled region, the size of the pooled region, the size of the region of skin to which the technique is applied, the amount of fluid removed from the pooled region (if any), any materials that are delivered into the pooled region, or the like. For example, if vacuum is applied to the skin to create a suction blister, the vacuum applied to the skin, the duration of the vacuum, and/or the area of the skin affected may be controlled to control the size and/or duration of the suction blister. In some embodiments, it may be desirable to keep the pooled regions relatively small, for instance, to prevent an unsightly visual appearance, to allow for greater sampling accuracy (due to a smaller volume of material), or to allow for more controlled placement of particles within the skin. For example, the volume of the pooled region may be kept to less than about 2 ml, less than about 1 ml, less than about 500 microliters, less than about 300 microliters, less than about 100 microliters, less than about 50 microliters, less than about 30 microliters, less than about 10 microliters, etc., in certain cases, or the average diameter of the pooled region (i.e., the diameter of a circle having the same area as the pooled region) may be kept to less than about 5 cm, less than about 4 cm, less than about 3 cm, less than about 2 cm, less than about 1 cm, less than about 5 mm, less than about 4 mm, less than about 3 mm, less than about 2 mm, or less than about 1 mm.

A variety of techniques may be used to cause pooled regions of fluid to form within the skin and/or to withdraw a bodily fluid from the skin of a subject such as interstitial fluid or blood. In one set of embodiments, vacuum is applied to create a suction blister, or otherwise used to collect interstitial fluid or blood from a subject. In one set of embodiments, for example, a device containing a vacuum source, for instance, a self-contained vacuum source such as a pre-packaged vacuum chamber, may be used to withdraw blood or interstitial fluid from the subject. The fluid may be analyzed and/or stored for later use.

In other embodiments, other methods may be used to create as a pooled region of fluid within the skin and/or withdraw fluid from the skin besides, or in addition to, the use of vacuum. When vacuum (i.e., the amount of pressure below atmospheric pressure, such that atmospheric pressure has a vacuum of 0 mmHg, i.e., the pressure is gauge pressure rather than absolute pressure) is used to at least partially separate the dermis from the epidermis to cause the pooled region to form, the pooled region of fluid thus formed can be referred to as a suction blister. For example, pressures of at least about 50 mmHg, at least about 100 mmHg, at least about 150 mmHg, at least about 200 mmHg, at least about 250 mmHg, at least about 300 mmHg, at least about 350 mmHg, at least about 400 mmHg, at least about 450 mmHg, at least about 500 mmHg, at least about 550 mmHg, at least about 600 mmHg, at least about 650 mmHg, at least about 700 mmHg, or at least about 750 mmHg may be applied to the skin, e.g., to cause a suction blister and/or to collect interstitial fluid from a subject (as discussed, these measurements are negative relative to atmospheric pressure). For instance, a vacuum pressure of 100 mmHg corresponds to an absolute pressure of about 660 mmHg (i.e., 100 mmHg below 1 atm). Different amounts of vacuum may be applied to different subjects in some cases, for example, due to differences in the physical characteristics of the skin of the subjects.

The vacuum may be applied to any suitable region of the skin, and the area of the skin to which the vacuum may be controlled in some cases. For instance, the average diameter of the region to which vacuum is applied may be kept to less than about 5 cm, less than about 4 cm, less than about 3 cm, less than about 2 cm, less than about 1 cm, less than about 5 mm, less than about 4 mm, less than about 3 mm, less than about 2 mm, or less than about 1 mm. In addition, such vacuums may be applied for any suitable length of time at least sufficient to cause at least some separation of the dermis from the epidermis to occur. For instance, vacuum may be applied to the skin for at least about 1 min, at least about 3 min, at least about 5 min, at least about 10 min, at least about 15 min, at least about 30 min, at least about 45 min, at least about 1 hour, at least about 2 hours, at least about 3 hours, at least about 4 hours, etc. Examples of devices suitable for creating such suction blisters are discussed in more detail below. In other cases, however, bodily fluids such as blood or interstitial fluid may be removed from the skin using vacuum without the creation of a suction blister. Other non-limiting fluids include saliva, sweat, tears, mucus, plasma, lymph, or the like.

Other methods besides vacuum may be used to cause such separation to occur. For example, in another set of embodiments, heat may be used. For instance, a portion of the skin may be heated to at least about 40° C., at least about 50° C., or at least about 55° C., using any suitable technique, to cause such separation to occur. In some (but not all) cases, the temperature may be limited to no more than about 60° C. or no more than about 55° C. The skin may be heated, for instance, using an external heat source (e.g., radiant heat or a heated water bath), a chemical reaction, electromagnetic radiation (e.g., microwave radiation, infrared radiation, etc.), or the like. In some cases, the radiation may be focused on a relatively small region of the skin, e.g., to at least partially spatially contain the amount of heating within the skin that occurs.

In yet another set of embodiments, a separation chemical may be applied to the skin to at least partially cause separation of the dermis and the epidermis to occur. Non-limiting examples of such separation chemicals include proteases such as trypsin, purified human skin tryptase, or compound 48/80. Separation compounds such as these are commercially available from various sources. The separation chemical may be applied directly to the skin, e.g., rubbed into the surface of the skin, or in some cases, the separation chemical can be delivered into the subject, for example, between the epidermis and dermis of the skin. The separation chemical can, for example, be injected in between the dermis and the epidermis.

Another example of a separation chemical is a blistering agent, such as pit viper venom or blister beetle venom. Non-limiting examples of blistering agents include phosgene oxime, Lewisite, sulfur mustards (e.g., mustard gas or 1,5-dichloro-3-thiapentane, 1,2-bis(2-chloroethylthio)ethane, 1,3-bis(2-chloroethylthio)-n-propane, 1,4-bis(2-chloroethylthio)-n-butane, 1,5-bis(2-chloroethylthio)-n-pentane, 2-chloroethylchloromethylsulfide, bis(2-chloroethyl)sulfide, bis(2-chloroethylthio)methane, bis(2-chloroethylthiomethyl)ether, or bis(2-chloroethylthioethyl)ether), or nitrogen mustards (e.g., bis(2-chloroethyl)ethylamine, bis(2-chloroethyl)methylamine, or tris(2-chloroethyl)amine).

In still another set of embodiments, a device may be inserted into the skin and used to mechanically separate the epidermis and the dermis, for example, a wedge or a spike. Fluids may also be used to separate the epidermis and the dermis, in yet another set of embodiments. For example, saline or another relatively inert fluid may be injected into the skin between the epidermis and the dermis to cause them to at least partially separate.

These and/or other techniques may also be combined, in still other embodiments. For example, in one embodiment, vacuum and heat may be applied to the skin of a subject, sequentially and/or simultaneously, to cause such separation to occur. As a specific example, in one embodiment, vacuum is applied while the skin is heated to a temperature of between about 40° C. and about 50° C.

The fluid contained within the skin, e.g., within the pooled region of fluid is typically drawn from the surrounding dermal and/or epidermal layers within the skin, and includes interstitial fluid, or even blood in some cases. In some cases, such fluids may be collected even without creating a suction blister within the skin. For instance, a vacuum may be applied to the skin, e.g., through a needle as described herein, to withdraw interstitial fluid from the skin.

Often, such fluids will contain various analytes within the body that are important for diagnostic purposes, for example, markers for various disease states, such as glucose (e.g., for diabetics); other example analytes include ions such as sodium, potassium, chloride, calcium, magnesium, and/or bicarbonate (e.g., to determine dehydration); gases such as carbon dioxide or oxygen; $H^+$ (i.e., pH); metabolites such as urea, blood urea nitrogen or creatinine; hormones such as estradiol, estrone, progesterone, progestin, testosterone, androstenedione, etc. (e.g., to determine pregnancy, illicit drug use, or the like); or cholesterol. Other examples include insulin, or hormone levels.

As previously discussed, agents such as particles can be used to analyze bodily fluids, such as interstitial fluids. In some cases, the particles may be used to determine pH or metal ions, proteins, enzymes, antibodies, nucleic acids (e.g. DNA, RNA, etc.), drugs, sugars (e.g., glucose), hormones (e.g., estradiol, estrone, progesterone, progestin, testosterone, androstenedione, etc.), carbohydrates, or other analytes of interest. Other conditions that can be detected can include pH changes, which may indicate disease, yeast infection, periodontal disease at a mucosal surface, oxygen or carbon monoxide levels which indicate lung dysfunction, and drug levels, both legal prescription levels of drugs such as coumadin and illegal such as cocaine or nicotine. Further examples of analytes include those indicative of disease, such as cancer specific markers such as CEA and PSA, viral and bacterial antigens, and autoimmune indicators such as antibodies to double stranded DNA, indicative of Lupus. Still other conditions include exposure to elevated carbon monoxide, which could be from an external source or due to sleep apnea, too much heat (important in the case of babies whose internal temperature controls are not fully self-regulating) or from fever.

Still other potentially suitable analytes include various pathogens such as bacteria or viruses, and/or markers produced by such pathogens. Thus, in certain embodiments of the invention, as discussed below, one or more analytes within the skin, e.g., within a pooled region of fluid, may be determined in some fashion, which may be useful in determining a past, present and/or future condition of the subject.

In one embodiment as discussed below, an analyte may be determined as an "on/off" or "normal/abnormal" situation. In some cases, the particles (or other agents) indicate a change. Detection of the analyte, for example, may be indicative that insulin is needed; a trip to the doctor to check cholesterol; ovulation is occurring; kidney dialysis is needed; drug levels are present (e.g., especially in the case of illegal drugs) or too high/too low (e.g., important in care of geriatrics in particular in nursing homes). As another embodiment, however, an analyte may be determined quantitatively.

In some embodiments of the invention, one or more materials may be delivered to the skin. Examples of suitable materials include, but are not limited to, particles such as microparticles or nanoparticles, a chemical, a drug or a therapeutic agent, a diagnostic agent, a carrier, or the like. The materials may be delivered into the skin using any suitable technique; various techniques for delivery into the skin are well-known to those of ordinary skill in the art. Examples of suitable delivery techniques include, but are not limited to, injection (e.g., using needles such as hypodermic needles) or a jet injector, such as those discussed below.

In one set of embodiments, particles are delivered to the skin. The particles may be, for example, nanoparticles or microparticles, and in some cases, the particles may be anisotropic particles. Examples of such particles are discussed in more detail herein. In some cases, a plurality of particles may be used, and in some cases, some, or substantially all, of the particles may be the same. For example, at least about 10%, at least about 30%, at least about 40%, at least about 50%, at least about 60%, at least about 70%, at least about 80%, at least about 90%, at least about 95%, or at least about 99% of the particles may have the same shape, and/or may have the same composition. For example, in one embodiment, at least about 50% of the particles delivered to the skin may have the same shape, and/or may have the same composition. For instance, at least about 50% of the particles may be anisotropic particles.

The particles may be used for a variety of purposes. For instance, the particles may contain a diagnostic agent or a reaction entity able to interact with and/or associate with an analyte, or another reaction entity, or other particles. Such particles may be useful, for example, to determine one or more analytes, such as a marker of a disease state, as discussed below. As another example, the particles may contain a drug or a therapeutic agent, positioned on the surface and/or internally of the particles, which may be released by the particles and delivered to the subject. Specific examples of these and other embodiments are discussed in detail below.

In some cases, materials such as particles may become embedded within the skin, e.g., within a pooled region of fluid, for example, due to physical properties of the materials (e.g., size, hydrophobicity, etc.), and/or by draining at least a portion of the fluid within the pooled region such that the material is unable to escape, thereby remaining contained between the dermis and epidermis layers of the skin. Thus, in some cases, a depot of material may be formed within the skin, and the depot may be temporary or permanent. For instance, materials within the depot may eventually degrade (e.g., if the material biodegradable), enter the bloodstream, or be sloughed off to the environment, e.g., as the cells of the dermis differentiate to form new epidermis and accordingly push the material towards the surface of the skin. Thus, the depot of material may be present within the subject on a temporary basis (e.g., on a time scale of days or weeks), in certain instances.

Fluid may be drained from the pooled region using any suitable technique, for example, by externally removing the fluid from the pooled region (e.g., using techniques such as those discussed below), and/or by removing the vacuum or other stimulus used to cause the pooled region to occur, thereby allowing the fluid to become resorbed within the subject. Such resorption may occur, for example on a time scale of minutes to hours, depending on factors such as the size or volume of the pooled region of fluid. For example, in one embodiment, fluid is withdrawn using a needle such as a hypodermic needle. In some cases, this needle may also be used to deliver particles or other materials to the skin.

Fluids may also be externally removed from skin, e.g., from a pooled region of fluid, for example, to at least partially drain the pooled region of fluid, and/or for analysis. For instance, at least a portion of the fluid may be stored, and/or analyzed to determine one or more analytes, e.g., a marker for a disease state, or the like. The fluid withdrawn from the skin may be subjected to such uses, and/or one or more materials previously delivered to the skin (e.g., particles) may be subject to such uses. The fluid may be removed using any suitable technique. For example, in one embodiment, fluid is withdrawn using a needle such as a hypodermic needle. In some cases, this needle may also be used to deliver particles or other materials to the skin. The fluid may also be withdrawn using vacuums such as those discussed herein in another embodiment of the invention. For example, vacuum may be applied to a conduit, such as a needle, in fluidic communication with interstitial fluid, e.g., within a pooled region of fluid, in order to draw up at least a portion of the fluid from the pooled region. In yet another embodiment, fluid is withdrawn using capillary action (e.g., using a hypodermic needle having a suitably narrow inner diameter). In still another embodiment, pressure may be applied to force fluid out of the needle.

In still another embodiment, fluid may be withdrawn using a hygroscopic agent applied to the surface of the skin, or proximate the skin. In some cases, pressure may be applied to drive the hygroscopic agent into the skin. Hygroscopic agents typically are able to attract water from the surrounding environment, for instance, through absorption or adsorption. Non-limiting examples of hygroscopic agents include sugar, honey, glycerol, ethanol, methanol, sulfuric acid, methamphetamine, iodine, many chloride and hydroxide salts, and a variety of other substances. Other examples include, but are not limited to, zinc chloride, calcium chloride, potassium hydroxide or sodium hydroxide. In some cases, a suitable hygroscopic agent may be chosen based on its physical or reactive properties, e.g., inertness or biocompatibility towards the skin of the subject, depending on the application.

In some cases, fluids or other materials delivered to the subject may be used for indication of a past, present and/or future condition of the subject. Thus, the condition of the subject to be determined may be one that is currently existing in the subject, and/or one that is not currently existing, but the subject is susceptible or otherwise is at an increased risk to that condition. The condition may be a medical condition, e.g., diabetes or cancer, or other physiological conditions, such as dehydration, pregnancy, illicit drug use, or the like. Additional non-limiting examples are discussed below. In one set of embodiments, the materials may include a diagnostic agent, for example, one which can determine an analyte within the subject, e.g., one that is a marker for a disease state. Examples of such markers have been discussed above. As a specific non-limiting example, material delivered to the skin, e.g., to the dermis or epidermis, to a pooled region of fluid, etc., of a subject may include a particle including an antibody directed at a marker produced by bacteria.

In other cases, however, the materials delivered to the subject may be used to determine conditions that are external to the subject. For example, the materials may contain reaction entities able to recognize pathogens or other environmental conditions surrounding the subject, for example, an antibody able to recognize an external pathogen (or pathogen marker). As a specific example, the pathogen may be anthrax and the antibody may be an antibody to anthrax spores. As another example, the pathogen may be a *Plasmodia* (some species of which causes malaria) and the antibody may be an antibody that recognizes the *Plasmodia*.

Another aspect of the present invention is generally directed to devices able to cause the formation of the pooled region of fluids within the skin of a subject, and in some cases, to devices able to deliver and/or remove fluids or other materials from the pooled region of fluids. It should be understood, however, that other devices in other aspects do not require the formation of pooled regions of fluids within the skin. In some cases, the device may be able to collect bodily fluids such as interstitial fluid or blood from the skin, including fluid from a pooled region of fluid, or from other locations. For example, the device may take the form of a skin "patch," according to one embodiment. Typically, a skin patch includes one or more layers of material that are adhered to the surface of the skin, and can be applied by the subject or another person. In certain embodiments, layers or portions of the skin patch may be removed, leaving other layers or portions behind on the skin. Often, the skin patch lacks an external power source, although the various layers of the patch may contain various chemicals, such as drugs, therapeutic agents, diagnostic agents, reaction entities, etc. In some cases, the skin patch may also include mechanical elements as well, for example, a cutter such as is discussed herein.

As a specific, non-limiting example, in one embodiment, a skin patch or other device may be used to create a suction blister without an external power and/or a vacuum source. Examples of such devices include, besides skin patches, strips, tapes, bandages, or the like. For instance, a skin patch may be contacted with the skin of a subject, and a vacuum created through a change in shape of a portion of the skin patch or other device (e.g., using a shape memory polymer), which may be used to create a suction blister and/or withdraw fluid from the skin. As a specific example, a shape memory polymer may be shaped to be flat at a first temperature (e.g., room temperature) but curved at a second temperature (e.g., body temperature), and when applied to the skin, the shape memory polymer may alter from a flat shape to a curved shape, thereby creating a vacuum. As another example, a mechanical device may be used to create the vacuum. For example, springs, coils, expanding foam (e.g., from a compressed state), a shape memory polymer, shape memory metal, or the like may be stored in a compressed or wound released upon application to a subject, then released (e.g., unwinding, uncompressing, etc.), to mechanically create the vacuum. Thus, in some cases, the device is "pre-packaged" with a suitable vacuum source (e.g., a pre-evacuated vacuum chamber); for instance, in one embodiment, the device may be applied to the skin and activated in some fashion to create and/or access the vacuum source. One example is described below with respect to FIG. 8. In yet another example, a chemical reaction may be used to create a vacuum, e.g., a reaction in which a gas is produced, which can be harnessed to provide the mechanical force to create a vacuum. In still another example, a component of the device may be able to create a vacuum in the absence of mechanical force. In another example, the device may include a self-contained vacuum actuator, for example, chemical reactants, a deformable structure, a spring, a piston, etc.

Figure 8A:
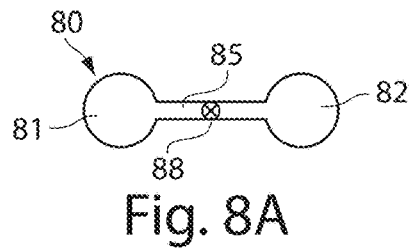
FIGS. 8A-8B illustrates top and side views, respectively, of a pre-loaded vacuum chamber, in another embodiment of the invention.
Figure 8B:
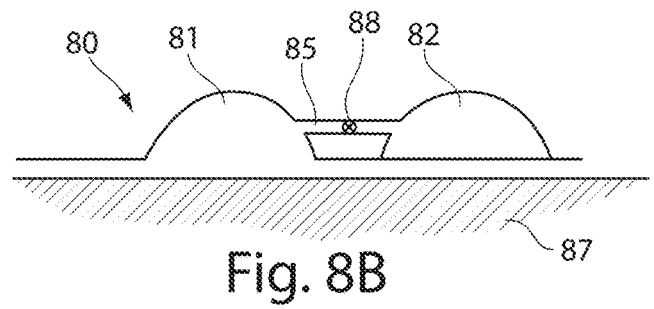
Figure 8C:
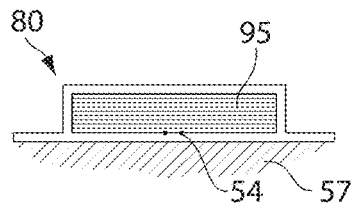
FIGS. 8C-8E illustrate a device containing a compressed foam, in yet another embodiment of the invention.
Figure 8D:
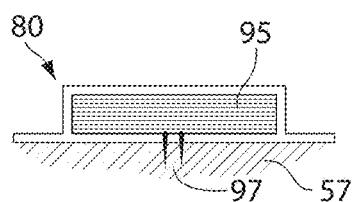
Figure 8E:
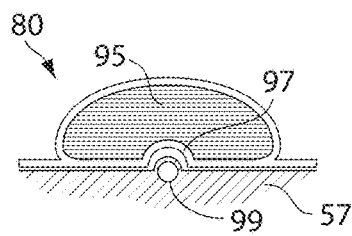

FIGS. 8C-8E illustrates an embodiment where a compressed foam is used to create a suction blister. In FIG. 8C, device 80 is placed on skin 57, and includes compressed foam 95. Device 80 includes a cutter 54 able to cut a portion of the skin, e.g., when pressed down onto the skin as is shown in FIG. 8D, e.g., creating a hole 97. In addition, the foam may be allowed to expand in some fashion after the device has been placed on the skin. For example, a housing portion of device 80 may be removed to allow expansion of the foam to occur. Expansion of the foam, as is shown in FIG. 8E, may create a suction and thereby cause the formation of a suction blister 99, and/or may allow fluids to be withdrawn from the skin.

Accordingly, in one set of embodiments, the skin patch or other device may be used to create a suction blister automatically, once activated, without any external control by a user. In other embodiments, however, the device may be larger. For instance, the device may be a handheld device that is applied to the surface of the skin of a subject. In some cases, however, the device may be sufficiently small or portable that the subject can self-administer the device. In certain embodiments, the device may also be powered. In some instances, the device may be applied to the surface of the skin, and is not inserted into the skin.

In other embodiments, however, at least a portion of the device may be inserted into the skin, for example, mechanically. For example, in one embodiment, the device may include a cutter, such as a hypodermic needle, a knife blade, a piercing element (e.g., a solid or hollow needle), or the like, as discussed herein. In some cases, the device may comprise a cutter able to cut or pierce the surface of the skin. The cutter may comprise any mechanism able to create a path to a fluid within the skin, e.g., through which fluids may be delivered and/or removed from the skin. For example, the cutter may comprise a hypodermic needle, a knife blade, a piercing element (e.g., a solid or a hollow needle), or the like, which can be applied to the skin to create a suitable conduit for the withdrawal of fluid from the skin. In one embodiment, a cutter is used to create such a pathway and removed, then fluid is removed via this pathway using any suitable technique. In another embodiment, the cutter remains in place within the skin, and fluid may be drawn through a conduit within the cutter.

As an example, the device may be constructed such that a cutter or a needle is inserted into the skin after a suction blister is formed. In some cases, the device may be designed such that portions of the device are separable. For example, a first portion of the device may be removed from the surface of the skin, leaving other portions of the device behind on the skin. In one embodiment, a stop may also be included to prevent or control the depth to which the cutter or other device inserts into the skin, e.g., to control penetration to the epidermis, dermis, etc.

Figure 2A:
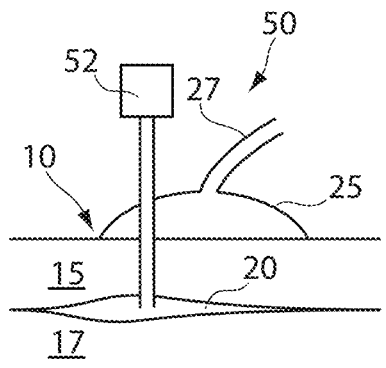
FIGS. 2A-2C illustrate various devices useful for creating pooled regions of fluid in the skin, in some embodiments.

Various non-limiting examples of such devices are illustrated in FIG. 2. In FIG. 2A, device 50 includes an interface 25 that can be used to apply vacuum to the surface of the skin 10, thereby creating a pooled region of fluid 20 within the skin between the epidermis 15 and the dermis 17. In the embodiment illustrated, device 50 includes conduit 27, which can be connected in fluidic communication with a vacuum source, such as a vacuum pump or an external (line) vacuum source. In this figure, device 50 also includes a cutter, in this case a hypodermic needle, that can be extended into the pooled region of fluid, and used to deliver and/or remove fluids or other materials from the pooled region of fluid. In this figure, the hypodermic needle is used both to create a conduit within the skin and to delivery and/or remove fluids from the skin; in other embodiments, however, the needle (or other device) may be removed from the skin, leaving behind a "hole" within the skin through which fluids can be delivered and/or removed. In this figure, fluid withdrawn from the pooled region of fluid may be delivered to a sensor 52, which can be used to determine an analyte, such as a marker for a disease state, that is present within skin 10. The cutter may be an integral part of device 50, or a separate device. In some cases, device 50 may comprise separably removable portions. For instance, after creating the suction blister, interface 25 may be removable from device 50, leaving hypodermic needle 40 within skin 10.

Figure 2B:
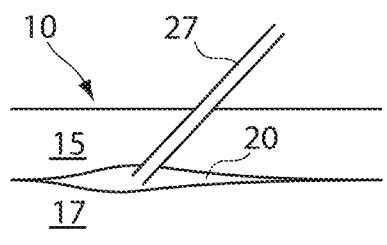

Another example of a device is shown in FIG. 2B. In this figure, device 10 includes conduit 27, in which fluids can be delivered and/or removed. In one embodiment, a fluid, such as saline, is delivered through conduit 27, thereby creating a pooled region of fluid between the epidermis 15 and the dermis 17. Optionally, materials such as particles may be delivered into the pooled region of fluid using conduit 27, e.g., for therapeutic or diagnostic purposes. In some cases, after creation of the pooled region of fluid within skin 10, at least a portion of the fluid may be removed through conduit 27 (or a separate conduit, in some cases) for analysis, e.g., as previously discussed.

Figure 2C:
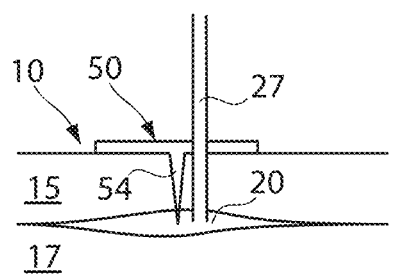

In FIG. 2C, a similar device is shown, including a cutter 54, such as a hypodermic needle or a knife blade, that can be inserted into the skin and used to at least partially separate the epidermis from the dermis to allow for the creation of a pooled region of fluid 20. For example, cutter 54 may separate the epidermis from the dermis by delivering a separation chemical to this region, and/or by conducting heat to this region. Also shown in this example is conduit 27, which may be used to deliver and/or remove fluid from the pooled region of fluid. In some cases, cutter 54 and conduit 27 may be separately administered to the subject, e.g., sequentially or simultaneously. In another embodiment, both may be part of the same device that is administered to skin 10, and in some cases, cutter 54 may be separated from conduit 27, e.g., such that cutter 54 can be removed from the skin while conduit 27 remains within the skin.

Figure 3A:
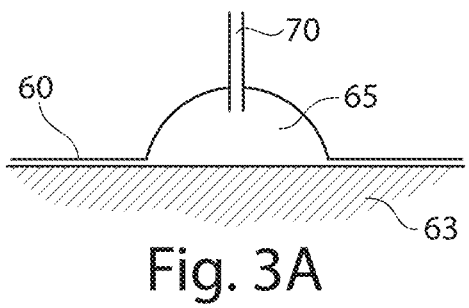
FIGS. 3A-3C illustrate an example of one embodiment of the invention useful for puncturing and creating a pooled region of the skin.
Figure 3B:
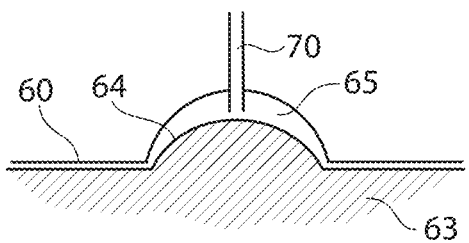

FIG. 3A illustrates a device according to another embodiment of the invention. In this example, a device 60 is applied to skin 63. Device 60 may be, for instance, a patch, an appliqué, a mechanical device, or the like. A vacuum is created between device 60 and the skin in region 65. The vacuum may be contained by the device itself, and/or through connection with a vacuum source, such as a vacuum pump or an external (line) vacuum source. Other examples of vacuum sources include, but are not limited to, syringes, bulbs, vacuum pumps, Venturi tubes, or even manual (mouth) suction. Also shown in FIG. 3B is cutter 70. Cutter 70 may be, for example, a needle or a microneedle, a knife blade, or the like.

Figure 3C:
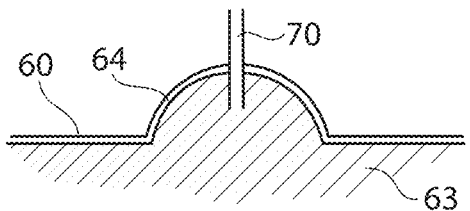

As the suction blister forms within the skin, portions of the skin may be uplifted due to the pooled region of fluid, shown in FIG. 3B as portion 64 extending upwardly into region 65 of device 60. As portion 64 extends upward into region 65, it comes into contact with cutter 70. Under certain conditions, the skin may extend upward sufficiently into region 65 that cutter 70 cuts into skin 65, as is shown in FIG. 3C. For instance, if cutter 70 is a hypodermic needle, upon piercing of the needle into the skin, the needle may be used to access interstitial fluid within the skin, e.g., within a pooled region of fluid within the skin forming the suction blister. Accordingly, fluid may be withdrawn and/or materials such as particles may be delivered into the pooled region using the hypodermic needle.

As additional examples, the device may comprise a first portion able to create a pooled region of fluid within the skin of a subject and a second portion able to determine fluid removed from the pooled region, or a first portion able to create a pooled region of fluid within the skin of a subject and a second portion able to deliver fluid to the pooled region of fluid, where the various portions may be separated from each other. For instance, the fluid itself may be determined (for example, the presence and/or absence of the fluid, the concentration of fluid, the volume of fluid, etc.), or an analyte within the fluid may be determined, e.g., qualitatively or quantitatively, whether the analyte is present and/or absent, etc. As yet another example, the device may comprise a first portion able to create a pooled region of fluid within the skin of a subject, a second portion able to determine fluid removed from the pooled region, and a third portion able to deliver fluid to the pooled region of fluid, where some or all of the portions may be separated from each other.

In certain embodiments, the device is able to create a pooled region of fluid within the skin of a subject. In one embodiment, the device is able to create vacuum on the surface of the skin, e.g., to form a suction blister within the skin. In other embodiments, however, the device may create a vacuum to withdraw fluid from the skin without necessarily creating a pooled region of fluid or forming a suction blister within the skin. In one set of embodiments, fluids may be delivered to or withdrawn from the skin using vacuum. The vacuum may be an external vacuum source, and/or the vacuum source may be self-contained within the device. For example, vacuums of at least about 50 mmHg, at least about 100 mmHg, at least about 150 mmHg, at least about 200 mmHg, at least about 250 mmHg, at least about 300 mmHg, at least about 350 mmHg, at least about 400 mmHg, at least about 450 mmHg, at least about 500 mmHg, at least 550 mmHg, at least 600 mmHg, at least 650 mmHg, at least about 700 mmHg, or at least about 750 mmHg may be applied to the skin to cause a suction blister. Any source of vacuum may be used. For example, the device may comprise a vacuum source, and/or be connectable to a vacuum source is external to the device, such as a vacuum pump or an external (line) vacuum source. In some cases, vacuum may be created manually, e.g., by manipulating a syringe pump or the like, or the low pressure may be created mechanically or automatically, e.g., using a piston pump, a syringe, a bulb, a Venturi tube, manual (mouth) suction, etc. or the like.

As mentioned, any source of vacuum may be used. For example, the device may comprise an internal vacuum source, and/or be connectable to a vacuum source is external to the device, such as a vacuum pump or an external (line) vacuum source.

In one set of embodiments, a device of the present invention may not have an external power and/or a vacuum source. In some cases, the device is "pre-loaded" with a suitable vacuum source; for instance, in one embodiment, the device may be applied to the skin and activated in some fashion to create and/or access the vacuum source. As one example, a device of the present invention may be contacted with the skin of a subject, and a vacuum created through a change in shape of a portion of the device (e.g., using a shape memory polymer), or the device may contain one or more sealed, self-contained vacuum compartments, where a seal is punctured in some manner to create a vacuum. For instance, upon puncturing the seal, a vacuum compartment may be in fluidic communication with a needle, which can be used to move the skin towards the device, withdraw fluid from the skin, or the like.

As another example, a shape memory polymer may be shaped to be flat at a first temperature (e.g., room temperature) but curved at a second temperature (e.g., body temperature), and when applied to the skin, the shape memory polymer may alter from a flat shape to a curved shape, thereby creating a vacuum. As yet another example, a mechanical device may be used to create the vacuum, For example, springs, coils, expanding foam (e.g., from a compressed state), a shape memory polymer, shape memory metal, or the like may be stored in a compressed or wound released upon application to a subject, then released (e.g., unwinding, uncompressing, etc.), to mechanically create the vacuum. Non-limiting examples of shape-memory polymers and metals include Nitinol, compositions of oligo(epsilon-caprolactone)diol and crystallizable oligo(rho-dioxanone) diol, or compositions of oligo(epsilon-caprolactone)dimethacrylate and n-butyl acrylate.

Figure 6:
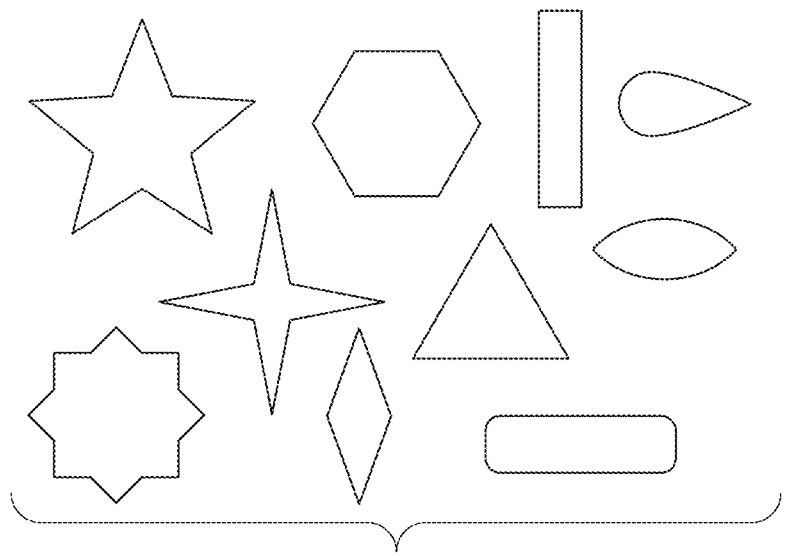
FIG. 6 illustrates certain non-circular interfaces, in accordance with another embodiment of the invention.

In some cases, the device includes an interface that is able to apply vacuum to the skin. The interface may be, for example, a suction cup or a circular bowl that is placed on the surface of the skin, and vacuum applied to the interface to create a vacuum. In one set of embodiments, the interface is part of a support structure, as discussed herein. The interface may be formed from any suitable material, e.g., glass, rubber, polymers such as silicone, polyurethane, nitrile rubber, EPDM rubber, neoprene, or the like. In some cases, the seal between the interface and the skin may be enhanced (e.g., reducing leakage), for instance, using vacuum grease, petroleum jelly, a gel, a hydrogel, or the like. In some cases, the interface may be relatively small, for example, having a diameter of less than about 5 cm, less than about 4 cm, less than about 3 cm, less than about 2 cm, less than about 1 cm, less than about 5 mm, less than about 4 mm, less than about 3 mm, less than about 2 mm, or less than about 1 mm. The interface may be circular, although other shapes are also possible, for example, square, star-shaped (having 5, 6, 7, 8, 9, 10, 11, etc. points), tear-drop, oval, rectangular, or the like. In some cases, non-circular shapes may be used since high-energy points, e.g., the points or corners of the shape may enhance or accelerate blister formation. Non-limiting examples of such shapes are shown in FIG. 6. Other non-circular shapes besides these may also be used in other embodiments.

The interface may also be selected, in some cases, to keep the size of the pooled region below a certain area, e.g., to minimize pain or discomfort to the subject, for aesthetic reasons, or the like. The interface may be constructed out of any suitable material, e.g., glass, plastic, or the like.

The device may also comprise, in some cases, a portion able to deliver materials such as particles into the skin, for example, into the dermis or epidermis, into a pooled region within the skin, etc. For example, the device may include a needle such as a hypodermic needle or microneedles, or jet injectors such as those discussed below. As an example, in one embodiment, a needle such as a hypodermic needle can be used to deliver and/or withdraw fluid to or from the skin. In some cases, for example, fluid may be delivered and/or withdrawn from a pooled region of fluid in the skin, if present. Hypodermic needles are well-known to those of ordinary skill in the art, and can be obtained commercially with a range of needle gauges. For example, the needle may be in the 20-30 gauge range, or the needle may be 32 gauge, 33 gauge, 34 gauge, etc.

Accordingly, in one set of embodiments, many techniques for delivering and/or withdrawing fluid are described in the applications incorporated herein. It is to be understood that, generally, fluids may be delivered and/or withdrawn in a variety of ways, and various systems and methods for delivering and/or withdrawing fluid from the skin are discussed herein. It should also be understood that techniques for delivering materials into a pooled region of the skin are by way of example only, and that in other aspects, the invention is directed to techniques for delivering and/or withdrawing fluid from the skin of a subject (with or without the presence of a pooled region of the skin). Some additional non-limiting examples of such techniques are discussed below. In one set of embodiments, for example, techniques for piercing or altering the surface of the skin to transport a fluid are discussed, for example, a needle such as a hypodermic needle or microneedles, chemicals applied to the skin (e.g., penetration enhancers), or jet injectors or other techniques such as those discussed below.

If needles are present, the needles may be of any suitable size and length, and may be solid or hollow. The needles may have any suitable cross-section (e.g., perpendicular to the direction of penetration), for example, circular, square, oval, elliptical, rectangular, rounded rectangle, triangular, polygonal, hexagonal, irregular, etc. For example, the needle may have a length of less than about 5 mm, less than about 4 mm, less than about 3 mm, less than about 2 mm, less than about 1 mm, less than about 800 micrometers, less than 600 micrometers, less than 500 micrometers, less than 400 micrometers, less than about 300 micrometers, less than about 200 micrometers, less than about 175 micrometers, less than about 150 micrometers, less than about 125 micrometers, less than about 100 micrometers, less than about 75 micrometers, less than about 50 micrometers, etc. The needle may also have a largest cross-sectional dimension of less than about 5 mm, less than about 4 mm, less than about 3 mm, less than about 2 mm, less than about 1 mm, less than about 800 micrometers, less than 600 micrometers, less than 500 micrometers, less than 400 micrometers, less than about 300 micrometers, less than about 200 micrometers, less than about 175 micrometers, less than about 150 micrometers, less than about 125 micrometers, less than about 100 micrometers, less than about 75 micrometers, less than about 50 micrometers, etc. For example, in one embodiment, the needle may have a rectangular cross section having dimensions of 175 micrometers by 50 micrometers. In one set of embodiments, the needle may have an aspect ratio of length to largest cross-sectional dimension of at least about 2:1, at least about 3:1, at least about 4:1, at least about 5:1, at least about 7:1, at least about 10:1, at least about 15:1, at least about 20:1, at least about 25:1, at least about 30:1, etc. In one embodiment, the needle is a microneedle.

For example, the needle may be a microneedle such as those disclosed in U.S. Pat. No. 6,334,856, issued Jan. 1, 2002, entitled "Microneedle Devices and Methods of Manufacture and Use Thereof," by Allen, et al., and the microneedle may be used to deliver and/or withdraw fluids or other materials to or from the skin of a subject. The microneedles may be hollow or solid, and may be formed from any suitable material, e.g., metals, ceramics, semiconductors, organics, polymers, and/or composites. Examples include, but are not limited to, pharmaceutical grade stainless steel, titanium, nickel, iron, gold, tin, chromium, copper, alloys of these or other metals, silicon, silicon dioxide, and polymers, including polymers of hydroxy acids such as lactic acid and glycolic acid polylactide, polyglycolide, polylactide-co-glycolide, and copolymers with polyethylene glycol, polyanhydrides, polyorthoesters, polyurethanes, polybutyric acid, polyvaleric acid, polylactide-co-caprolactone, polycarbonate, polymethacrylic acid, polyethylenevinyl acetate, polytetrafluorethylene, polymethyl methacrylate, polyacrylic acid, or polyesters. In some cases, more than one microneedle may be used. For example, arrays of microneedles may be used, and the microneedles may be arranged in the array in any suitable configuration, e.g., periodic, random, etc. In some cases, the array may have 3 or more, 4 or more, 5 or more, 6 or more, 10 or more, 15 or more, 20 or more, 35 or more, 50 or more, 100 or more, or any other suitable number of microneedles. It should be understood that references to "needle" or "microneedle" as discussed herein are by way of example and ease of presentation only, and that in other embodiments, more than one needle and/or microneedle may be present in any of the descriptions herein.

As still another example, pressurized fluids may be used to deliver fluids or other materials into the skin, for instance, using a jet injector or a "hypospray." Typically, such devices produce a high-pressure "jet" of liquid or powder (e.g., a biocompatible liquid, such as saline) that drives material into the skin, and the depth of penetration may be controlled, for instance, by controlling the pressure of the jet. The pressure may come from any suitable source, e.g., a standard gas cylinder or a gas cartridge. A non-limiting example of such a device can be seen in U.S. Pat. No. 4,103,684, issued Aug. 1, 1978, entitled "Hydraulically Powered Hypodermic Injector with Adapters for Reducing and Increasing Fluid Injection Force," by Ismach. Pressurization of the liquid may be achieved, for example, using compressed air or gas, for instance, from a gas cylinder or a gas cartridge.

In addition, in certain embodiments, the device may comprise a portion able to remove at least a portion of the fluid from the skin. For instance, the device may comprise a hypodermic needle, a vacuum source, a hygroscopic agent, or the like. In certain cases, the portion of the device able to remove fluid may also be used to deliver fluids to the skin. Fluid may be removed from the skin using any suitable technique. For instance, in one embodiment, the fluid is removed manually, e.g., by manipulating a plunger on a syringe. In another embodiment, the fluid can be removed from the skin mechanically or automatically, e.g., using a piston pump or the like.

In some aspects, the device may include channels such as microfluidic channels, which may be used to deliver and/or withdraw fluids and/or other materials such as particles into or out of the skin, e.g., within the pooled region of fluid. In some cases, the microfluidic channels are in fluid communication with a fluid transporter that is used to deliver and/or withdraw fluids to or from the skin. For example, in one set of embodiments, the device may include a hypodermic needle that can be inserted into the skin, and fluid may be delivered into the skin via the needle and/or withdrawn from the skin via the needle. The device may also include one or more microfluidic channels to contain fluid for delivery to the needle, e.g., from a source of fluid, and/or to withdraw fluid from the skin, e.g., for delivery to an analytical compartment within the device, to a reservoir for later analysis, or the like.

Figure 4A:
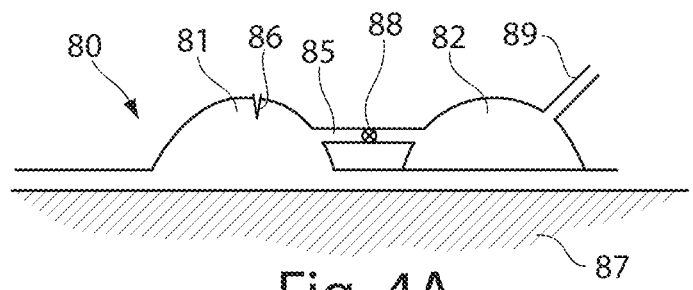
FIGS. 4A-4B illustrate additional examples of various devices of the invention.
Figure 5:
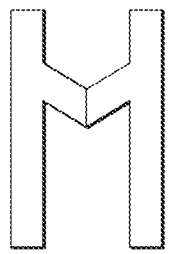
FIG. 5 illustrates a check valve according to one embodiment of the invention.
Figure 7:
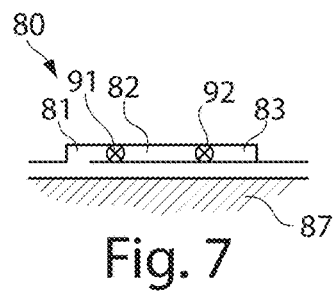
FIG. 7 illustrates another embodiment of the invention useful for creating a pooled region of the skin.

One embodiment of a device including microfluidic channels is now disclosed with reference to FIG. 4A. In this figure, device 80, applicable to skin 87, includes a first compartment 81 and a second compartment 82. It should be noted that, in some embodiments, the compartments are not necessarily discrete chambers as are shown in FIG. 4A, and various compartments may be separated from each other through the use of controllers such as valves, membranes, or the like, e.g., as is shown in FIG. 7 with compartments 81, 82 and 83 and valves 91 and 92. Referring again to FIG. 4A, device 80 may be, for instance, a patch, an appliqué, a mechanical device, etc. First compartment 81 and second compartment 82 may be fluidic communication, e.g., using a microfluidic channel 85. Optionally, a check valve 88 may be used to prevent backflow of fluid from second compartment 82 into first compartment 81 (or vice versa, depending on the embodiment). Check valve 88, if present, may be any valve that preferentially allows fluid flow in one direction, relative to the opposite direction. For instance, as is shown in FIG. 5, check valve may comprise one or more hinged portions that are able to swing in one direction (e.g., downstream), but are not able to swing in the opposite direction (e.g., upstream).

In one example, vacuum is applied to the device from a vacuum source attached to channel 89, and the vacuum can be used to create a suction blister in the skin, as discussed above. For example, first compartment 81 may include a needle 86 that is used to access the fluid within the skin, e.g., within a pooled region of fluid created by the suction blister. Second compartment 82 may be used, for example, to analyze a component of a fluid withdrawn from the skin. In another example, channel 89 may be connected to a source of pressure, and second compartment 82 may contain a fluid to be delivered to the skin.

In some cases, more than one compartment may be present within the device, and in some cases, some or all of the compartments may be in fluidic communication, e.g., via channels such as microfluidic channels. In various embodiments, a variety of compartments and/or channels may be present within the device, depending on the application. For example, the device may contain compartments for sensing an analyte, compartments for holding reagents, compartments for controlling temperature, compartments for controlling pH or other conditions, compartments for creating or buffering pressure or vacuum, compartments for controlling or dampening fluid flow, mixing compartments, or the like.

Figure 4B:
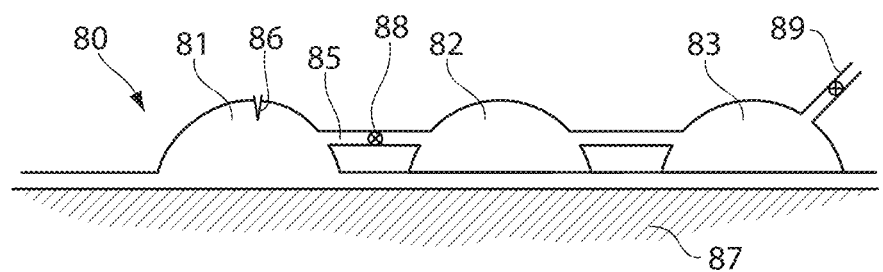

As a specific non-limiting example, in FIG. 4B, third compartment 83 is used to facilitate the creation of pressure or vacuum within first compartment 81. The compartments may be arranged in any suitable arrangement, e.g., as shown in FIG. 4B with first compartment 81 in fluid communication via a first channel to second compartment 82, which is in fluid communication via a third channel to third compartment 83. As discussed above, first compartment 81 may be used to create a vacuum on the skin and/or access fluid within the skin, facilitated by vacuum created using third compartment 83, and fluid drawn from the skin may pass through microfluidic channel 85 (and optional check valve 88) to enter second compartment 82 for analysis. The analysis of the fluid may be performed using any suitable technique such as those described herein. For example, second compartment 82 may contain an agent able to determine an analyte, e.g., particles producing a color change which is proportional to the amount of analyte.

Yet another example is described with reference to FIG. 8, showing top (FIG. 8A) and side (FIG. 8B) views of an example device 80. In this figure, first compartment 81 and second compartment 82 are in fluidic communication, e.g., using a microfluidic channel 85. A valve 88 separates these compartments. The device may be "pre-loaded" with a vacuum within second compartment 82, which is not in fluidic communication with first compartment due to closure of valve 88. After device 80 is applied to the skin 87 of a subject, e.g., in an air-tight fashion such that first compartment 81 is not exposed to the external environment, valve 88 may be opened, thereby allowing first compartment 81 to become fluidically exposed to the vacuum within second compartment 82. In this way, vacuum may be applied to the skin via first compartment 81 once valve 88 has been opened. Thus, certain embodiments of the present invention are directed to devices able to withdraw a fluid from the skin, e.g., blood or interstitial fluid, for analysis and/or storage for later use.

Thus, in one set of embodiments, the device may include a microfluidic channel. As used herein, "microfluidic," "microscopic," "microscale," the "micro-" prefix (for example, as in "microchannel"), and the like generally refers to elements or articles having widths or diameters of less than about 1 mm, and less than about 100 microns (micrometers) in some cases. In some embodiments, larger channels may be used instead of, or in conjunction with, microfluidic channels for any of the embodiments discussed herein. For examples, channels having widths or diameters of less than about 10 mm, less than about 9 mm, less than about 8 mm, less than about 7 mm, less than about 6 mm, less than about 5 mm, less than about 4 mm, less than about 3 mm, or less than about 2 mm may be used in certain instances. In some cases, the element or article includes a channel through which a fluid can flow. In all embodiments, specified widths can be a smallest width (i.e. a width as specified where, at that location, the article can have a larger width in a different dimension), or a largest width (i.e. where, at that location, the article has a width that is no wider than as specified, but can have a length that is greater). Thus, for instance, the microfluidic channel may have an average cross-sectional dimension (e.g., perpendicular to the direction of flow of fluid in the microfluidic channel) of less than about 1 mm, less than about 500 microns, less than about 300 microns, or less than about 100 microns. In some cases, the microfluidic channel may have an average diameter of less than about 60 microns, less than about 50 microns, less than about 40 microns, less than about 30 microns, less than about 25 microns, less than about 10 microns, less than about 5 microns, less than about 3 microns, or less than about 1 micron.

A "channel," as used herein, means a feature on or in an article (e.g., a substrate) that at least partially directs the flow of a fluid. In some cases, the channel may be formed, at least in part, by a single component, e.g. an etched substrate or molded unit. The channel can have any cross-sectional shape, for example, circular, oval, triangular, irregular, square or rectangular (having any aspect ratio), or the like, and can be covered or uncovered (i.e., open to the external environment surrounding the channel). In embodiments where the channel is completely covered, at least one portion of the channel can have a cross-section that is completely enclosed, and/or the entire channel may be completely enclosed along its entire length with the exception of its inlet and outlet.

A channel may have any aspect ratio, e.g., an aspect ratio (length to average cross-sectional dimension) of at least about 1:1, at least about 2:1, more typically at least about 3:1, at least about 5:1, at least about 10:1, etc. As used herein, a "cross-sectional dimension," in reference to a fluidic or microfluidic channel, is measured in a direction generally perpendicular to fluid flow within the channel. A channel generally will include characteristics that facilitate control over fluid transport, e.g., structural characteristics and/or physical or chemical characteristics (hydrophobicity vs. hydrophilicity) and/or other characteristics that can exert a force (e.g., a containing force) on a fluid. The fluid within the channel may partially or completely fill the channel. In some cases the fluid may be held or confined within the channel or a portion of the channel in some fashion, for example, using surface tension (e.g., such that the fluid is held within the channel within a meniscus, such as a concave or convex meniscus). In an article or substrate, some (or all) of the channels may be of a particular size or less, for example, having a largest dimension perpendicular to fluid flow of less than about 5 mm, less than about 2 mm, less than about 1 mm, less than about 500 microns, less than about 200 microns, less than about 100 microns, less than about 60 microns, less than about 50 microns, less than about 40 microns, less than about 30 microns, less than about 25 microns, less than about 10 microns, less than about 3 microns, less than about 1 micron, less than about 300 nm, less than about 100 nm, less than about 30 nm, or less than about 10 nm or less in some cases. In one embodiment, the channel is a capillary.

In some cases, the device may contain one or more chambers or reservoirs for holding fluid. In some cases, the chambers may be in fluidic communication with one or more fluid transporters and/or one or more microfluidic channels. For instance, the device may contain a chamber for collecting fluid withdrawn from a subject (e.g., for storage and/or later analysis), a chamber for containing a fluid for delivery to the subject (e.g., blood, saline, optionally containing drugs, hormones, vitamins, pharmaceutical agents, or the like), etc.

A variety of materials and methods, according to certain aspects of the invention, can be used to form the device, e.g., microfluidic channels. For example, various components of the invention can be formed from solid materials, in which the channels can be formed via micromachining, film deposition processes such as spin coating and chemical vapor deposition, laser fabrication, photolithographic techniques, etching methods including wet chemical or plasma processes, and the like. See, for example, *Scientific American*, 248:44-55, 1983 (Angell, et al).

In one set of embodiments, various components of the systems and devices of the invention can be formed of a polymer, for example, an elastomeric polymer such as polydimethylsiloxane ("PDMS"), polytetrafluoroethylene ("PTFE" or Teflon®), or the like. For instance, according to one embodiment, a microfluidic channel may be implemented by fabricating the fluidic system separately using PDMS or other soft lithography techniques (details of soft lithography techniques suitable for this embodiment are discussed in the references entitled "Soft Lithography," by Younan Xia and George M. Whitesides, published in the *Annual Review of Material Science*, 1998, Vol. 28, pages 153-184, and "Soft Lithography in Biology and Biochemistry," by George M. Whitesides, Emanuele Ostuni, Shuichi Takayama, Xingyu Jiang and Donald E. Ingber, published in the *Annual Review of Biomedical Engineering*, 2001, Vol. 3, pages 335-373; each of these references is incorporated herein by reference). Other examples of potentially suitable polymers include, but are not limited to, polyethylene terephthalate (PET), polyacrylate, polymethacrylate, polycarbonate, polystyrene, polyethylene, polypropylene, polyvinylchloride, polytetrafluoroethylene, a fluorinated polymer, a silicone such as polydimethylsiloxane, polyvinylidene chloride, bis-benzocyclobutene ("BCB"), a polyimide, a fluorinated derivative of a polyimide, or the like. Combinations, copolymers, or blends involving polymers including those described above are also envisioned. The device may also be formed from composite materials, for example, a composite of a polymer and a semiconductor material.

In some embodiments, various components of the invention are fabricated from polymeric and/or flexible and/or elastomeric materials, and can be conveniently formed of a hardenable fluid, facilitating fabrication via molding (e.g. replica molding, injection molding, cast molding, etc.). The hardenable fluid can be essentially any fluid that can be induced to solidify, or that spontaneously solidifies, into a solid capable of containing and/or transporting fluids contemplated for use in and with the fluidic network. In one embodiment, the hardenable fluid comprises a polymeric liquid or a liquid polymeric precursor (i.e. a "prepolymer"). Suitable polymeric liquids can include, for example, thermoplastic polymers, thermoset polymers, waxes, metals, or mixtures or composites thereof heated above their melting point. As another example, a suitable polymeric liquid may include a solution of one or more polymers in a suitable solvent, which solution forms a solid polymeric material upon removal of the solvent, for example, by evaporation. Such polymeric materials, which can be solidified from, for example, a melt state or by solvent evaporation, are well known to those of ordinary skill in the art. A variety of polymeric materials, many of which are elastomeric, are suitable, and are also suitable for forming molds or mold masters, for embodiments where one or both of the mold masters is composed of an elastomeric material. A non-limiting list of examples of such polymers includes polymers of the general classes of silicone polymers, epoxy polymers, and acrylate polymers. Epoxy polymers are characterized by the presence of a three-membered cyclic ether group commonly referred to as an epoxy group, 1,2-epoxide, or oxirane. For example, diglycidyl ethers of bisphenol A can be used, in addition to compounds based on aromatic amine, triazine, and cycloaliphatic backbones. Another example includes the well-known Novolac polymers. Non-limiting examples of silicone elastomers suitable for use according to the invention include those formed from precursors including the chlorosilanes such as methylchlorosilanes, ethylchlorosilanes, phenylchlorosilanes, etc.

Silicone polymers are used in certain embodiments, for example, the silicone elastomer polydimethylsiloxane. Non-limiting examples of PDMS polymers include those sold under the trademark Sylgard by Dow Chemical Co., Midland, Mich., and particularly Sylgard 182, Sylgard 184, and Sylgard 186. Silicone polymers including PDMS have several beneficial properties simplifying fabrication of the microfluidic structures of the invention. For instance, such materials are inexpensive, readily available, and can be solidified from a prepolymeric liquid via curing with heat. For example, PDMSs are typically curable by exposure of the prepolymeric liquid to temperatures of about, for example, about 65° C. to about 75° C. for exposure times of, for example, about an hour. Also, silicone polymers, such as PDMS, can be elastomeric and thus may be useful for forming very small features with relatively high aspect ratios, necessary in certain embodiments of the invention. Flexible (e.g., elastomeric) molds or masters can be advantageous in this regard.

One advantage of forming structures such as microfluidic structures of the invention from silicone polymers, such as PDMS, is the ability of such polymers to be oxidized, for example by exposure to an oxygen-containing plasma such as an air plasma, so that the oxidized structures contain, at their surface, chemical groups capable of cross-linking to other oxidized silicone polymer surfaces or to the oxidized surfaces of a variety of other polymeric and non-polymeric materials. Thus, components can be fabricated and then oxidized and essentially irreversibly sealed to other silicone polymer surfaces, or to the surfaces of other substrates reactive with the oxidized silicone polymer surfaces, without the need for separate adhesives or other sealing means. In most cases, sealing can be completed simply by contacting an oxidized silicone surface to another surface without the need to apply auxiliary pressure to form the seal. That is, the pre-oxidized silicone surface acts as a contact adhesive against suitable mating surfaces. Specifically, in addition to being irreversibly sealable to itself, oxidized silicone such as oxidized PDMS can also be sealed irreversibly to a range of oxidized materials other than itself including, for example, glass, silicon, silicon oxide, quartz, silicon nitride, polyethylene, polystyrene, glassy carbon, and epoxy polymers, which have been oxidized in a similar fashion to the PDMS surface (for example, via exposure to an oxygen-containing plasma). Oxidation and sealing methods useful in the context of the present invention, as well as overall molding techniques, are described in the art, for example, in an article entitled "Rapid Prototyping of Microfluidic Systems and Polydimethylsiloxane," *Anal. Chem.*, 70:474-480, 1998 (Duffy et al.), incorporated herein by reference.

Another advantage to forming microfluidic structures of the invention (or interior, fluid-contacting surfaces) from oxidized silicone polymers is that these surfaces can be much more hydrophilic than the surfaces of typical elastomeric polymers (where a hydrophilic interior surface is desired). Such hydrophilic channel surfaces can thus be more easily filled and wetted with aqueous solutions than can structures comprised of typical, unoxidized elastomeric polymers or other hydrophobic materials.

In some embodiments, the device may be an electrical and/or a mechanical device applicable or affixable to the surface of the skin, e.g., using adhesive, or other techniques such as those described herein. As another example, the device may be a handheld device that is applied to the surface of the skin of a subject. In some cases, however, the device may be sufficiently small or portable that the subject can self-administer the device. In certain embodiments, the device may also be powered. In some instances, the device may be applied to the surface of the skin, and is not inserted into the skin. In other embodiments, however, at least a portion of the device may be inserted into the skin, for example, mechanically. For example, in one embodiment, the device may include a cutter, such as a hypodermic needle, a knife blade, a piercing element (e.g., a solid or hollow needle), or the like, as discussed herein.

In some cases, the device may be designed such that portions of the device are separable. For example, a first portion of the device may be removed from the surface of the skin, leaving other portions of the device behind on the skin. In one embodiment, a stop may also be included to prevent or control the depth to which the cutter or other device inserts into the skin, e.g., to control penetration to the epidermis, dermis, etc.

Accordingly, as described herein, devices of the invention can be single-stage or multi-stage in some cases. That is, the device can define a single unit that includes one or more components integrally connected to each other which cannot readily be removed from each other by a user, or can include one or more components which are designed to be and can readily be removed from each other. As a non-limiting example of the later, a two-stage patch can be provided for application to the skin of a subject. The patch can include a first stage designed to reside proximate the skin of the subject for the duration of the analysis, which might include an analysis region, a reservoir or other material for creating vacuum or otherwise promoting the flow of fluid or other materials relative to the analysis region, a needle or a microneedle to access interstitial fluid via suction blister or without a suction blister or the like. A second stage or portion of the device can be provided that can initiate operation of the device. For example, the two stage device can be applied to the skin of the user. A button or other component or switch associated with the second portion of the device can be activated by the subject to cause insertion of a needle or a microneedle to the skin of the subject, or the like. Then, the second stage can be removed, e.g., by the subject, and the first stage can remain on the skin to facilitate analysis. In another arrangement, a two-stage device can be provided where the first stage includes visualization or other signal-producing components and the second stage includes components necessary to facilitate the analysis, e.g., the second stage can include all components necessary to access bodily fluid, transport the fluid (if necessary) to a site of analysis, and the like, and that stage can be removed, leaving only a visualization stage for the subject or another entity to view or otherwise analyze as described herein.

Any or all of the arrangements described herein can be provided proximate a subject, for example on or proximate a subject's skin. Activation of the devices can be carried out as described herein. For example, an on-skin device can be in the form of a patch or the like, optionally including multiple layers for activation, sensing, fluid flow, etc. Activation of the devices can be carried out in a variety of ways. In one manner, a patch can be applied to a subject and a region of the patch activated (e.g., tapped by a user) to inject a needle or a microneedle so as to access interstitial fluid. The same or a different tapping or pushing action can activate a vacuum source, open and/or close one or more of a variety of valves, or the like. The device can be a simple one in which it is applied to the skin and operates automatically (where e.g., application to the skin access interstitial fluid and draws interstitial fluid into an analysis region) or the patch or other device can be applied to the skin and one tapping or other activation can cause fluid to flow through administration of a needle or a microneedle, opening of a valve, activation of vacuum, or any combination. Any number of activation protocols can be carried out by a user repeatedly pushing or tapping a location or selectively, sequentially, and/or periodically activating a variety of switches (e.g., tapping regions of a patch). In another arrangement, activation of needles or microneedles, creation of suction blisters, opening and/or closing of valves, and other techniques to facilitate one or more analysis can be carried out electronically or in other manners facilitated by the subject or by an outside controlling entity. For example, a device or patch can be provided proximate a subject's skin and a radio frequency, electromagnetic, or other signal can be provided by a nearby controller or a distant source to activate any of the needles, blister devices, valves or other components of the devices described so that any assay or assays can be carried out as desired.

As discussed, various devices of the invention include various systems and methods for delivering and/or withdrawing fluid from the subject, according to certain embodiments. For instance, the device may comprise a hypodermic needle, a vacuum source, a hygroscopic agent, or the like. Non-limiting examples of suitable delivery techniques include, but are not limited to, injection (e.g., using needles such as hypodermic needles) or a jet injector, such as those discussed below. For instance, in one embodiment, the fluid is delivered and/or withdrawn manually, e.g., by manipulating a plunger on a syringe. In another embodiment, the fluid can be delivered and/or withdrawn from the skin mechanically or automatically, e.g., using a piston pump or the like. Fluid may also be withdrawn using vacuums such as those discussed herein. For example, vacuum may be applied to a conduit, such as a needle, in fluidic communication with interstitial fluid, e.g., within a pooled region of fluid, in order to draw up at least a portion of the fluid from the pooled region. In yet another embodiment, fluid is withdrawn using capillary action (e.g., using a hypodermic needle having a suitably narrow inner diameter). In still another embodiment, pressure may be applied to force fluid out of the needle.

In some embodiments, fluids may be delivered to or withdrawn from the skin using vacuum. The vacuum may be an external vacuum source, and/or the vacuum source may be self-contained within the device. For example, vacuums of at least about 50 mmHg, at least about 100 mmHg, at least about 150 mmHg, at least about 200 mmHg, at least about 250 mmHg, at least about 300 mmHg, at least about 350 mmHg, at least about 400 mmHg, at least about 450 mmHg, at least about 500 mmHg, at least 550 mmHg, at least 600 mmHg, at least 650 mmHg, at least about 700 mmHg, or at least about 750 mmHg may be applied to the skin. As used herein, "vacuum" refers to pressures that are below atmospheric pressure.

In one set of embodiments, a pressure differential (e.g. a vacuum) may be created by a pressure regulator. As used here, "pressure regulator" is a pressure controller component or system able to create a pressure differential between two or more locations. The pressure differential should be at least sufficient to urge the movement of fluid or other material in accordance with various embodiments of the invention as discussed herein, and the absolute pressures at the two or more locations are not important so long as their differential is appropriate, and their absolute values are reasonable for the purposes discussed herein. For example, the pressure regulator may produce a pressure higher than atmospheric pressure in one location, relative to a lower pressure at another location (atmospheric pressure or some other pressure), where the differential between the pressures is sufficient to urge fluid in accordance with the invention. In another example, the regulator or controller will involve a pressure lower than atmospheric pressure (a vacuum) in one location, and a higher pressure at another location(s) (atmospheric pressure or a different pressure) where the differential between the pressures is sufficient to urge fluid in accordance with the invention. Wherever "vacuum" or "pressure" is used herein, in association with a pressure regulator or pressure differential of the invention, it should be understood that the opposite can be implemented as well, as would be understood by those of ordinary skill in the art, i.e., a vacuum chamber can be replaced in many instances with a pressure chamber, for creating a pressure differential suitable for urging the movement of fluid or other material.

The pressure regulator may be an external source of vacuum (e.g. a lab, clinic, hospital, etc., house vacuum line or external vacuum pump), a mechanical device, a vacuum chamber, pre-packaged vacuum chamber, or the like. Vacuum chambers can be used in some embodiments, where the device contains, e.g., regions in which a vacuum exits or can be created (e.g. a variable volume chamber, a change in volume of which will affect vacuum or pressure). A vacuum chamber can include pre-evacuated (i.e., pre-packaged) chambers or regions, and/or self-contained actuators.

A "self-contained" vacuum (or pressure) regulator means one that is associated with (e.g., on or within) the device, e.g. one that defines an integral part of the device, or is a separate component constructed and arranged to be specifically connectable to the particular device to form a pressure differential (i.e., not a connection to an external source of vacuum such as a hospital's, clinic's, or lab's house vacuum line, or a vacuum pump suitable for very general use). In some embodiments, the self-contained vacuum source may be actuated in some fashion to create a vacuum within the device. For instance, the self-contained vacuum source may include a piston, a syringe, a mechanical device such as a vacuum pump able to create a vacuum within the device, and/or chemicals or other reactants that can react to increase or decrease pressure which, with the assistance of mechanical or other means driven by the reaction, can form a pressure differential associated with a pressure regulator. Chemical reaction can also drive mechanical actuation with or without a change in pressure based on the chemical reaction itself. A self-contained vacuum source can also include an expandable foam, a shape memory material, or the like.

One category of self-contained vacuum or pressure regulators of the invention includes self-contained assisted regulators. These are regulators that, upon actuation (e.g., the push of a button, or automatic actuation upon, e.g., removal from a package or urging a device against the skin), a vacuum or pressure associated with the device is formed where the force that pressurizes or evacuates a chamber is not the same as the actuation force. Examples of self-contained assisted regulators include chambers evacuated by expansion driven by a spring triggered by actuation, release of a shape-memory material or expandable material upon actuation, initiation of a chemical reaction upon actuation, or the like.

Another category of self-contained vacuum or pressure regulators of the invention are devices that are not necessarily pre-packaged with pressure or vacuum, but which can be pressurized or evacuated, e.g. by a subject, health care professional at a hospital or clinic prior to use, e.g. by connecting a chamber of the device to a source of vacuum or pressure. For example, the subject, or another person, may actuate the device to create a pressure or vacuum within the device, for example, immediately prior to use of the device.

The vacuum or pressure regulator may be a "pre-packaged" pressure or vacuum chamber in the device when used (i.e., the device can be provided ready for use by a subject or practitioner with an evacuated region on or in the device, without the need for any actuation to form the initial vacuum). A pre-packaged pressure or vacuum chamber regulator can, e.g., be a region evacuated (relative to atmospheric pressure) upon manufacture and/or at some point prior to the point at which it is used by a subject or practitioner. For example, a chamber is evacuated upon manufacture, or after manufacture but before delivery of the device to the user, e.g. the clinician or subject.

For instance, in some embodiments, the device contains a vacuum chamber having a vacuum of at least about 50 mmHg, at least about 100 mmHg, at least about 150 mmHg, at least about 200 mmHg, at least about 250 mmHg, at least about 300 mmHg, at least about 350 mmHg, at least about 400 mmHg, at least about 450 mmHg, at least about 500 mmHg, at least about 550 mmHg, at least about 600 mmHg, at least about 650 mmHg, at least about 700 mmHg, or at least about 750 mmHg below atmospheric pressure.

In some cases, the device may be applicable or affixable to the surface of the skin. For example, in one set of embodiments, the device may include a support structure that contains an adhesive that can be used to immobilize the device to the skin. The adhesive may be permanent or temporary, and may be used to affix the device to the surface of the skin. The adhesive may be any suitable adhesive, for example, a pressure sensitive adhesive, a contact adhesive, a permanent adhesive, a hydrogel adhesive, a cyanoacrylate, glue, gum, hot melts, epoxy, or the like. In most cases, the adhesive is chosen to be biocompatible or hypoallergenic.

In another set of embodiments, the device may be mechanically held to the skin, for example, the device may include mechanical elements such as straps, belts, buckles, strings, ties, elastic bands, or the like. For example, a strap may be worn around the device to hold the device in place against the skin of the subject. In yet another set of embodiments, a combination of these and/or other techniques may be used. As one non-limiting example, the device may be affixed to a subject's arm or leg using adhesive and a strap.

In some embodiments, the device may include a support structure for application to the skin of the subject. The support structure may be used, as discussed herein, for applying the fluid transporter to the surface of the skin of the subject, e.g., so that fluid may be delivered and/or withdrawn from the skin of the subject. In some cases, the support structure may immobilize the fluid transporter such that the fluid transporter cannot move relative to the support structure; in other cases, however, the fluid transporter may be able to move relative to the support structure. In one embodiment, as a non-limiting example, the fluid transporter is immobilized relative to the support structure, and the support structure is positioned within the device such that application of the device to the skin causes at least a portion of the fluid transporter to pierce the skin of the subject.

For instance, in one set of embodiments, the support structure, or a portion of the support structure, may move from a first position to a second position. For example, the first position may be one where the support structure has been immobilized relative thereto a fluid transporter does not contact the skin (e.g., the fluid transporter may be contained within a recess), while the second position may be one where the fluid transporter does contact the skin, and in some cases, the fluid transporter may pierce the skin. The support structure may be moved using any suitable technique, e.g., manually, mechanically, electromagnetically, using a servo mechanism, or the like. In one set of embodiments, for example, the support structure may be moved from a first position to a second position by pushing a button on the device, which causes the support structure to move (either directly, or through a mechanism linking the button with the support structure). Other mechanisms (e.g., dials, etc., as discussed herein) may be used in conjunction of or instead of a button. In another set of embodiments, the support structure may be moved from a first position to a second position automatically, for example, upon activation by a computer, upon remote activation, after a period of time has elapsed, or the like. For example, in one embodiment, a servo connected to the support structure is activated electronically, moving the support structure from the first position to the second position.

In some cases, the support structure may also be moved from the second position to the first position. For example, after fluid has been delivered and/or withdrawn from the skin, e.g., using a fluid transporter the support structure may be moved, which may move the fluid transporter away from contact with the skin. The support structure may be moved from the second position to the first position using any suitable technique, including those described above, and the technique for moving the support structure from the second position to the first position may be the same or different as that moving the support structure from the first position to the second position.

In some cases, the support structure may be able to draw skin towards the fluid transporter. For example, in one set of embodiments, the support structure may include a vacuum interface, such as is described herein. The interface may be connected with a vacuum source (external and/or internal to the device), and when a vacuum is applied, skin may be drawn towards the support structure, e.g., for contact with a fluid transporter, such as one or more needles and/or microneedles.

In certain embodiments, the device may also contain an activator. The activator may be constructed and arranged to cause exposure of the fluid transporter to the skin upon activation of the activator. For example, the activator may cause a chemical to be released to contact the skin, a needle to be driven into the skin, a vacuum to be applied to the skin, a jet of fluid to be directed to the skin, or the like. The activator may be activated by the subject, and/or by another person (e.g., a health care provider), or the device itself may be self-activating, e.g., upon application to the skin of a subject. The activator may be activated once, or multiple times in some cases.

The device may be activated, for example, by pushing a button, pressing a switch, moving a slider, turning a dial, or the like. The subject, and/or another person, may activate the activator. In some cases, the device may be remotely activated. For example, a health care provider may send an electromagnetic signal which is received by the device in order to activate the device, e.g., a wireless signal, a Bluetooth signal, an Internet signal, a radio signal, etc.

In one set of embodiments, the device may also include a sensor, for example embedded within or integrally connected to the device, or positioned remotely but with physical, electrical, and/or optical connection with the device so as to be able to sense a compartment within the device. For example, the sensor may be in fluidic communication with fluid withdrawn from a subject, directly, via a microfluidic channel, an analytical chamber, etc. The sensor may be able to sense an analyte, e.g., one that is suspected of being in a fluid withdrawn from a subject. For example, a sensor may be free of any physical connection with the device, but may be positioned so as to detect the results of interaction of electromagnetic radiation, such as infrared, ultraviolet, or visible light, which has been directed toward a portion of the device, e.g., a compartment within the device. As another example, a sensor may be positioned on or within the device, and may sense activity in a compartment by being connected optically to the compartment. Sensing communication can also be provided where the compartment is in communication with a sensor fluidly, optically or visually, thermally, pneumatically, electronically, or the like, so as to be able to sense a condition of the compartment. As one example, the sensor may be positioned downstream of a compartment, within a channel such a microfluidic channel, or the like.

The sensor may be, for example, a pH sensor, an optical sensor, an oxygen sensor, a sensor able to detect the concentration of a substance, or the like. Other examples of analytes that the sensor may be used to determine include, but are not limited to, metal ions, proteins, nucleic acids (e.g. DNA, RNA, etc.), drugs, sugars (e.g., glucose), hormones (e.g., estradiol, estrone, progesterone, progestin, testosterone, androstenedione, etc.), carbohydrates, or other analytes of interest. Non-limiting examples of sensors useful in the invention include dye-based detection systems, affinity-based detection systems, microfabricated gravimetric analyzers, CCD cameras, optical detectors, optical microscopy systems, electrical systems, thermocouples and thermistors, pressure sensors, etc. Those of ordinary skill in the art will be able to identify other sensors for use in the invention. The sensor can include a colorimetric detection system in some cases, which may be external to the device, or microfabricated into the device in certain cases. As an example of a colorimetric detection system, if a dye or a fluorescent entity is used (e.g. in a particle), the colorimetric detection system may be able to detect a change or shift in the frequency and/or intensity of the dye or fluorescent entity.

As described herein, any of a variety of signaling or display methods, associated with analyses, can be provided including signaling visually, by smell, sound, feel, taste, or the like, in one set of embodiments. Signal structures and generators include, but are not limited to, displays (visual, LED, light, etc.), speakers, chemical-releasing compartments (e.g., containing a volatile chemical), mechanical devices, heaters, coolers, or the like. In some cases, the signal structure or generator may be integral with the device (e.g., integrally connected with a support structure for application to the skin of the subject, e.g., containing a fluid transporter such as a needle or a microneedle), or the signal structure or generator may not be integrally connected with the support structure. As used herein, a "signal structure" or a "signal generator" is any apparatus able to generate a signal that is related to a condition of a medium. For example, the medium may be a bodily fluid, such as blood or interstitial fluid.

In some embodiments, signaling methods such as these may be used to indicate the presence and/or concentration of an analyte determined by the sensor, e.g., to the subject, and/or to another entity, such as those described below. Where a visual signal is provided, it can be provided in the form of change in opaqueness, a change in intensity of color and/or opaqueness, or can be in the form of a message (e.g., numerical signal, or the like), an icon (e.g., signaling by shape or otherwise a particular medical condition), a brand, logo, or the like. For instance, in one embodiment, the device may include a display. A written message such as "take next dose," or "glucose level is high" or a numerical value might be provided, or a message such as "toxin is present." These messages, icons, logos, or the like can be provided as an electronic read-out by a component of a device and/or can be displayed as in inherent arrangement of one or more components of the device.

In some embodiments, a device is provided where the device determines a physical condition of a subject and produces a signal related to the condition that can be readily understood by the subject (e.g., by provision of a visual "OK" signal as described above) or can be designed so as not to be readily understandable by a subject. Where not readily understandable, the signal can take a variety of forms. In one form, the signal might be a series of letters or numbers that mean nothing to the subject (e.g., A1278CDQ) which would have meaning to a medical professional or the like (and/or be decodable by the same, e.g., with reference to a suitable decoder) and can be associated with a particular physiological condition. Alternatively, a signal in the form of bar code can be provided by a device such that, under a particular condition or set of conditions the bar code appears and/or disappears, or changes, and can be read by a bar code reader to communicate information about the subject or analyte. In another embodiment, the device can be designed such that an ultraviolet signal is produced, or a signal that can be read only under ultraviolet light (e.g., a simple spot or patch, or any other signal such as a series of number, letters, bar code, message, or the like that can be readily understandable or not readily understandable by a subject) can be provided. The signal may be invisible to the human eye but, upon application UV light or other excitation energy, may be readable. The signal can be easily readable or understandable by a user via visual observation, or with other sensory activity such as smell, feel, etc. In another set of embodiments equipment as described above may be needed to determine a signal provided by the device, such as equipment in a clinical setting, etc. In some cases, the device is able to transmit a signal indicative of the analyte to a receiver, e.g., as a wireless signal, a Bluetooth signal, an Internet signal, a radio signal, etc.

In some embodiments, quantitative and/or qualitative analyses can be provided by a device. That is, the device in some cases may provide analyses that allow "yes/no" tests or the like, or tests that provide information on the quantity, concentration, or level of a particular analyte or analytes. Display configurations can be provided by the invention that reflect the amount of a particular analyte present in a subject at a particular point in time, or any other variable (presence of analysis over time, type of analyte, etc.) display configurations can take a variety of forms. In one example, a dial can be provided, similar to that of a speedometer with a series of level indications (e.g., numbers around the dial) and a "needle" or other device that indicates a particular level. In other configurations, a particular area of the device (e.g., on a display) can exist that is filled in to a greater or lesser extent depending upon the presence and/or quantity of a particular analyte present, e.g., in the form of a bar graph. In another arrangement a "color wheel" can be provided where the amount of a particular analyte present can control which colors of the wheel are visible. Or, different analytes can cause different colors of a wheel or different bars of a graph to become visible or invisible in a multiple analyte analysis. Multiple-analyte quantitative analyses can be reflected in multiple color wheels, a single color wheel with different colors per analyte where the intensity of each color reflects the amount of the analyte, or, for example, a plurality of bar graphs where each bar graph is reflective of a particular analyte and the level of the bar (and/or degree to which an area is filled in with visible color or other visible feature) is reflective of the amount of the analyte. As with all embodiments here, whatever signal is displayed can be understandable or not understandable to any number of participants. For example, it can be understandable to a subject or not understandable to a subject. Where not understandable it might need to be decoded, read electronically, or the like. Where read electronically, for example, a device may provide a signal that is not understandable to a subject or not even visible or otherwise able to be sensed by a subject, and a reader can be provided adjacent or approximate to the device that can provide a visible signal that is understandable or not understandable to the subject, or can transmit a signal to another entity for analysis.

In connection with any signals associated with any analyses described herein, another, potentially related signal or other display (or smell, taste, or the like) can be provided which can assist in interpreting and/or evaluating the signal. In one arrangement, a calibration or control is provided proximate to (or otherwise easily comparable with) a signal, e.g., a visual calibration/control or comparator next to or close to a visual signal provided by a device and/or implanted agents, particles, or the like.

A visual control or reference can be used with another sensory signal, such as that of smell, taste, temperature, itch, etc. A reference/control and/or experimental confirmation component can be provided, to be used in connection with an in-skin test or vice versa. References/indicators can also be used to indicate the state of life of a device, changing color or intensity and/or changing in another signaling aspect as the device changes relative to its useful life, so that a user can determine when the device should no longer be relied upon and/or removed. For certain devices, an indicator or control can be effected by adding analyte to the control (e.g., from a source outside of the source to be determine) to confirm operability of the device and/or to provide a reference against which to measure a signal of the device. For example, a device can include a button to be tapped by a user which will allow an analyte from a reservoir to transfer to an indicator region to provide a signal, to demonstrate operability of the device and/or provide a comparator for analysis.

Many of the embodiments described herein involve a quantitative analysis and related signal, i.e., the ability to determine the relative amount or concentration of an analyte in a medium. This can be accomplished in a variety of ways. For example, where an agent (e.g. a binding partner attached to a nanoparticle) is used to capture and analyze an analyte, the agent can be provided in a gradient in concentration across a sensing region of the device. Or a sensing region can include a membrane or other apparatus through which analyte is required to flow or pass prior to capture and identification, and the pathway for analyte travel can vary as a function of position of display region. For example, a membrane can be provided across a sensing region, through which analyte must pass prior to interacting with a layer of binding and/or signaling agent, and the membrane may vary in thickness laterally in a direction related to "bar graph" readout. Where a small amount of analyte is present, it may pass through the thinner portion but not the thicker portion of the membrane, but where a larger amount is present, it may pass across a thicker portion. The boundary (where one exists) between a region through which analyte passes, and one through which it does not completely pass, can define the "line" of the bar graph. Other ways of achieving the same or a similar result can include varying the concentration of a scavenger or transporter of the analyte, or an intermediate reactive species (between analyte and signaling event), across a membrane or other article, gradient in porosity or selectivity of the membrane, ability to absorb or transport sample fluid, or the like. These principles, in combination with other disclosure herein, can be used to facilitate any or all of the quantitative analyses described herein.

In one set of embodiments, a subject having a condition such as a physiological condition to be analyzed (or other user, such as medical personnel) reads and/or otherwise determines a signal from a device. For example, the device may transmit a signal indicative of a condition of the subject and/or the device. Alternatively, or in addition, a signal produced by a device can be acquired in the form of a representation (e.g. a digitized signal, or the like) and transmitted to another entity for analysis and/or action. For example, a signal can be produced by a device, e.g., based on a sensor reading of an analyte, based on fluid delivered and/or withdrawn from the skin, based on a condition of the device, or the like. The signal may represent any suitable data or image. For example, the signal may represent the presence and/or concentration of an analyte in fluid withdrawn from a subject, the amount of fluid withdrawn from a subject and/or delivered to the subject, the number of times the device has been used, the battery life of the device, the amount of vacuum left in the device, the cleanliness or sterility of the device, the identity of the device (e.g., where multiple devices are given unique identification numbers, to prevent counterfeiting, accidental exchange of equipment to incorrect users, etc.), or the like. For instance, in one set of embodiments, an image of the signal (e.g., a visual image or photograph) can be obtained and transmitted to a different entity (for example, a user can take a cell phone picture of a signal generated by the device and send it, via cell phone, the other entity).

The other entity that the signal is transmitted to can be a human (e.g., a clinician) or a machine. In some cases, the other entity may be able to analyze the signal and take appropriate action. In one arrangement, the other entity is a machine or processor that analyzes the signal and optionally sends a signal back to the device to give direction as to activity (e.g., a cell phone can be used to transmit an image of a signal to a processor which, under one set of conditions, transmits a signal back to the same cell phone giving direction to the user, or takes other action). Other actions can include automatic stimulation of the device or a related device to dispense a medicament or pharmaceutical, or the like. The signal to direct dispensing of a pharmaceutical can take place via the same used to transmit the signal to the entity (e.g., cell phone) or a different vehicle or pathway. Telephone transmission lines, wireless networks, Internet communication, and the like can also facilitate communication of this type.

As one specific example, a device may be a glucose monitor. As signal may be generated by the device and an image of the signal captured by a cell phone camera and then transmitted via cell phone to a clinician. The clinician may then determine that the glucose (or e.g., insulin) level is appropriate or inappropriate and send a message indicating this back to the subject via cell phone.

Information regarding the analysis can also be transmitted to the same or a different entity, or a different location simply by removing the device or a portion of the device from the subject and transferring it to a different location. For example, a device can be used in connection with a subject to analyze presence and/or amount of a particular analyte. At some point after the onset of use, the device, or a portion of the device carrying a signal or signals indicative of the analysis or analyses, can be removed and, e.g., attached to a record associated with the subject. As a specific example, a patch or other device can be worn by a subject to determine presence and/or amount of one or more analytes qualitatively, quantitatively, and/or over time. The subject can visit a clinician who can remove the patch (or other device) or a portion of the patch and in some cases, attach it to a medical record associated with the subject.

According to various sets of embodiments, the device may be one, or multiple times, depending on the application. For instance, obtaining samples for sensing, according to certain embodiments of the invention, can be done such that sensing can be carried out continuously, discretely, or a combination of these. For example, where a bodily fluid such as blood or interstitial fluid is accessed for determination of an analyte, fluid can be accessed discretely (i.e., as a single dose, once or multiple times), or continuously by creating a continuous flow of fluid which can be analyzed once or any number of times. Additionally, testing can be carried out once, at a single point in time, or at multiple points in time, and/or from multiple samples (e.g., at multiple locations relative to the subject).

Alternatively or in addition, testing can be carried out continuously over any number of points in time involving one or any number of locations relative to the subject or other multiple samples. As an example, one bolus or isolated sample, of fluid such as interstitial fluid can be obtained. From that fluid a test can be carried out to determine whether a particular analyte or other agent exists in the fluid. Alternatively, two or more tests can be carried out involving that quantity of fluid to determine the presence and/or quantity of two or more analytes, and any number of such tests can be carried out. Tests involving that quantity of fluid can be carried out simultaneously or over a period of time. For example, a test for a particular analyte can be carried out at various points in time to determine whether the result changes over time, or different analytes can be determined at different points in time. As another example, a pool of fluid can be formed between layers of skin via, e.g., a suction blister and either within the suction blister or from fluid drawn from the suction blister and placed elsewhere, any of the above and other analysis can be carried out at one or more points in time. Where a suction blister is formed in such a way that interstitial fluid within the blister changes over time (where an equilibrium exists between interstitial fluid within the subject and interstitial fluid in the suction blister itself, i.e., the fluid within the blister is ever changing to reflect the content of the interstitial fluid of the subject in the region of the blister over time). Testing of fluid within or from the suction blister at various points in time can provide useful information.

In another example, a needle or a microneedle, or other device(s) can be used to access a fluid of a subject such as interstitial fluid (with or without use of a suction blister). Fluid can be drawn to a point of analysis and analyzed in any manner described herein. For example, an analysis can be carried out once, to determine the presence and/or quantity of a single analyte, or a number of tests can be carried out. From a single sample of fluid, a particular test or number of tests can be carried out essentially simultaneously, or analyses can be carried out over time. Moreover, fluid can be drawn continuously from the subject and one or more tests can be carried out of any number of points in time. A variety of reasons for carrying out one or more tests over the course of time exists, as would be understood by those of ordinary skill in the art. One such reason is to determine whether the quantity or another characteristic of an analyte is constant in a subject, or changes over time. A variety of specific techniques for continuous and/or discrete testing will be described herein.

In some cases, the device may comprise a cutter able to cut or pierce the surface of the skin. The cutter may comprise any mechanism able to create a path to a fluid within the skin, e.g., through which fluids may be delivered and/or removed from the skin. For example, the cutter may comprise a hypodermic needle, a knife blade, a piercing element (e.g., a solid or a hollow needle), or the like, which can be applied to the skin to create a suitable conduit for the withdrawal of fluid from the skin. In one embodiment, a cutter is used to create such a pathway and removed, then fluid is removed via this pathway using any suitable technique. In another embodiment, the cutter remains in place within the skin, and fluid may be drawn through a conduit within the cutter.

In some embodiments, fluid may be withdrawn using an electric charge. For example, reverse iontophoresis may be used. Without wishing to be bound by any theory, reverse iontophoresis uses a small electric current to drive charged and highly polar compounds across the skin. Since the skin is negatively charged at physiologic pH, it acts as a perm-selective membrane to cations, and the passage of counterions across the skin induces an electroosmotic solvent flow that may carry neutral molecules in the anode-to-cathode direction. Components in the solvent flow may be analyzed as described elsewhere herein. In some instances, a reverse iontophoresis apparatus may comprise an anode cell and a cathode cell, each in contact with the skin. The anode cell may be filled, for example, with an aqueous buffer solution (i.e., aqueous Tris buffer) having a pH greater than 4 and an electrolyte (i.e. sodium chloride). The cathode cell can be filled with aqueous buffer. As one example, a first electrode (e.g., an anode) can be inserted into the anode cell and a second electrode (e.g., a cathode) can be inserted in the cathode cell. In some embodiments, the electrodes are not in direct contact with the skin.

A current may be applied to induce reverse iontophoresis, thereby extracting a fluid from the skin. The current applied may be, for example, greater than 0.01 mA, greater than 0.3 mA, greater than 0.1 mA, greater than 0.3 mA, greater than 0.5 mA, or greater than 1 mA. It should be understood that currents outside these ranges may be used as well. The current may be applied for a set period of time. For example, the current may be applied for greater than 30 seconds, greater than 1 minute, greater than 5 minutes, greater than 30 minutes, greater than 1 hour, greater than 2 hours, or greater than 5 hours. It should be understood that times outside these ranges may be used as well.

In one set of embodiments, the device may comprise an apparatus for ablating the skin. Without wishing to be bound by any theory, it is believed that ablation comprises removing a microscopic patch of stratum corneum (i.e., ablation forms a micropore), thus allowing access to bodily fluids. In some cases, thermal, radiofrequency, and/or laser energy may be used for ablation. In some instances, thermal ablation may be applied using a heating element. Radiofrequency ablation may be carried out using a frequency and energy capable of heating water and/or tissue. A laser may also be used to irradiate a location on the skin to remove a portion. In some embodiments, the heat may be applied in pulses such that a steep temperature gradient exists essentially perpendicular to the surface of the skin. For example, a temperature of at least 100° C., at least 200° C., at least 300° C., or at least 400° C. may be applied for less than 1 second, less than 0.1 seconds, less than 0.01 seconds, less than 0.005 seconds, or less than 0.001 seconds.

In some embodiments, the device may comprise a mechanism for taking a solid sample of tissue. For example, a solid tissue sample may be acquired by methods such as scraping the skin or cutting out a portion. Scraping may comprise a reciprocating action whereby an instrument is scraped along the surface of the skin in two or more directions. Scraping can also be accomplished by a rotating action, for example parallel to the surface of the skin and in one direction (i.e., with a roller drum) or parallel to the surface of the skin and in a circular manner (i.e., with a drilling instrument). A cutting mechanism may comprise a blade capable of making one or more incisions and a mechanism for removing a portion of tissue (i.e., by suction or mechanically picking up) or may use a pincer mechanism for cutting out a portion of tissue. A cutting mechanism may also function by a coring action. For example, a hollow cylindrical device can be penetrated into the skin such that a cylindrical core of tissue may be removed. A solid sample may be analyzed directly or may be liquefied prior to analysis. Liquefaction can comprise treatment with organic solvents, enzymatic solutions, etc.

In some cases, the device may contain a shape memory polymer and/or metal, for example, one that is sensitive to heat. Upon insertion into the skin between the epidermis and dermis, the shape memory polymer may expand in some fashion, allowing separation of the epidermis and the dermis to occur. Non-limiting examples of shape-memory polymers and metals include Nitinol, compositions of oligo(epsilon-caprolactone)diol and crystallisable oligo(rho-dioxanone) diol, or compositions of oligo(epsilon-caprolactone)dimethacrylate and n-butyl acrylate. For example, the shape memory polymer (or metal) may have a first, condensed shape at a temperature below the body temperature of the subject, but upon insertion into the skin, the cutter heats and assumes a second, larger shape that causes at least some separation to occur between the epidermis and dermis.

The device, in certain embodiments, may also contain a portion able to determine the fluid removed from the skin. For example, a portion of the device may contain a sensor, or reagents able to interact with an analyte contained or suspected to be present within the withdrawn fluid from the subject, for example, a marker for a disease state. As non-limiting examples, the sensor may contain an antibody able to interact with a marker for a disease state, an enzyme such as glucose oxidase or glucose 1-dehydrogenase able to detect glucose, or the like. The analyte may be determined quantitatively or qualitatively, and/or the presence or absence of the analyte within the withdrawn fluid may be determined in some cases. Those of ordinary skill in the art will be aware of many suitable commercially-available sensors, and the specific sensor used may depend on the particular analyte being sensed. For instance, various non-limiting examples of sensor techniques include pressure or temperature measurements, spectroscopy such as infrared, absorption, fluorescence, UV/visible, FTIR ("Fourier Transform Infrared Spectroscopy"), or Raman; piezoelectric measurements; immunoassays; electrical measurements, electrochemical measurements (e.g., ion-specific electrodes); magnetic measurements, optical measurements such as optical density measurements; circular dichroism; light scattering measurements such as quasielectric light scattering; polarimetry; refractometry; chemical indicators such as dyes; or turbidity measurements, including nephelometry.

As mentioned, certain aspects of the present invention are generally directed to particles such as anisotropic particles or colloids, which can be used in a wide variety of applications. For instance, the particles may be present within the skin, or externally of the skin, e.g., in a device on the surface of the skin. The particles may include microparticles and/or nanoparticles. As discussed above, a "microparticle" is a particle having an average diameter on the order of micrometers (i.e., between about 1 micrometer and about 1 mm), while a "nanoparticle" is a particle having an average diameter on the order of nanometers (i.e., between about 1 nm and about 1 micrometer. The particles may be spherical or non-spherical, in some cases. For example, the particles may be oblong or elongated, or have other shapes such as those disclosed in U.S. patent application Ser. No. 11/851,974, filed Sep. 7, 2007, entitled "Engineering Shape of Polymeric Micro- and Nanoparticles," by S. Mitragotri, et al.; International Patent Application No. PCT/US2007/077889, filed Sep. 7, 2007, entitled "Engineering Shape of Polymeric Micro- and Nanoparticles," by S. Mitragotri, et al., published as WO 2008/031035 on Mar. 13, 2008; U.S. patent application Ser. No. 11/272,194, filed Nov. 10, 2005, entitled "Multi-phasic Nanoparticles," by J. Lahann, et al., published as U.S. Patent Application Publication No. 2006/0201390 on Sep. 14, 2006; or U.S. patent application Ser. No. 11/763,842, filed Jun. 15, 2007, entitled "Multi-Phasic Bioadhesive Nan-Objects as Biofunctional Elements in Drug Delivery Systems," by J. Lahann, published as U.S. Patent Application Publication No. 2007/0237800 on Oct. 11, 2007, each of which is incorporated herein by reference.

An "anisotropic" particle, as used herein, is one that is not spherically symmetric (although the particle may still exhibit various symmetries), although the particle may have sufficient asymmetry to carry out at least some of the goals of the invention as described herein. On the basis of the present disclosure, this will be clearly understood by those of ordinary skill in the art. The asymmetry can be asymmetry of shape, of composition, or both. As an example, a particle having the shape of an egg or an American football is not perfectly spherical, and thus exhibits anisotropy. As another example, a sphere painted such that exactly one half is red and one half is blue (or otherwise presents different surface characteristics on different sides) is also anisotropic, as it is not perfectly spherically symmetric, although it would still exhibit at least one axis of symmetry.

Accordingly, a particle may be anisotropic due to its shape and/or due to two or more regions that are present on the surface of and/or within the particle. For instance, the particle may include a first surface region and a second surface region that is distinct from the first region in some way, e.g., due to coloration, surface coating, the presence of one or more reaction entities, etc. The particle may include different regions only on its surface or the particle may internally include two or more different regions, portions of which extend to the surface of the particle. The regions may have the same or different shapes, and be distributed in any pattern on the surface of the particle. For instance, the regions may divide the particle into two hemispheres, such that each hemisphere has the same shape and/or the same surface area, or the regions may be distributed in more complex arrangements.

Non-limiting examples of particles can be seen in U.S. patent application Ser. No. 11/272,194, filed Nov. 10, 2005, entitled "Multi-phasic Nanoparticles," by J. Lahann, et al., published as U.S. Patent Application Publication No. 2006/0201390 on Sep. 14, 2006; U.S. patent application Ser. No. 11/763,842, filed Jun. 15, 2007, entitled "Multi-Phasic Bioadhesive Nan-Objects as Biofunctional Elements in Drug Delivery Systems," by J. Lahann, published as U.S. Patent Application Publication No. 2007/0237800 on Oct. 11, 2007; or U.S. Provisional Patent Application Ser. No. 61/058,796, filed Jun. 4, 2008, entitled "Compositions and Methods for Diagnostics, Therapies, and Other Applications," by D. Levinson, each of which is incorporated herein by reference.

The particles (which may be anisotropic, or not anisotropic) may be formed of any suitable material, depending on the application. For example, the particles may comprise a glass, and/or a polymer such as polyethylene, polystyrene, silicone, polyfluoroethylene, polyacrylic acid, a polyamide (e.g., nylon), polycarbonate, polysulfone, polyurethane, polybutadiene, polybutylene, polyethersulfone, polyetherimide, polyphenylene oxide, polymethylpentene, polyvinylchloride, polyvinylidene chloride, polyphthalamide, polyphenylene sulfide, polyester, polyetheretherketone, polyimide, polymethylmethacylate and/or polypropylene. In some cases, the particles may comprise a ceramic such as tricalcium phosphate, hydroxyapatite, fluorapatite, aluminum oxide, or zirconium oxide. In some cases (for example, in certain biological applications), the particles may be formed from biocompatible and/or biodegradable polymers such as polylactic and/or polyglycolic acids, polyanhydride, polycaprolactone, polyethylene oxide, polyacrylamide, polyacrylic acid, polybutylene terephthalate, starch, cellulose, chitosan, and/or combinations of these. In one set of embodiments, the particles may comprise a hydrogel, such as agarose, collagen, or fibrin. The particles may include a magnetically susceptible material in some cases, e.g., a material displaying paramagnetism or ferromagnetism. For instance, the particles may include iron, iron oxide, magnetite, hematite, or some other compound containing iron, or the like. In another embodiment, the particles can include a conductive material (e.g., a metal such as titanium, copper, platinum, silver, gold, tantalum, palladium, rhodium, etc.), or a semiconductive material (e.g., silicon, germanium, CdSe, CdS, etc.). Other particles potentially useful in the practice of the invention include ZnS, ZnO, $TiO_2$, AgI, AgBr, $HgI_2$, PbS, PbSe, ZnTe, CdTe, $In_2S_3$, $In_2Se_3$, $Cd_3P_2$, $Cd_3As_2$, InAs, or GaAs. The particles may include other species as well, such as cells, biochemical species such as nucleic acids (e.g., RNA, DNA, PNA, etc.), proteins, peptides, enzymes, nanoparticles, quantum dots, fragrances, indicators, dyes, fluorescent species, chemicals, small molecules (e.g., having a molecular weight of less than about 1 kDa), or the like.

As an example, certain particles or colloids such as gold nanoparticles can be coated with agents capable of interacting with an analyte. Such particles may associate with each other, or conversely, dissociate in the presence of analyte in such a manner that a change is conferred upon the light absorption property of the material containing the particles. This approach can also be used as a skin-based visual sensor, in one embodiment. A non-limiting example of a technique for identifying aggregates is disclosed in U.S. patent application Ser. No. 09/344,667, filed Jun. 25, 1999, entitled "Nanoparticles Having Oligonucleotides Attached Thereto and Uses Therefor," by Mirkin, et al., now U.S. Pat. No. 6,361,944, issued Mar. 26, 2002.

The particles may also have any shape or size. For instance, the particles may have an average diameter of less than about 5 mm or 2 mm, or less than about 1 mm, or less than about 500 microns, less than about 200 microns, less than about 100 microns, less than about 60 microns, less than about 50 microns, less than about 40 microns, less than about 30 microns, less than about 25 microns, less than about 10 microns, less than about 3 microns, less than about 1 micron, less than about 300 nm, less than about 100 nm, less than about 30 nm, or less than about 10 nm. As discussed, the particles may be spherical or non-spherical. The average diameter of a non-spherical particle is the diameter of a perfect sphere having the same volume as the non-spherical particle. If the particle is non-spherical, the particle may have a shape of, for instance, an ellipsoid, a cube, a fiber, a tube, a rod, or an irregular shape. In some cases, the particles may be hollow or porous. Other shapes are also possible, for instance, core/shell structures (e.g., having different compositions), rectangular disks, high aspect ratio rectangular disks, high aspect ratio rods, worms, oblate ellipses, prolate ellipses, elliptical disks, UFOs, circular disks, barrels, bullets, pills, pulleys, biconvex lenses, ribbons, ravioli, flat pills, bicones, diamond disks, emarginate disks, elongated hexagonal disks, tacos, wrinkled prolate ellipsoids, wrinkled oblate ellipsoids, porous ellipsoid disks, and the like. See, e.g., International Patent Application No. PCT/US2007/077889, filed Sep. 7, 2007, entitled "Engineering Shape of Polymeric Micro- and Nanoparticles," by S. Mitragotri, et al., published as WO 2008/031035 on Mar. 13, 2008, incorporated herein by reference.

In one aspect of the invention, a particle may include one or more reaction entities present on the surface (or at least a portion of the surface) of the particle. The reaction entity may be any entity able to interact with and/or associate with an analyte, or another reaction entity. For instance, the reaction entity may be a binding partner able to bind an analyte. For example, the reaction entity may be a molecule that can undergo binding with a particular analyte. The reaction entities may be used, for example, to determine pH or metal ions, proteins, nucleic acids (e.g. DNA, RNA, etc.), drugs, sugars (e.g., glucose), hormones (e.g., estradiol, estrone, progesterone, progestin, testosterone, androstenedione, etc.), carbohydrates, or other analytes of interest.

The term "binding partner" refers to a molecule that can undergo binding with a particular molecule, e.g., an analyte. For example, the binding may be highly specific and/or non-covalent. Binding partners which form highly specific, non-covalent, physiochemical interactions with one another are defined herein as "complementary." Biological binding partners are examples. For example, Protein A is a binding partner of the biological molecule IgG, and vice versa. Other non-limiting examples include nucleic acid-nucleic acid binding, nucleic acid-protein binding, protein-protein binding, enzyme-substrate binding, receptor-ligand binding, receptor-hormone binding, antibody-antigen binding, etc. Binding partners include specific, semi-specific, and non-specific binding partners as known to those of ordinary skill in the art. For example, Protein A is usually regarded as a "non-specific" or semi-specific binder. As another example, the particles may contain an enzyme such as glucose oxidase or glucose 1-dehydrogenase, or a lectin such as concanavalin A that is able to bind to glucose.

As additional examples, binding partners may include antibody/antigen pairs, ligand/receptor pairs, enzyme/substrate pairs and complementary nucleic acids or aptamers. Examples of suitable epitopes which may be used for antibody/antigen binding pairs include, but are not limited to, HA, FLAG, c-Myc, glutathione-S-transferase, $His_6$, GFP, DIG, biotin and avidin. Antibodies may be monoclonal or polyclonal. Suitable antibodies for use as binding partners include antigen-binding fragments, including separate heavy chains, light chains Fab, Fab', $F(ab')_2$, Fabc, and Fv. Antibodies also include bispecific or bifunctional antibodies. Exemplary binding partners include biotin/avidin, biotin/streptavidin, biotin/neutravidin and glutathione-S-transferase/glutathione.

The term "binding" generally refers to the interaction between a corresponding pair of molecules or surfaces that exhibit mutual affinity or binding capacity, typically due to specific or non-specific binding or interaction, including, but not limited to, biochemical, physiological, and/or chemical interactions. The binding may be between biological molecules, including proteins, nucleic acids, glycoproteins, carbohydrates, hormones, or the like. Specific non-limiting examples include antibody/antigen, antibody/hapten, enzyme/substrate, enzyme/inhibitor, enzyme/cofactor, binding protein/substrate, carrier protein/substrate, lectin/carbohydrate, receptor/hormone, receptor/effector, complementary strands of nucleic acid, protein/nucleic acid repressor/inducer, ligand/cell surface receptor, vim s/ligand, virus/cell surface receptor, etc. As another example, the binding agent may be a chelating agent (e.g., ethylenediaminetetraacetic acid) or an ion selective polymer (e.g., a block copolymer such as poly(carbonate-b-dimethylsiloxane), a crown ether, or the like). As another example, the binding partners may be biotin and streptavidin, or the binding partners may be various antibodies raised against a protein.

The term "specifically binds," when referring to a binding partner (e.g., protein, nucleic acid, antibody, etc.), refers to a reaction that is determinative of the presence and/or identity of one or other member of the binding pair in a mixture of heterogeneous molecules (e.g., proteins and other biologics). Thus, for example, in the case of a receptor/ligand binding pair, the ligand would specifically and/or preferentially select its receptor from a complex mixture of molecules, or vice versa. An enzyme would specifically bind to its substrate, a nucleic acid would specifically bind to its complement, an antibody would specifically bind to its antigen, etc. The binding may be by one or more of a variety of mechanisms including, but not limited to ionic interactions or electrostatic interactions, covalent interactions, hydrophobic interactions, van der Waals interactions, etc.

Thus, the invention provides, in certain embodiments, particles that are able to bind to an analyte, e.g., via a binding partner to the analyte, and such particles can be used to determine the analyte. Such determination may occur within the skin, and/or externally of the subject, e.g., within a device on the surface of the skin, depending on the embodiment. "Determine," in this context, generally refers to the analysis of a species, for example, quantitatively or qualitatively, and/or the detection of the presence or absence of the species. The species may be, for example, a bodily fluid and/or an analyte suspected of being present in the bodily fluid. "Determining" may also refer to the analysis of an interaction between two or more species, for example, quantitatively or qualitatively, and/or by detecting the presence or absence of the interaction, e.g. determination of the binding between two species. "Determining" also means detecting or quantifying interaction between species. As an example, an analyte may cause a determinable change in a property of the particles, e.g., a change in a chemical property of the particles, a change in the appearance and/or optical properties of the particles, a change in the temperature of the particles, a change in an electrical property of the particles, etc. In some cases, the change may be one that is determinable by a human, unaided by any equipment that may be directly applied to the human. For instance, the determinable change may be a change in appearance (e.g., color), a change in temperature, the production of an odor, etc., which can be determined by a human without the use of any equipment (e.g., using the eyes). Non-limiting examples include temperature changes, chemical reactions or other interactions (e.g., with capsaicin) that can be sensed, or the like. Examples of capsaicin and capsaicin-like molecules include, but are not limited to, dihydrocapsaicin, nordihydrocapsaicin, homodihydrocapsaicin, homocapsaicin, or nonivamide. Without wishing to be bound by any theory, it is believed that interactions with capsaicin and capsaicin-like molecules can be sensed by a subject, since such molecules may interact with certain nerve endings, which produces a sensation of burning.

In one set of embodiments, more than one particle may be able to bind an analyte, and/or more than one analyte may bind to a particle. In some cases, such multiple binding properties may result in the clustering of more than one particle to an analyte and/or more than one analyte to a particle. Such clustering can be determined in some fashion, e.g., via a change in an optical property. As an example, an aggregate of particles may form in the absence of analyte, but disaggregate (at least partially) in the presence of the analyte, e.g., if the analyte and the particles exhibit competitive or non-competitive inhibition. Such binding and/or aggregation may be equilibrium-based in some cases, i.e., the binding and/or aggregation occurs in equilibrium with unbinding or disaggregation processes. Thus, when the environment surrounding the particles is altered in some fashion (e.g., a change in concentration of an analyte), the equilibrium may shift in response, which can be readily determined (e.g., as a change in color). It should be noted that such equilibrium-based systems may be able to determine such changes in environment, in some cases, without the need to apply any energy to determine the environmental change. In another example, aggregation may cause a change in an electrical or a magnetic property.

As an example, an optical property of the medium containing the clusters may be altered in some fashion (e.g., exhibiting different light scattering properties, different opacities, different degrees of transparency, etc.), which can be correlated with the analyte. In some cases, the color may change in intensity, for example, the clustering of particles may bring two or more reactants into close proximity.

Other properties may also be determined besides color. Accordingly, it should be understood that the use of "color" with respect to particles as used herein is by way of example only, and other properties may be determined instead of or in addition to color. For instance, clustering of aniostropic particles may cause a change in an electrical or a magnetic property of the particles, which can be determined by determining an electrical or a magnetic field. As another example, the first region and the second region may have different reactivities (e.g., the first region may be reactive to an enyzme, an antibody, etc.), and aggregation of the particles may cause a net change in the reactivity. As still another example, size may be used to determine the particles and/or the analyte. For instance, the aggregates may be visually identifiable, the aggregates may form a precipitant, or the like. Thus, for example, the particles (which may be anisotropic or not anisotropic) may appear to be a first color when separate, and a second color when aggregation occurs. In some cases, an assay (e.g., an agglutination assay) may be used to determine the aggregation. In another set of embodiments, an ordering of the particles may be determined. For example, in the absence of an analyte, the particles may be ordered on the surface of a substrate; while in the presence of an analyte, the particles may bind to the analyte and become disordered relative to the surface. This ordering may be determined, for example, as a change in an optical property of the surface (e.g., index of refraction, color, opacity, etc.). As yet other examples, a shape change may be produced using a shape memory polymer or a "smart polymer," and this may be able to be sensed by feel. Alternatively, a color may be released, a hydrolysis reaction may occur, or aggregation of the particles may occur.

In one embodiment, the binding or presence of the analyte, e.g. present in interstitial fluid optionally created using a suction blister device, results in a tactile change (e.g., change in shape or texture). For example, shape memory polymer (SMPs) can be used to detect the presence of one or more analytes. SMPs are generally characterized as phase segregated linear block co-polymers having a hard segment and a soft segment. The hard segment is typically crystalline, with a defined melting point, and the soft segment is typically amorphous, with a defined glass transition temperature. In some embodiments, however, the hard segment is amorphous and has a glass transition temperature rather than a melting point. In other embodiments, the soft segment is crystalline and has a melting point rather than a glass transition temperature. The melting point or glass transition temperature of the soft segment is substantially less than the melting point or glass transition temperature of the hard segment.

When the SMP is heated above the melting point or glass transition temperature of the hard segment, the material can be shaped. This (original) shape can be "memorized" by cooling the SMP below the melting point or glass transition temperature of the hard segment. When the shaped SMP is cooled below the melting point or glass transition temperature of the soft segment while the shape is deformed, that (temporary) shape is fixed. The original shape is recovered by heating the material above the melting point or glass transition temperature of the soft segment but below the melting point or glass transition temperature of the hard segment. The recovery of the original shape, which is induced by an increase in temperature, is called the thermal shape memory effect. Properties that describe the shape memory capabilities of a material include the shape recovery of the original shape and the shape fixity of the temporary shape Shape memory polymers can contain at least one physical crosslink (physical interaction of the hard segment) or contain covalent crosslinks instead of a hard segment. The shape memory polymers also can be interpenetrating networks or semi-interpenetrating networks. In addition to changes in state from a solid to liquid state (melting point or glass transition temperature), hard and soft segments may undergo solid to solid state transitions, and can undergo ionic interactions involving polyelectrolyte segments or supramolecular effects based on highly organized hydrogen bonds.

Other polymers that can shape or phase change as a function of temperature include PLURONICS®. These are also known as poloxamers, nonionic triblock copolymers composed of a central hydrophobic chain of polyoxypropylene (poly(propylene oxide)) flanked by two hydrophilic chains of polyoxyethylene (poly(ethylene oxide)). Because the lengths of the polymer blocks can be customized, many different poloxamers exist that have slightly different properties. For the generic term "poloxamer," these copolymers are commonly named with the letter "P" (for poloxamer) followed by three digits, the first two digits×100 give the approximate molecular mass of the polyoxypropylene core, and the last digit×10 gives the percentage polyoxyethylene content (e.g., P407=Poloxamer with a polyoxypropylene molecular mass of 4,000 g/mol and a 70% polyoxyethylene content). For the PLURONICS® tradename, coding of these copolymers starts with a letter to define its physical form at room temperature (L=liquid, P=paste, F=flake (solid)) followed by two or three digits. The first digit (two digits in a three-digit number) in the numerical designation, multiplied by 300, indicates the approximate molecular weight of the hydrophobe; and the last digit×10 gives the percentage polyoxyethylene content (e.g., L61=Pluronic with a polyoxypropylene molecular mass of 1,800 g/mol and a 10% polyoxyethylene content).

Other temperature sensitive polymers that form gels that have a distinct phase change at its lower critical solution temperature (LCST) including the cross-linked copolymers comprising hydrophobic monomers, hydrogen bonding monomers, and thermosensitive monomers.

Additional thermal responsive, water soluble polymers including the co-polymerization product of N-isopropyl acrylamide (NIP); 1-vinyl-2-pyrrolidinone (VPD); and optionally, acrylic acid (AA), change shape as a function of temperature. As the proportion of component AA increases, the Lower Critical Solution Temperature (LCST) decreases and the COOH reactive groups increase, which impart high reactivity to the copolymer. By adjusting the proportion of the monomers, a broad range of LCST can be manipulated from about 20° C. to 80° C.

While the shape memory effect is typically described in the context of a thermal effect, the polymers can change their shape in response to application of light, changes in ionic concentration and/or pH, electric field, magnetic field or ultrasound. For example, a SMP can include at least one hard segment and at least one soft segment, wherein at least two of the segments, e.g., two soft segments, are linked to each other via a functional group that may be cleavable under application of light, electric field, magnetic field, or ultrasound. The temporary shape may be fixed by crosslinking the linear polymers. By cleaving those links the original shape can be recovered. The stimuli for crosslinking and cleaving these bonds can be the same or different.

In one embodiment, the shape memory polymer composition binds, complexes to, or interacts with an analyte, which can be a chromophore. The hard and/or soft segments can include double bonds that shift from cis to trans isomers when the chromophores absorb light. Light can therefore be used to detect the presence of a chromophore analyte by observing whether or not the double bond isomerizes.

The shape memory effect can also be induced by changes in ionic strength or pH. Various functional groups are known to crosslink in the presence of certain ions or in response to changes in pH. For example, calcium ions are known to crosslink amine and alcohol groups, i.e., the amine groups on alginate can be crosslinked with calcium ions. Also, carboxylate and amine groups become charged species at certain pHs. When these species are charged, they can crosslink with ions of the opposite charge. The presence of groups, which respond to changes in the concentration of an ionic species and/or to changes in pH, on the hard and/or soft segments results in reversible linkages between these segments. One can fix the shape of an object while crosslinking the segments. After the shape has been deformed, alteration of the ionic concentration or pH can result in cleavage of the ionic interactions which formed the cros slinks between the segments, thereby relieving the strain caused by the deformation and thus returning the object to its original shape. Because ionic bonds are made and broken in this process, it can only be performed once. The bonds, however, can be re-formed by altering the ionic concentration and/or pH, so the process can be repeated as desired. Thus, in this embodiment, the presence of an analyte which changes the ionic strength or pH can induce a shape memory effect in the polymer confirming the presence of the analyte.

Electric and/or magnetic fields can also be used to induce a shape memory effect. Various moieties, such as chromophores with a large number of delocalized electrons, increase in temperature in response to pulses of applied electric or magnetic fields as a result of the increased electron flow caused by the fields. After the materials increase in temperature, they can undergo temperature induced shape memory in the same manner as if the materials were heated directly. These compositions are useful in biomedical applications where the direct application of heat to an implanted material may be difficult, but the application of an applied magnetic or electric field would only affect those molecules with the chromophore, and not heat the surrounding tissue. For example, the presence of a chromophore analyte with a large number of delocalized electrons can cause an increase in temperature in the microenvironment surrounding the shape memory polymer implant in response to pulses of applied electric or magnetic fields. This increase in temperature can in turn cause a thermal shape memory effect, thus confirming the presence of a particular analyte.

Other types of "smart polymers" may also be used. The combination of the capabilities of stimuli-responsive components such as polymers and interactive molecules to form site-specific conjugates are useful in a variety of assays, separations, processing, and other uses. The polymer chain conformation and volume can be manipulated through alteration in pH, temperature, light, or other stimuli. The interactive molecules can be biomolecules like proteins or peptides, such as antibodies, receptors, or enzymes, polysaccharides or glycoproteins which specifically bind to ligands, or nucleic acids such as antisense, ribozymes, and aptamers, or ligands for organic or inorganic molecules in the environment or manufacturing processes. The stimuli-responsive polymers are coupled to recognition biomolecules at a specific site so that the polymer can be manipulated by stimulation to alter ligand-biomolecule binding at an adjacent binding site, for example, the biotin binding site of streptavidin, the antigen-binding site of an antibody or the active, substrate-binding site of an enzyme. Binding may be completely blocked (i.e., the conjugate acts as an on-off switch) or partially blocked (i.e., the conjugate acts as a rheostat to partially block binding or to block binding only of larger ligands). Once a ligand is bound, it may also be ejected from the binding site by stimulating one (or more) conjugated polymers to cause ejection of the ligand and whatever is attached to it. Alternatively, selective partitioning, phase separation or precipitation of the polymer-conjugated biomolecule can be achieved through exposure of the stimulus-responsive component to an appropriate environmental stimulus.

Liquid crystal polymeric materials can also be used to provide a signal for detection or quantification of analyte. Liquid crystals are materials that exhibit long-range order in only one or two dimensions, not all three. A distinguishing characteristic of the liquid crystalline state is the tendency of the molecules, or mesogens, to point along a common axis, known as the director. This feature is in contrast to materials where the molecules are in the liquid or amorphous phase, which have no intrinsic order, and molecules in the solid state, which are highly ordered and have little translational freedom. The characteristic orientational order of the liquid crystal state falls between the crystalline and liquid phases. These can be pressure or temperature sensitive, and react by producing a change in color or shape.

In some cases, the particles may contain a diagnostic agent able to determine an analyte. An example of an analyte within a subject is glucose (e.g., for diabetics); other potentially suitable analytes include ions such as sodium, potassium, chloride, calcium, magnesium, and/or bicarbonate (e.g., to determine dehydration); gases such as carbon dioxide or oxygen; pH; metabolites such as urea, blood urea nitrogen or creatinine; hormones such as estradiol, estrone, progesterone, progestin, testosterone, androstenedione, etc. (e.g., to determine pregnancy, illicit drug use, or the like); or cholesterol. Still other potentially suitable analytes include various pathogens such as bacteria or viruses, and/or markers produced by such pathogens. For example, a particle may include an antibody directed at a marker produced by bacteria. In addition, more than one analyte may be determined in a subject, e.g., through the use of different particle types and/or through the use of particles able to determine more than one analyte, such as those discussed above. For instance, a first set of particles may determine a first analyte and a second set of particles may determine a second analyte. In some cases, such particles may be used to determine a physical condition of a subject. For instance, the particles may exhibit a first color indicating a healthy state and a second color indicating a disease state. In some cases, the appearance of the particles may be used to determine a degree of health. For instance, the particles may exhibit a first color indicating a healthy state, a second color indicating a warning state, and a third color indicating a dangerous state, or the particles may exhibit a range of colors indicating a degree of health of the subject.

Binding partners to these and/or other species are well-known in the art. Non-limiting examples include pH-sensitive entities such as phenol red, bromothymol blue, chlorophenol red, fluorescein, HPTS, 5(6)-carboxy-2',7'-dimethoxyfluorescein SNARF, and phenothalein; entities sensitive to calcium such as Fura-2 and Indo-1; entities sensitive to chloride such as 6-methoxy-N-(3-sulfopropyl)-quinolinim and lucigenin; entities sensitive to nitric oxide such as 4-amino-5-methylamino-2',7'-difluorofluorescein; entities sensitive to dissolved oxygen such as tris(4,4'-diphenyl-2,2'-bipyridine) ruthenium (II) chloride pentahydrate; entities sensitive to dissolved $CO_2$; entities sensitive to fatty acids, such as BODIPY 530-labeled glycerophosphoethanolamine; entities sensitive to proteins such as 4-amino-4'-benzamidostilbene-2-2'-disulfonic acid (sensitive to serum albumin), X-Gal or NBT/BCIP (sensitive to certain enzymes), $Tb^{3+}$ from $TbCl_3$ (sensitive to certain calcium-binding proteins), BODIPY FL phallacidin (sensitive to actin), or BOCILLIN FL (sensitive to certain penicillin-binding proteins); entities sensitive to concentration of glucose, lactose or other components, or entities sensitive to proteases, lactates or other metabolic byproducts, entities sensitive to proteins, antibodies, or other cellular products.

In one set of embodiments, at least some of the particles used in the subject to determine the analyte are anisotropic particles (in other cases, however, the particles are not necessarily anisotropic), and in some cases, substantially all of the particles are anisotropic particles. In certain cases, at least about 10%, at least about 30%, at least about 40%, at least about 50%, at least about 60%, at least about 70%, at least about 80%, at least about 90%, at least about 95%, or at least about 99% of the particles are anisotropic particles. In one embodiment, the anisotropic particles may have a first region having a first color and a second region having a second color distinct from the first color, and the particles, upon exposure to the analyte within the subject, may form clusters that exhibit an excess of the second region or second color relative to the first region or first color, as discussed above. The particles may be present, for example, in the bloodstream and/or within the skin of the subject.

In some cases, the particles, after delivery into the skin may give the appearance of a "tattoo" or a permanent mark within the skin, and the tattoo or other mark may be of any color and/or size. For instance, in one embodiment, anisotropic particles such as those described above that are able to bind glucose may be delivered into the skin of a subject, and such particles, after deposition within the skin, may react to the presence or absence of glucose by exhibiting a change in color. The particles may exhibit a color change based on the presence or absence of glucose, and/or the concentration of glucose. For instance, the particles may exhibit a first color (e.g., green) when not aggregated, and a second color (e.g., red or brown) when aggregated, or the particles may be invisible when not aggregated, but visible (e.g., exhibiting a color) when aggregated. The particles may be, for example, anisotropic particles having a first surface region having a first color (e.g., green) and a second surface region having a second color (e.g., red), and the first surface region may contain a binding partner to glucose. At low levels of glucose, the particles may exhibit a combination of the first and second colors, while at higher levels of glucose, the particles may exhibit more of the second color.

It should be noted that causing clustering of particles to occur is not limited to only the exposure of particles to an analyte. In another set of embodiments, for example, the clustering or aggregation properties of the particles is externally controlled in some fashion. For instance, an electrical, magnetic, and/or a mechanical force can be used to bring the particles closer together and/or cause the particles to separate. Thus, in some cases, the application of an electrical, magnetic, and/or a mechanical force to the particles causes the particles to exhibit a change in color. The clustering or aggregation of particles as discussed herein is not limited to generally spherical aggregations. In some cases, the particles may cluster onto a surface, or the particles may be aligned in some fashion relative to the surface due to an analyte or other external force.

In addition, it should be noted that the particles may contain reaction entities that are not necessarily binding partners to an analyte. For instance, there may be first particles containing a first reaction entity and a second reaction entity that reacts with the first reaction entity; when the particles are brought together in some fashion (e.g., by exposure to an analyte or other chemical that is recognized by binding partners on each of the particles, by the application of an electrical, magnetic, and/or a mechanical force to bring the particles closer together, etc.), the first and second reaction entities may react. As a specific example, the reaction between the first and second reaction entities may be an endothermic or an exothermic reaction; thus, when the particles are brought together, a temperature change is produced, which can be determined in some fashion. As another example, a reaction between the first and second reactants may cause the release of a material. In some cases, the material may be one that can be sensed by a subject, e.g., capsaicin, an acid, an allergen, or the like. Thus, the subject may sense the change as a change in temperature, pain, itchiness, swelling, or the like.

In some cases, the particles may be suspended in a carrying fluid, e.g., saline, or the particles may be contained within a matrix, e.g., a porous matrix that is or becomes accessible by interstitial fluid after delivery, or a hydrogel matrix, etc. For instance, the matrix may be formed from a biodegradable and/or biocompatible material such as polylactic acid, polyglycolic acid, poly(lactic-co-glycolic acid), etc., or other similar materials.

In some cases, the matrix may prevent or at least inhibit an immunological response by the subject to the presence of the particles, while allowing equilibration of analytes, etc. with the particles to occur, e.g., if the matrix is porous. For instance, the pores of a porous matrix may be such that immune cells are unable to penetrate, while proteins, small molecules (e.g., glucose, ions, dissolved gases, etc.) can penetrate. The pores may be, for instance, less than about 5 micrometers, less than about 4 micrometers, less than about 3 micrometers, less than about 2 micrometers, less than about 1.5 micrometers, less than about 1.0 micrometers, less than about 0.75 micrometers, less than about 0.6 micrometers, less than about 0.5 micrometers, less than about 0.4 micrometers, less than about 0.3 micrometers, less than about 0.1 micrometers, less than about 0.07 micrometers, and in other embodiments, or less than about 0.05 micrometers. The matrix may comprise, for example, biocompatible and/or biodegradable polymers such as polylactic and/or polyglycolic acids, polyanhydride, polycaprolactone, polyethylene oxide, polybutylene terephthalate, starch, cellulose, chitosan, and/or combinations of these, and/or other materials such as agarose, collagen, fibrin, or the like.

Thus, in one set of embodiments, particles are provided which can be analogized to a light on an automotive dashboard, e.g., green for normal, yellow for suspicious, slightly low or slightly high, and red for abnormal. The subject then knows that they need to be seen, and the degree of urgency, by appropriate medical personnel. The particles may be placed and read at the site of detection. For example, the devices may provide a visual colorimetic signal, but other signals are possible, such as smell (released upon change in pH or temperature, for example), or tactile (shape change due to chemical reaction).

Signals from the particles can be used to generate a pattern or color which is indicative of the presence and/or amount of analyte. The density, shape, color, or intensity of the pattern or color may provide a yes-no type answer or may be graduated to provide quantitative amounts. This could also be effected by exposure to a pH or temperature change in some embodiments. Other patterns include, for example, + and − signs, arrows (e.g., up arrows or down arrows), faces (smiley, neutral, sad), etc., or the like.

In one set of embodiments, the skin surface may change in feel when there is a reaction. For example, shape memory polymers may say "OK" when the cholesterol level is below 150 mg/dl. These may change to ready "HIGH" when the cholesterol level exceeds 200 mg/dl. The device may be blank or lack definition at values between these levels.

The particles may change when reacted with analyte. This may result in a smell such as a food odor being released as a function of a pH or temperature change. For instance, an encapsulated scent may be released. In some cases, FDA GRAS ingredients may be used as signals.

These may be applied to the skin to measure a change in temperature indicative of disease or inflammation. In one embodiment, the device may be colorless or a color indicative of normal temperature (for example, green), or the device will display a message such as "OK." In the event the temperature exceeds a certain level, such as 101° F., the color changes (for example, yellow for caution or red for warning or critical) or the message changes (for example, if shape memory polymers are used) to read "HOT." These are particularly useful in a setting such as a day care, where there are a number of babies or young children to supervise, and fevers can occur rapidly.

In another embodiment, the particles may be used to measure a decrease in blood oxygen, or measure the amount of molecules such as glucose, cholesterol, triglycerides, cancer markers, or infectious agents, by providing agents that specifically react with the molecules, and signal generating agents which produce signal in an amount correlated with the amounts of the molecules that react. As another non-limiting example, analogous to the temperature monitor, a pre-set level can be used to create a message that says "C high," for example, or "insulin!" for example, which effects a color change.

As discussed above, the devices may, instead of a color change or message change, change shape, emit a scent or flavor, or otherwise notify the person of a need to seek further information. In some cases, this might be to seek medical attention where the indicator of a disorder can be confirmed and appropriate medical intervention obtained. In the case of temperature indicative of a fever, the caregiver might measure the temperature using a standard thermometer. In the case of a hormone change, indicative of pregnancy or ovulation, an ELISA test might be performed using a urine sample. In the case of high glucose, this could be confirmed using a standard glucose monitor and a blood sample.

In another aspect, the particles may be delivered for cosmetic purposes, e.g., as a permanent or temporary tattoo. In some cases, the "tattoo" or particles contained within the skin may be alterable by the administration of an electrical, magnetic, and/or a mechanical force to the subject. For instance, by applying such forces, the particles may be caused to cluster, which may result in a change in color, as discussed above. Thus, one embodiment of the invention is directed to a cosmetic mark in the skin that can be altered by application of an external stimulus, such as an electrical, magnetic, and/or a mechanical force, and/or a chemical applied to the skin (e.g., a chemical which is a binding partner of a species on the particle).

The tattoo (or other mark) present in the skin may have any function, e.g., as a decorative art, or as an identification system. For instance, a tattoo may be verified by applying a stimulus to the subject (e.g., an electric field, a magnetic field, a mechanical force, a chemical, etc.), and confirming the tattoo by identifying a change in the mark, such as a change in color. The change in the mark may be permanent or temporary. As a specific example, a stimulus may be applied to anisotropic particles containing a first region exhibiting a first color and a second region exhibiting a second color. In the absence of the stimulus, the particles exhibit a blend of the first and second colors; however, under application of the stimulus, only one color may be exhibited as the particles are aligned. This identification of a change in color may be used, for example, artistically, or as an identifying mark. As mentioned, in some cases, such a mark may be permanent or temporary. As another example, the particles may be invisible (e.g., non-aggregated) in the absence of a stimulus, but become visible (e.g., aggregated) when a stimulus is applied. In some cases, the particles change their appearance while the stimulus is applied, but revert to their original appearance once the stimulus is removed; in other cases, however, the particles may be able to retain their altered appearance for some time following removal of the stimulus, and in some cases, the particles permanently retain their altered appearance.

Figure 11B:
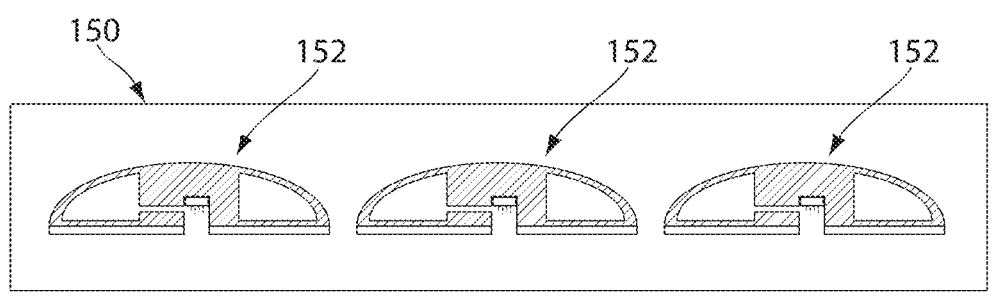
FIG. 11B illustrates a kit containing more than one device, in yet another embodiment of the invention.
Figure 11C:
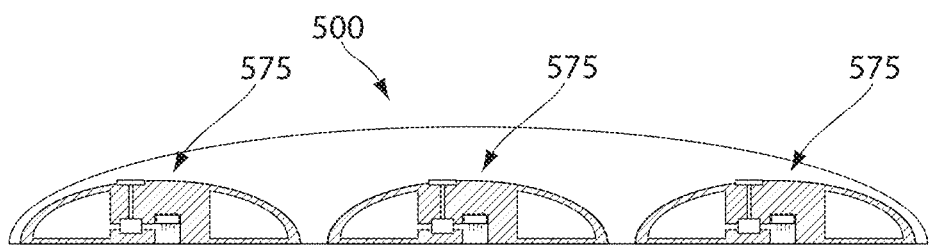
FIG. 11C illustrates a device according to still another embodiment of the invention.

In another aspect, the present invention is directed to a kit including one or more of the compositions previously discussed, e.g., a kit including a particle, a kit including a device for the delivery and/or withdrawal of fluid from the skin, a kit including a device able to create a pooled region of fluid within the skin of a subject, a kit including a device able to determine a fluid, or the like. An example of a kit containing more than one device of the invention is illustrated in FIG. 11B, with kit 150 containing devices 152. A "kit," as used herein, typically defines a package or an assembly including one or more of the compositions or devices of the invention, and/or other compositions or devices associated with the invention, for example, as previously described. For example, in one set of embodiments, the kit may include a device and one or more compositions for use with the device. Each of the compositions of the kit, if present, may be provided in liquid form (e.g., in solution), or in solid form (e.g., a dried powder). In certain cases, some of the compositions may be constitutable or otherwise processable (e.g., to an active form), for example, by the addition of a suitable solvent or other species, which may or may not be provided with the kit. Examples of other compositions or components associated with the invention include, but are not limited to, solvents, surfactants, diluents, salts, buffers, emulsifiers, chelating agents, fillers, antioxidants, binding agents, bulking agents, preservatives, drying agents, antimicrobials, needles, syringes, packaging materials, tubes, bottles, flasks, beakers, dishes, frits, filters, rings, clamps, wraps, patches, containers, tapes, adhesives, and the like, for example, for using, administering, modifying, assembling, storing, packaging, preparing, mixing, diluting, and/or preserving the compositions components for a particular use, for example, to a sample and/or a subject.

A kit of the invention may, in some cases, include instructions in any form that are provided in connection with the compositions of the invention in such a manner that one of ordinary skill in the art would recognize that the instructions are to be associated with the compositions of the invention. For instance, the instructions may include instructions for the use, modification, mixing, diluting, preserving, administering, assembly, storage, packaging, and/or preparation of the compositions and/or other compositions associated with the kit. In some cases, the instructions may also include instructions for the delivery and/or administration of the compositions, for example, for a particular use, e.g., to a sample and/or a subject. The instructions may be provided in any form recognizable by one of ordinary skill in the art as a suitable vehicle for containing such instructions, for example, written or published, verbal, audible (e.g., telephonic), digital, optical, visual (e.g., videotape, DVD, etc.) or electronic communications (including Internet or web-based communications), provided in any manner.

In some embodiments, the present invention is directed to methods of promoting one or more embodiments of the invention as discussed herein. As used herein, "promoted" includes all methods of doing business including, but not limited to, methods of selling, advertising, assigning, licensing, contracting, instructing, educating, researching, importing, exporting, negotiating, financing, loaning, trading, vending, reselling, distributing, repairing, replacing, insuring, suing, patenting, or the like that are associated with the systems, devices, apparatuses, articles, methods, compositions, kits, etc. of the invention as discussed herein. Methods of promotion can be performed by any party including, but not limited to, personal parties, businesses (public or private), partnerships, corporations, trusts, contractual or subcontractual agencies, educational institutions such as colleges and universities, research institutions, hospitals or other clinical institutions, governmental agencies, etc. Promotional activities may include communications of any form (e.g., written, oral, and/or electronic communications, such as, but not limited to, e-mail, telephonic, Internet, Web-based, etc.) that are clearly associated with the invention.

In one set of embodiments, the method of promotion may involve one or more instructions. As used herein, "instructions" can define a component of instructional utility (e.g., directions, guides, warnings, labels, notes, FAQs or "frequently asked questions," etc.), and typically involve written instructions on or associated with the invention and/or with the packaging of the invention. Instructions can also include instructional communications in any form (e.g., oral, electronic, audible, digital, optical, visual, etc.), provided in any manner such that a user will clearly recognize that the instructions are to be associated with the invention, e.g., as discussed herein.

U.S. Provisional Patent Application Ser. No. 61/058,796, filed Jun. 4, 2008, entitled "Compositions and Methods for Diagnostics, Therapies, and Other Applications," by D. Levinson, is incorporated herein by reference. Also incorporated herein by reference are U.S. Provisional Patent Application Ser. No. 61/163,733, filed on Mar. 26, 2009, entitled "Determination of Tracers within Subjects," by D. Levinson; U.S. Provisional Patent Application Ser. No. 61/163,750, filed on Mar. 26, 2009, entitled "Monitoring of Implants and Other Devices," by D. Levinson, et al.; U.S. Provisional Patent Application Ser. No. 61/058,682, filed on Mar. 26, 2009, entitled "Compositions and Methods for Diagnostics, Therapies, and other Applications," by D. Levinson; U.S. Provisional Patent Application Ser. No. 61/163,793, filed Mar. 26, 2009, entitled "Compositions and Methods for Diagnostics, Therapies, and Other Applications," by D. Levinson; U.S. patent application Ser. No. 12/478,756, filed Jun. 4, 2009, entitled "Compositions and Methods for Diagnostics, Therapies, and Other Applications"; International Patent Application No. PCT/US09/046333, filed Jun. 4, 2009, entitled "Compositions and Methods for Diagnostics, Therapies, and Other Applications"; U.S. Provisional Patent Application Ser. No. 61/163,710, filed Mar. 26, 2009, entitled "Systems and Methods for Creating and Using Suction Blisters or Other Pooled Regions of Fluid within the Skin"; U.S. Provisional Patent Application Ser. No. 61/156,632, filed Mar. 2, 2009, entitled "Oxygen Sensor"; U.S. Provisional Patent Application Ser. No. 61/269,436, filed Jun. 24, 2009, entitled "Devices and Techniques associated with Diagnostics, Therapies, and Other Applications, Including Skin-Associated Applications"; U.S. Provisional Patent Application Ser. No. 61/163,791, filed on Mar. 26, 2009, entitled "Compositions and Methods for Rapid One-Step Diagnosis," by D. Levinson; U.S. Provisional Patent Application Ser. No. 61/257,731, filed Nov. 3, 2009, entitled "Devices and Techniques Associated with Diagnostics, Therapies, and Other Applications, Including Skin-Associated Applications"; and U.S. Provisional Patent Application Ser. No. 61/294,543, filed Jan. 13, 2010, entitled "Blood Sampling Device and Method." Also incorporated herein by reference are the following U.S. patent applications being filed on even date herewith: "Oxygen Sensor," by Levinson, et al.; "Systems and Methods for Creating and Using Suction Blisters or Other Pooled Regions of Fluid within the Skin," by Levinson, et al.; and "Devices and Techniques Associated with Diagnostics, Therapies, and Other Applications, Including Skin-Associated Applications," by Bernstein, et al.

In one aspect of the present invention, methods of forming particles such as those described herein are provided. For instance, in one set of embodiments, electrospraying or electrospinning techniques are used to prepare particles. In some cases, two or more fluid streams (including liquid jets) are combined together such that the two or more fluid streams contact over spatial dimensions sufficient to form a composite stream. In some cases, there is little or no mixing of the two or more fluid streams within the composite stream. In some variations, the fluid streams are electrically conductive, and in certain cases, a cone-jet may be formed by combining the two or more fluid streams under the influence of an electric field.

In some cases, the composite stream is directed at a substrate, e.g., by the application of a force field such as an electric field. For instance, if the composite stream is charged, an electric field may be used to urge the composite stream towards a substrate. The composite stream may be continuous or discontinuous in some cases, e.g., forming a series of droplets (which may be spherical or non-spherical). In some cases, the composite stream is hardened prior to and/or upon contact with the substrate. For example, the composite stream may be urged towards the substrate under conditions in which at least a portion of the composite stream (e.g., a solvent) is able to evaporate, causing the remaining stream to harden and/or precipitate, e.g., to form particles, spheres, rods, fibers, or the like. In some variations, the composite stream fragments in droplets that can lead to particle, sphere, rod, and/or fiber formation.

Additional examples of techniques for forming such particles or fibers can be found in U.S. patent application Ser. No. 11/272,194, filed Nov. 10, 2005, entitled "Multi-Phasic Nanoparticles," by Lahann, et al., published as U.S. Patent Application Publication No. 2006/0201390 on Sep. 14, 2006; or priority to U.S. patent application Ser. No. 11/763, 842, filed Jun. 15, 2007, entitled "Multiphasic Biofunctional Nano-Components and Methods for Use Thereof," by Lahann, published as U.S. Patent Application Publication No. 2007/0237800 on Oct. 11, 2007, each of which is incorporated herein by reference.

In one set of embodiments, solvent evaporation techniques may be used. In one embodiment, a polymer may be dissolved in a volatile organic solvent, such as methylene chloride. Drugs or other suitable species are added to the solution, and the mixture is suspended in an aqueous solution that contains a surface active agent such as poly(vinyl alcohol). The resulting emulsion can be stirred until most of the organic solvent evaporated, leaving solid particles. The resulting particles may be washed with water and dried overnight in a lyophilizer. Particles with different sizes or morphologies can be obtained by this method. This method is useful for relatively stable polymers like polyesters and polystyrene.

In another set of embodiments, solvent removal techniques may be used, e.g., for polymers such as polyanhydrides. In one embodiment, a polymer may be dissolved in a volatile organic solvent like methylene chloride. The mixture can be suspended by stirring in an organic oil (such as silicon oil) to form an emulsion. This can be used to make particles from polymers with high melting points and different molecular weights. Particles that range, for example, between 1-2000 microns, 1-1000 microns, 1-500 microns, 1-300 microns, 1-100 microns, 1-30 microns, 1-10 microns, etc. in diameter can be obtained by this procedure. The external morphology of spheres produced with this technique may be controlled by controlling the type of polymer used.

In yet another set of embodiments, spray-drying techniques may be used. In one embodiment, a polymer is dissolved in organic solvent. The solution or the dispersion is then spray-dried. Particles ranging between, for example, between 1-2000 microns, 1-1000 microns, 1-500 microns, 1-300 microns, 1-100 microns, 1-30 microns, 1-10 microns, etc. in diameter can be obtained with a morphology which depends on the type of polymer used.

In still another set of embodiments, interfacial polycondensation techniques may be used. In one embodiment, a monomer is dissolved in a solvent. A second monomer is dissolved in a second solvent (typically aqueous) which is immiscible with the first. An emulsion may be formed by suspending the first solution through stirring in the second solution. Once the emulsion is stabilized, an initiator can be added to the aqueous phase causing interfacial polymerization at the interface of each droplet of emulsion.

In yet another set of embodiments, phase inversion techniques may be used. In one set of embodiments, particles can be formed from polymers using a phase inversion method wherein a polymer is dissolved in a solvent and the mixture is poured into a non-solvent for the polymer, to spontaneously produce particles under favorable conditions. The method can be used to produce particles in a wide range of diameters, including, for example, about 100 nanometers to about 10 microns. Examples of polymers which can be used include polyvinylphenol and polylactic acid. In some cases, the polymer can be dissolved in an organic solvent and then contacted with a non-solvent, which causes phase inversion of the dissolved polymer to form particles, optionally incorporating an antigen or other substance.

In still another set of embodiments, phase separation techniques may be used. In one set of embodiments, the polymer is dissolved in a solvent to form a polymer solution. While continually stirring, a nonsolvent for the polymer may be added to the solution to decrease the polymer's solubility. Depending on the solubility of the polymer in the solvent and nonsolvent, the polymer may precipitate and/or phase separate into a polymer-rich and a polymer-poor phase. Under proper conditions, the polymer in the polymer-rich phase may migrate to the interface with the continuous phase, forming particles.

In yet another set of embodiments, spontaneous emulsification techniques can be used. One set of embodiments involves solidifying emulsified liquid polymer droplets by changing temperature, evaporating solvent, and/or adding chemical cross-linking agents. In still another set of embodiments, hot melt techniques may be used.

In some cases, the particles may comprise a gel. For instance, in one set of embodiments, particles made of gel-type polymers, such as alginate and hyaluronic acid, can be produced through ionic gelation techniques. In one embodiment, polymers can be first dissolved in an aqueous solution and then extruded through a droplet forming device, which in some instances employs a flow of nitrogen and/or other gases to break off the droplet. A slowly stirred (approximately 100-170 RPM) ionic hardening bath may be positioned below the extruding device to catch the forming droplets. The particles are left to incubate in the bath to allow gelation to occur. Particle size may be controlled, for example, by using various size extruders or varying nitrogen gas or polymer solution flow rates. In one embodiment, chitosan particles can be prepared by dissolving the polymer in acidic solution and crosslinking it with tripolyphosphate. In another embodiment, carboxymethyl cellulose (CMC) nanoparticles can be prepared by dissolving the polymer in acid solution and precipitating the nanoparticle with lead ions. In some cases where negatively charged polymers (e.g., alginate, CMC) are used, positively charged ligands (e.g., polylysine, polyethyleneimine) of different molecular weights can be ionically attached.

Other methods known in the art that can be used to prepare nanoparticles include, but are not limited to, polyelectrolyte condensation, single and double emulsion (probe sonication), nanoparticle molding, or electrostatic self-assembly (e.g., polyethylene imine-DNA or liposomes).

In some cases, the particles may include functional groups used to bind or complex the analyte, and such functional groups can be introduced prior to particle formation (e.g., monomers can be functionalized with one or more functional groups for binding or complexing the analyte) or the functional groups can be introduced after particle formation (e.g., by functionalizing the surface of the microparticle with reactive functional groups). The particles may optionally have encapsulated therein one or more core materials. In one embodiment, the particles may be present in an effective amount to provide a signal detectable to the user without the need for additional equipment. For example, the articles should be present in an effective amount to provide a change in taste, smell, shape, and/or color upon binding or complexing the analyte that is easily detectable by the user.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A device for withdrawing blood from the skin and/or from beneath the skin of a subject, the device comprising:
   (a) a recess configured and arranged to be sealingly placed against the skin;
   (b) a plurality of microneedles configured and arranged to be applied to skin within the recess;
   (c) a vacuum chamber having an internal negative pressure before blood is withdrawn into the device and before the device is applied to the skin of the subject;
   (d) a storage chamber, separate from the vacuum chamber and the recess, for receiving blood withdrawn into the recess when the negative pressure from the vacuum chamber is applied to the skin of the subject;
   (e) an activator that, when activated, fluidly communicates the negative pressure from the vacuum chamber to the recess, wherein prior to activating the activator, the device comprises the vacuum chamber and the recess, and the negative pressure from the vacuum chamber is not in fluid communication with the recess; and (f) a microfluidic channel fluidly communicating the vacuum chamber and the storage chamber prior to activation, the microfluidic channel being discrete from the vacuum chamber and the storage chamber and having a smaller cross-sectional area than the cross-sectional area of the storage chamber.

2. The device of claim 1, wherein at least some of the microneedles are solid.

3. The device of claim 1, wherein at least some of the microneedles are hollow.

4. The device of claim 1, wherein the device is self-contained.

5. The device of claim 1, wherein the device comprises at least 6 microneedles.

6. The device of claim 1, further comprising a support structure constructed and arranged to move the plurality of microneedles into contact with the skin, and to withdrawal the plurality of microneedles from the skin after contact with the skin.

7. The device of claim 1, the device further comprising a flow controller able to control blood flow into the storage chamber.

8. The device of claim 7, wherein the flow controller comprises a membrane.

9. The device of claim 1, wherein the vacuum chamber does not have a variable volume.

10. The device of claim 1, further comprising a reaction entity contained within the storage chamber able to react with an analyte contained within the blood.

11. A device for withdrawing blood from the skin and/or from beneath the skin of a subject, the device comprising:
    a fluid transporter comprising one or more microneedles;
    a vacuum chamber having an internal negative pressure before blood is withdrawn into the device and before the device is applied to the skin of the subject;
    a storage chamber, separate from the vacuum chamber, for receiving blood withdrawn into the device when the negative pressure from the vacuum chamber is applied to the skin of the subject; and
    an activator comprising a component activatable by a subject and a portion that, when activated, fluidly communicates the negative pressure from the vacuum chamber to a recess, wherein prior to activating the activator, the device comprises the vacuum chamber and the recess, and the negative pressure from the vacuum chamber is not in fluid communication with the recess.

12. The device of claim 11, wherein at least some of the one or more microneedles are solid.

13. The device of claim 11, wherein at least some of the one or more microneedles are hollow.

14. The device of claim 11, wherein the device is self-contained.

15. The device of claim 11, wherein the device comprises at least 6 microneedles.

16. The device of claim 11, further comprising a support structure constructed and arranged to move the one or more microneedles into contact with the skin, and to withdrawal the plurality of microneedles from the skin after contact with the skin.

17. The device of claim 11, the device further comprising a flow controller able to control blood flow into the storage chamber.

18. The device of claim 17, wherein the flow controller comprises a membrane.

19. The device of claim 11, wherein the vacuum chamber does not have a variable volume.

20. The device of claim 11, further comprising a reaction entity contained within the storage chamber able to react with an analyte contained within the blood.

21. The device of claim 11, wherein the device is constructed and arranged to prevent blood from entering the vacuum chamber.

\* \* \* \* \*